US008343725B2

(12) United States Patent
Croce et al.

(10) Patent No.: US 8,343,725 B2
(45) Date of Patent: *Jan. 1, 2013

(54) METHOD OF DIAGNOSING POOR SURVIVAL PROGNOSIS COLON CANCER USING MIR-10A

(75) Inventors: Carlo M. Croce, Columbus, OH (US); Curtis C. Harris, Garrett Park, MD (US); Aaron J. Schetter, Silver Spring, MD (US)

(73) Assignees: The Ohio State University Research Foundation, Columbus, OH (US); The United States of America, as represented by the Secretary of the Department of Health and Human Services, National Institute of Health, Office of Technology Transfer, Washington, DC (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/296,500

(22) Filed: Nov. 15, 2011

(65) Prior Publication Data

US 2012/0058915 A1 Mar. 8, 2012

Related U.S. Application Data

(66) Division of application No. 12/373,358, filed as application No. PCT/US2007/015892 on Jul. 12, 2007, now Pat. No. 8,084,199, Substitute for application No. 60/807,304, filed on Jul. 13, 2006.

(60) Provisional application No. 60/932,736, filed on Jun. 1, 2007.

(51) Int. Cl.
*C12Q 1/68* (2006.01)
(52) U.S. Cl. .................................................. 435/6.14
(58) Field of Classification Search .................. 435/6.14
See application file for complete search history.

(56) References Cited

U.S. PATENT DOCUMENTS

| 7,888,010 B2 | 2/2011 | Brown et al. |
| 7,919,245 B2 | 4/2011 | Brown et al. |
| 2007/0092882 A1 | 4/2007 | Wang et al. |
| 2007/0213292 A1 | 9/2007 | Stoffel et al. |
| 2009/0131356 A1 | 5/2009 | Bader et al. |
| 2010/0099200 A1 | 4/2010 | Nazabal et al. |
| 2010/0104662 A1 | 4/2010 | Oren et al. |
| 2010/0196426 A1 | 8/2010 | Skog et al. |

FOREIGN PATENT DOCUMENTS

| CA | 2533701 A1 | 2/2005 |
| CA | 2587189 A1 | 12/2006 |
| FR | 2877350 A1 | 5/2006 |
| WO | 2005013901 A3 | 2/2005 |
| WO | 2005079397 A2 | 9/2005 |
| WO | 2005103298 A2 | 11/2005 |
| WO | 2006108718 A1 | 10/2006 |
| WO | 2007016548 A2 | 2/2007 |
| WO | 2007112754 A2 | 10/2007 |
| WO | 2008/036168 A2 | 3/2008 |
| WO | 2008073915 A2 | 6/2008 |

OTHER PUBLICATIONS

Australian Office Action, Application No. 2007205234 dated Sep. 20, 2011.
Australian Office Action, Application No. 2006291165 dated Feb. 13, 2012.
Australian Office Action, Application No. 2007205257 dated Dec. 22, 2011.
Australian Office Action, Application No. 2006291165 dated Aug. 23, 2011.
Canadian Office Action, Application No. 2,617,581, dated Apr. 2, 2012.
Canadian Office Action, Application No. 2,617,581, dated Feb. 1, 2011.
Canadian Office Action, Application No. 2,635,616, dated Feb. 27, 2011.
Canadian Office Action, Application No. 2,621,441, dated Feb. 1, 2011.
Chinese Office Action, Application No. 200680036598.3 dated Feb. 24, 2011.
Chinese Office Action, Application No. 200680039776.8 dated Jun. 30, 2011.
Chinese Office Action, Application No. 200780005821.2 dated Jan. 26, 2011.
Communication Concerning Office Action Received from Japanese Patent Office dated Jan. 30, 2012, Japanese Patent Application No. 2008-531200.
EP Search Report, Application No. 11196256.9 dated Feb. 28, 2012.
EP Search Report, Application No. 11196265.0 dated Mar. 5, 2012.
EP Search Report, Application No. 11196264-3 dated Feb. 28, 2012.
EP Search Report, Application No. 11196250.2 dated Apr. 24, 2012.
EP Search Report, Application No. 11196261.9 dated Feb. 28, 2012.
EP Search Report, Application No. 11196253.6 dated Apr. 24, 2012.
EP Search Report, Application No. 11196190.0 dated Apr. 24, 2012.
EP Search Report, Application No. 11196254.4 dated Feb. 28, 2012.
EP Search Report, Application No. 11196262.7 dated Feb. 28, 2012.
European Communication Pursuant to Article 94(3)EPC, Application No. 06814375.9 dated Oct. 14, 2011.
European Communication Pursuant to Article 94(3) EPC, Application No. 07716208.9, dated Sep. 13, 2011.
European Communication Pursuant to Article 94(3) EPC, Application No. 08768266.2, dated Apr. 18, 2011.

(Continued)

*Primary Examiner* — J. E. Angell
(74) *Attorney, Agent, or Firm* — MacMillan, Sobanski & Todd, LLC

(57) ABSTRACT

The present invention provides novel methods and compositions for the diagnosis and treatment of colon cancers. In particular, the present invention provides diagnostics and prognostics for colon (including colon adenocarcinoma) cancer patients, wherein the methods related to measuring miR levels can predict poor survival. The invention also provides methods of identifying inhibitors of tumorigenesis.

18 Claims, 25 Drawing Sheets
(24 of 25 Drawing Sheet(s) Filed in Color)

OTHER PUBLICATIONS

European Communication Pursuant to Article 94(3) EPC, Application No. 08767439.6, dated Feb. 12, 2011.
European Communication Pursuant to Article 94(3) EPC, Application No. 06800599.0 dated Nov. 25, 2011.
European Communication Pursuant to Article 94(3) EPC, Application No. 08767439.9, dated Mar. 15, 2011.
European Communication Pursuant to Article 94(3) EPC, Application No. 07867402.5, dated Jan. 5, 2011.
European Communication Pursuant to Article 94(3) EPC, Application No. 08799295.4, dated Nov. 18, 2011.
European Seach Report, Application No. 09714868.8 dated Aug. 1, 2011.
European Seach Report, Application No. 11151749.6, dated Feb. 8, 2011.
European Search Reoprt, Application No. 08841700.1, dated Jan. 4, 2011.
European Search Report, Application No. 09713926.5 dated Jul. 21, 2011.
European Search Report, Application No. 11151772-8, dated Feb. 8, 2011.
European Search Report, Application No. 11151769-4, dated Feb. 8, 2011.
European Search Report, Application No. 08713330.2, dated Jul. 22, 2011.
European Search Report, Application No. 08770974.4, dated Oct. 21, 2011.
European Search Report, Application No. 11151771-0, dated Feb. 8, 2011.
Japanese Office Action dated Jan. 4, 2012, Japanese Patent Application No. 2008-5251070.
Japanese Office Action dated Feb. 22, 2012, Japanese Patent Application No. 2008-549549.
Japanese Office Action dated Feb. 24, 2012, Japanese Patent Application No. 2008-549555.
Japanese Office Action dated Feb. 24, 2012, Japanese Patent Application No. 2008-549532.
PCT International Preliminary Report on Patentability, PCT/US2009/038214 filed Mar. 25, 2009, dated Jun. 16, 2011.
PCT International Preliminary Report on Patentability, PCT/US2009/065072 filed Nov. 19, 2009, dated Jun. 3, 2011.
PCT International Preliminary Report on Patentability, PCT/US2010/025173 filed Feb. 24, 2010, dated Sep. 9, 2011.
PCT International Search Report and the Written Opinion, PCT/US2012/020911 filed Jan. 11, 2012, dated Apr. 25, 2012.
Aiba, M. "Pathology of the Breast Carcinoma from the Viewpoint of the Proliferative Activity and Grade of Malignancy," JP J Cancer Clin, 2000, pp. 475-181, vol. 46, No. 5.
Alvarez-Secord, A. et al., "Maspin Expression in Epithelial Ovarian Cancer and Associations with Poor Prognosis: A Gynecologic Oncology Group Study," Gynecologic Oncology, 2006, pp. 390-397, vol. 101.
Braun et al., "p53-Responsive MicroRNAs 192 and 215 are Capable of Inducing Cell Cycle Arrest," Cancer Research, 2008, pp. 10094-10104, vol. 68.
Cannistra, S.A., "Cancer of the Ovary," The New England Journal of Medicine, 2004, pp. 2519-2529, vol. 351, No. 25.
Castoldi, M. et al., "A Sensitive Array for MicroRNA Expression Profiling (miChip) Based on Locked Nucleic Acids (LNA)," RNA, 2006, pp. 913-920, vol. 12.
Chim, S.S.C. et al., "Detection and Characterization of Placental MicroRNAs in Maternal Plasma," Clinical Chemistry, 2008, pp. 482-490, vol. 54, No. 3.
Debernardi, S. et al., "MicroRNA miR-181a Correlates with Morphological Sub-Class of Acute Myeloid Leukemia and the Expression of its Target Genes in Global Genome-Wide Analysis," Leukemia, 2007, pp. 912-916, vol. 21.
Feng, G. et al., "Elevated Serum-Circulating RNA in Patients with Conventional Renal Cell Cancer," Anticancer Research, 2008, pp. 321-326, vol. 28.

Fujuta, S. et al., "miR-21 Gene Expression Triggered by AP-1 is Sustained Through a Double-Negative Feedback Mechanism," J. Mol. Biol., Abstract, 2008, pp. 492-504, vol. 378.
Gang, M. et al., "Expression of Programmed Cell Death 4 and Its Clinicopathological Significance in Human Pancreatic Cancer," Abstract, 2005, pp. 597-600, vol. 27.
He, L. et al., "A MicroRNA Polycistron as a Potential Human Oncogene," Nature, Jun. 2005, pp. 828-833, vol. 435.
Ishii, H. et al., "Effect of Adenoviral Transduction of the Fragile Histidine Triad Gene into Esophageal Cancer Cells," Cancer Research, Feb. 2001, pp. 1578-1584, vol. 61.
Jacobs, I.J. et al., "Progress and Challenges in Screening for Early Detection of Ovarian Cancer," Molecular & Cellular Proteomics, 2004, pp. 355-366, vol. 3.
Jacobs, I.J. et al., "Prevalence Screening for Ovarian Cancer in Postmenopausal Women by CA 125 Measurement and Ultrasonography," BMJ, Apr. 1993, pp. 1030-1034, vol. 306.
Jazbutyte, V. et al., "MicroNRA-21: From Cancer to Cardiovascular Disease," Current Drug Targets, Abstract, 2010, pp. 926-935, vol. 11.
Jemal, A. et al., "Cancer Statistics, 2008," CA Cancer J. Clin., 2008, pp. 71-96, vol. 58, No. 2.
Landgraf, P. et al., "A Mammalian MicroRNA Expression Atlas Based on Small RNA Library Sequencing," Cell, Jun. 2007, pp. 1401-1414, vol. 129.
Lawrie, C.H. et al., "Detection of Elevated Levels of Tumour-Associated MicroRNAs in Serum of Patients with Diffuse Large B-Cell Lymphoma," British Journal of Haematology, 2008, pp. 672-675, vol. 141.
Li, Z. et al., "Inhibition of PRL-3 Gene Expression in Gastric Cancer Cell Line SGC7901 via MicroRNA Suppressed Reduces Peritoneal Metastasis," Biochemical and Biophysical Research, Sep. 2006, pp. 229-237, vol. 348, No. 1.
Mendell, J.T., "miRiad Roles for the miR-17-92 Cluster in Development and Disease," Cell, 2008, pp. 217-.
Meng, F. et al., "MicroRNA-21 Regulates Expression of the PTEN Tumor Suppressor Gene in Human Hepatocellular Cancer," Gastroenterology, 2007, pp. 647-658, vol. 133.
Nakajima, G. et al., "Non-Coding MicroRNAs HAS-LET-7G and HAS-MIR-181b are Associated with Chemoresponse to S-1 in Colon Cancer," Cancer Genomics & Proteomics, Sep. 2006, pp. 317-324, vol. 3, No. 5.
Nam, E.J. et al., "MicroRNA Expression Profiles in Serous Ovarian Carcinoma," Clinical Cancer Research, 2008, pp. 2690-2695, vol. 14, No. 9.
Olivier, R.I. et al., "CA125 and Transvaginal Ultrasound Monitoring in High-Risk Women Cannot Prevent the Diagnosis of Advanced Ovarian Cancer," Gynecologic Oncology, 2006, pp. 20-26, vol. 100.
Petrocca, F. et al., "MicroRNAs Deregulation in Gastric Cancer," PNAS, Apr. 2006, p. 1338, vol. 47, Abstract # 5690.
Pichiorri et al., "Downregulation of p53-Inducible MicroRNAs 192, 194 and 215 Impairs the p53/MDM2 Autoregulatory Loop in Multiple Myeloma Development," Cancer Cell, 2010, pp. 367-381, vol. 18.
Ribas, J. et al., "The Transcriptional Regulation of miR-21, Its Multiple Transcripts, and Their Implication in Prostate Cancer," Cell Cycle, 2010, pp. 923-929, vol. 9.
Rossi, S. et al., "MicroRNA Fingerprinting of CLL Patients with Chromosome 17p Deletion Identify a miR-21 Score that Stratifies Early Survival," Blood, Aug. 2010, pp. 945-952, vol. 116, No. 6.
Ryu, J.K. et al., "Aberrant MicroRNA-155 Expression is an Early Event in the Multistep Progression of Pancreatic Adenocarcinoma," Pancreatology, 2010, pp. 66-73, vol. 10.
Saito, Y. et al., "Specific Activation of MicroRNA-127 with Downregulation of the Proto-Oncogene BCL6 by Chromatin-Modifying Drugs in Human Cancer Cells," Cancer Cell, Jun. 2006, pp. 435-443, vol. 9.
Schagen, F. et al., "Genetic Targeting of Adenovirus Vectors Using a Reovirus Sigmal-Based Attachment Protein," Molecular Therapy, May 2006, pp. 997-1005, vol. 13, No. 5.
Stamatopoulos, B. et al., "MicroRNA-29c and MicroRNA-233 Down-Regulation has In Vivo Significance in Chronic Lymphocytic Leukemia and Improves Disease Risk Stratification," Blood, May 2009, pp. 5237-5245, vol. 113, No. 21.

Taylor, D.D. et al., "MicroRNA Signatures of Tumor-Derived Exosomes as Diagnostic Biomarkers of Ovarian Cancer," Gynecologic Oncology, 2008, pp. 13-21, vol. 110.
Thomson, M., Supplementary data for "A Custon Microarray Platform for Analysis of MicroRNA Gene Expression," Nature Methods, Oct. 2004, pp. 47-53, vol. 1, No. 1.
Tilt, E. et al., "Expression and Function of Micro RNAs in Immune Cells During Normal or Disease State," International Journal of Medicine Sciences, 2008, pp. 73-79, vol. 5, No. 2.
Uil, T.G. et al., "Generation of an Adenoviral Vector Containing an Addition of a Heterologous Ligand to the Serotpe 3 Fiber Knob," Cancer Gene Therapy, Feb. 2003, pp. 121-124, vol. 10, No. 2.
Vassilev et al., "In Vivo Activation of the p53 Pathway by Small-Molecule Antagonists of MDM2," Science, 2004, pp. 844-848, vol. 303.
Verschuur, A.C., "Acute Megakaryoblastic Leukemia," May 2004, pp. 1-5, Retrieved from the Internet: URL: http://www.orpga.net/data/patho/GB/uk-AMLM7.pdf.
Watson, D.I. et al., "MicroRNA Expression Profiles in Barrett's Oesophagus," RACS Annual Scientific Congress, 2007, pp. A45, vol. 77.
Wiemer et al., "The Role of MicroRNAs in Cancer: No Small Matter," European Journal of Cancer, Jun. 12, 2007, vol. 43, No. 10, pp. 1529-1544.
Xi, Y. et al., "Prognostic Values of MicroRNAs in Colorectal Cancer," Biomarker Insights, Jan. 2006, pp. 113-121, vol. 1.
Zawacka-Pankau, J. et al., "Expression and Simple, One-Step Purification of Fragile Histidine Triad (Fhit) Tumor Suppressor Mutant Forms in Escherichia coli and their Interaction with Protoporphyrin IX," Biotechnology Letters, Jun. 2007, pp. 877-883, vol. 29, No. 6.
Zhao et al., "p53 Mediates the Negative Regulation of MDM2 by Orphan Receptor TR3," The EMBO Journal, 2006, pp. 5703-5715, vol. 25.
EP Search Report, Application No. 12165638.3 dated Jun. 12, 2012.
EP Search Report, Application No. 12165636.7 dated Jun. 8, 2012.
Australian Government, Examiner's First Report, Appln. No. 2007243475, Dated Mar. 30, 2012.
Australian Office Action, Application No. 2007227423 dated Apr. 13, 2012.
Chinese Office Action, Application No. 200880119920639 dated May 3, 2012.
Chinese Office Action, Application No. 200780033066.9 dated Jun. 26, 2012.
Chinese Office Action, Application No. 200880112585.9 dated May 24, 2012.
EP Search Report, Application No. 12154298.9 dated Jun. 4, 2012.
European Communication Pursuant to Article 94(3) EPC, Application No. 08841700.1, dated Jun. 1, 2012.
European Communication Pursuant to Article 94(3) EPC, Application No. 07867402.5, dated Apr. 10, 2012.
European Communication Pursuant to Article 94(3) EPC, Application No. 07717903.4, dated Apr. 25, 2012.
PCT International Preliminary Report on Patentability, PCT/US2010/057758 filed Nov. 23, 2010, dated Jun. 7, 2012.
PCT Invitation to Pay Additional Fees, PCT/US2012/028016 filed Mar. 7, 2012, dated May 29, 2012.

Eiriksdottir, G. et al., "Mapping Loss of Heterozygosity at Chromosome 13q: Loss at 13q12-q13 is Associated wit Breast Tumour Progression and Poor Prognosis," European Journal of Cancer, 1998, pp. 2076-2081, vol. 34, No. 13.
Gailiun, M., "Single MicroRNA Causes Cancer in Transgenic Mice," Research Communications, The Ohio State University, Apr. 2006.
Garofalo, M. et al., "MicroRNA Signatures of TRAIL Resistance in Human Non-Small Cell Lung Cancer," Oncogene, 2007, pp. 3854-3855, vol. 27.
Mazurek, N. et al., "Phosphorylated Galectin-3 Mediates Tumor Necrosis Factor-Related Apoptosis-Inducing Ligand Signaling by Regulating Phosphatase and Tensin Homologue Deleted on Chromosome 10 in Human Breast Carcinoma Cells," The Journal of Biological Chemistry, Jul. 2007, pp. 21337-21348, vol. 282, No. 29.
Okada, H. et al., "MicroRNAs in Immune Regulation—Opportunities for Cancer Immunotherapy," The International Journal of Biochemistry & Cell Biology, 2010, pp. 1256-1261, vol. 42.
Australian Office Action, Application No. 2007346101 dated Jun. 21, 2012.
Australian Office Action, Application No. 2008248319 dated Jul. 12, 2012.
Australian Office Action, Application No. 2008266014 dated Jul. 6, 2012.
Australian Office Action, Application No. 2007272947 dated May 21, 2012.
Chinese Office Action, Application No. 200880116343.7 dated Jan. 31, 2011.
EP Search Report, Application No. 09715356.3 dated Jul. 12, 2012.
EP Search Report, Application No. 12154342.5 dated Jul. 6, 2012.
EP Search Report, Application No. 12154321.9 dated Jul. 20, 2012.
EP Search Report, Application No. 12154304.5 dated Jun. 26, 2012.
PCT International Search Report and the Written Opinion, PCT/US2012/28016 filed Mar. 7, 2012, dated Aug. 3, 2012.
Butz, H. et al., "Down-Regulation of Wee1 Kinase by a Specific Subset of MicroRNA Sporadic Pituitary Adenomas," Journal of Clinical Endocrinol Metab, Oct. 2010, pp. E181-E191, vol. 95, No. 10.
Lawrie, C. H. "MicroRNAs and Haematology: Small Molecules, Big Function," British Journal of Haematology, Jun. 2007, pp. 503-512, vol. 137, No. 6.
Lawrie, C.H., "MicroRNA, Expression in Lymphoma," Expert Opinoin on Biological Therapy, Sep. 2007, pp. 1363-1374, vol. 7, No. 9.
Lee, Y.S. et al., "MicroRNAs: Small but Potent Onogenes or Tumor Suppressors," Current Opinion in Investigational Drugs, Jun. 2006, pp. 560-564, vol. 7, No. 6.
Martin, M. et al., "MicroRNA-155 Regulates Human Angiotensin II Type 1 Receptor Expression in Fibroblasts," The Journal of Biological Chemistry, Jul. 2006, pp. 18277-18284, vol. 281, No. 27.
O'Connell, R. et al., "Inositol Phosphatase SHIP1 is a Primary Target of miR-155," PNAS, Apr. 2009, pp. 7113-7118, vol. 106, No. 17.
Williams, C.S., "OncomiRs: The Discovery and Progress of MicroRNAs in Cancers," Molecular Cancer, Sep. 2007, pp. 259-269, vol. 6, No. 4.

METHOD OF DIAGNOSING POOR SURVIVAL PROGNOSIS COLON CANCER USING MIR-10A

CROSS-REFERENCE TO RELATED APPLICATIONS

This application is a divisional application of Ser. No. 12/373,358 having a 37 CFR §1.371 filing date of Feb. 11, 2009, which claims priority to PCT/US2007/015892 filed Jul. 12, 2007, which the benefit of U.S. Provisional Application Ser. No. 60/807,304 filed Jul. 13, 2006 and Ser. No. 60/932,736 filed Jun. 1, 2007, the disclosures of which are incorporated herein by reference.

STATEMENT REGARDING FEDERALLY SPONSORED RESEARCH

This invention was made with government support under Grant No. PO1-CA76259 and No. PO1-CA81534 awarded by the National Cancer Institute. The government has certain rights in the invention.

BACKGROUND OF THE INVENTION

Colon adenocarcinoma is a major cause of cancer mortality worldwide. Colorectal cancer is the third most common and second leading cause of cancer death in the United States. Sporadic colon adenocarcinomas initiate as adenomas and evolve through a progression of molecular, cellular and histologic changes. While five-year mortality rates have modestly declined over the last three decades, there is still a need to identify new prognostic biomarkers and therapeutic targets for this disease. Currently, chemotherapy has significant therapeutic value but surgery is the only curative form of treatment.

Ideal therapeutic targets should be causally associated with disease and amenable to designing therapeutic interventions; whereas ideal biomarkers should be easy to measure and have strong associations with clinical outcomes. MicroRNAs could match both criteria.

MicroRNAs are 18-25 nucleotide, non-coding RNA molecules that regulate the translation of many genes. Since their discovery, they have been found to regulate a variety of cellular processes including apoptosis, differentiation and cell proliferation. MicroRNAs may also have a causal role in carcinogenesis. MicroRNA expression levels are altered in most tumor types, including colon tumors. The microRNAs miR-15 and miR-16a are deleted or downregulated in the majority of chronic lymphocytic leukemias. Experimental manipulation of specific microRNAs modulates tumor development in mouse model systems. The prognostic potential of microRNAs has also been demonstrated for chronic lymphocytic leukemia, lung cancer[8] and neuroblastomas. Aberrant microRNAs expression may be causal to carcinogenesis, inhibiting specific microRNAs may have therapeutic implications. Modified antisense oligonucleotides can be designed to specifically inhibit microRNA function. Antagomirs are one type of antisense oligonucleotide that has proven effective at inhibiting microRNA function in vivo in mice.

SUMMARY OF THE INVENTION

In one broad aspect, there is provided herein a method of diagnosing whether a subject has, is at risk for developing, or has a decrease survival prognosis for, a colon cancer-related disease. The method includes measuring the level of at least one miR gene product in a test sample from the subject, wherein an alteration in the level of the miR gene product in the test sample, relative to the level of a corresponding miR gene product in a control sample, is indicative of the subject either having, or being at risk for developing, the colon cancer-related disease. In a particular aspect, the at least one miR gene product is selected from the group consisting of miR-20a, miR-21, miR-106a, miR-181b, miR-203 and combinations thereof. In one embodiment, the one miR gene product is miR-21.

In another broad aspect, there is provided herein a method of testing for at least an initiation of, predisposition to, or decreased survival prognosis for, a colon cancer-related disease response, which comprises:

(1) determining an expression level of at least one marker in a sample from a test subject; the at least one marker including at least one miR gene product selected from the group consisting of miR-20a, miR-21, miR-106a, miR-181b, miR-203 and combinations thereof;

(2) comparing the expression level determined in step (1) with a control expression level of the marker in a sample from a healthy subject; and (3) judging the subject to have a colon cancer-related disease when the result of the comparison in step (2) indicates that: i) the expression level of the at least marker in the test subject is higher than that in the control, or ii) the expression level of the at least one marker in the test subject is lower than that in the control.

The sample can comprise one or more of tissue, blood, plasma, serum, urine, and feces. Also, all method steps can be performed in vitro.

In another broad aspect, there is provided herein a method of diagnosing whether a subject has, is at risk for developing, or has a decrease survival prognosis for, a colon cancer-related disease, comprising:

(1) reverse transcribing RNA from a test sample obtained from the subject to provide a set of target oligodeoxynucleotides;

(2) hybridizing the target oligodeoxynucleotides to a microarray comprising miRNA-specific probe oligonucleotides to provide a hybridization profile for the test sample; and (3) comparing the test sample hybridization profile to a hybridization profile generated from a control sample, wherein an alteration in the signal of at least one miRNA is indicative of the subject either having, being at risk for developing, or having a decreased survival prognosis for, a colon cancer-related disease.

In a particular aspect, the signal of at least one miRNA, relative to the signal generated from the control sample, is up- or down-regulated. Also, the microarray can comprise miRNA-specific probe oligonucleotides for one or more miRNAs selected from the group consisting of miR-20a, miR-21, miR-106a, miR-181b, miR-203 and combinations thereof.

In another broad aspect, there is provided herein a method of inhibiting tumorigenesis in a subject who has, or is suspected of having, a colon cancer-related disease in which at least one miR gene product selected from the group consisting of miR-20a, miR-21, miR-106a, miR-181b, miR-203 and combinations thereof, is down-regulated or up-regulated in the cancer cells of the subject, relative to control cells, comprising:

(1) when the at least one miR gene product is down-regulated in the cancer cells, administering to the subject an effective amount of at least one isolated miR gene product selected from the group consisting of miR-20a, miR-21, miR-106a, miR-181b, miR-203 and combinations thereof, such that tumorigenesis is inhibited in the subject; or (2) when the at least one miR gene product is up-regulated in the cancer cells, administering to the subject an effective amount of at least one compound for inhibiting expression of the at least one miR gene product selected from the group consisting of miR-20a, miR-21, miR-106a, miR-181b, miR-203 and combinations thereof, such that tumorigenesis is inhibited in the subject.

In a particular aspect, at least one isolated miR gene product in step (1) and/or in step (2) is miR-21 or an isolated variant or biologically-active fragment or functional equivalent thereof, or an antibody that binds thereto.

In another broad aspect, there is provided herein a method of inhibiting tumorigenesis in a subject who has a colon cancer, comprising:

(1) determining the amount of at least one miR gene product in cancer cells from the subject, relative to control cells; and (2) altering the amount of miR gene product expressed in the cancer cells by:
  (i) administering to the subject an effective amount of at least one isolated miR gene product selected from the group consisting of miR-20a, miR-21, miR-106a, miR-181b, miR-203 and combinations thereof, if the amount of the miR gene product expressed in the cancer cells is less than the amount of the miR gene product expressed in control cells; or
  (ii) administering to the subject an effective amount of at least one compound for inhibiting expression of the at least one miR gene product, if the amount of the miR gene product expressed in the cancer cells is greater than the amount of the miR gene product expressed in control cells, such that tumorigenesis is inhibited in the subject.

In a particular aspect, the at least one isolated miR gene product in step (i) is miR-21 or an isolated variant or biologically-active fragment thereof. Also, in certain embodiments, the at least one miR gene product in step (ii) is selected from the group consisting of miR-20a, miR-21, miR-106a, miR-181b, miR-203 and combinations thereof, or an isolated variant or biologically-active fragment thereof.

In another broad aspect, there is provided herein a method of identifying an inhibitor of tumorigenesis, comprising providing a test agent to a cell and measuring the level of at least one miR gene product associated with an altered expression levels in a colon cancer-related disease, wherein an increase or decrease in the level of the miR gene product in the cell, relative to a suitable control cell, is indicative of the test agent being an inhibitor of tumorigenesis.

In another broad aspect, there is provided herein a method of identifying an inhibitor of tumorigenesis, comprising providing a test agent to a cell and measuring the level of at least one miR gene product associated with an altered expression level in a colon cancer-related disease, wherein a decrease in the level of the miR gene product in the cell, relative to a suitable control cell, is indicative of the test agent being an inhibitor of tumorigenesis.

In another broad aspect, there is provided herein a marker for assessing one or more metabolic pathways that contribute to at least one of initiation, progression, severity, pathology, aggressiveness, grade, activity, disability, mortality, morbidity, disease sub-classification or other underlying pathogenic or pathological feature of at least one colon cancer-related disease, wherein the marker comprises one or more miR gene products selected from the group consisting of miR-20a, miR-21, miR-106a, miR-181b, miR-203 and combinations thereof.

In another broad aspect, there is provided herein a composition comprising one or more of the markers described herein.

In another broad aspect, there is provided herein a method of identifying a potential for the initiation or development of at least one colon cancer-related disease in a subject, the method providing measuring one or more of the markers described herein. In certain embodiments, one or more markers are present in an isolated sample and all method steps are performed in vitro.

In another broad aspect, there is provided herein a reagent for testing for a colon cancer-related disease, wherein the reagent comprises a polynucleotide comprising the nucleotide sequence of at least one marker described herein or a nucleotide sequence complementary to the nucleotide sequence of the marker.

In another broad aspect, there is provided herein a reagent for testing for a colon cancer-related disease, wherein the reagent comprises an antibody that recognizes a protein encoded by at least one marker described herein.

In another broad aspect, there is provided herein a DNA chip for testing for a colon cancer-related disease, on which a probe has been immobilized to assay at least one marker described herein.

In another broad aspect, there is provided herein a method of assessing the effectiveness of a therapy to prevent, diagnose and/or treat at least one colon cancer-related disease comprising:

1) subjecting an animal to a therapy whose effectiveness is being assessed, and 2) determining the level of effectiveness of the treatment being tested in treating or preventing the colon cancer-related disease by evaluating at least one marker described herein.

In certain embodiments, the candidate therapeutic agent comprises one or more of: pharmaceutical compositions, nutraceutical compositions, and homeopathic compositions. Also, the therapy being assessed can be for use in a human subject. In certain embodiments, the method is not a method of treatment of the human or animal body by surgery or therapy.

In another broad aspect, there is provided herein a method of assessing the potential of at least one material for an ability to initiate a colon cancer-related disease response in an animal model, the method providing:

1) measuring one or more of up- or down-regulated markers described herein after exposure of the animal to one or more materials in amounts sufficient to initiate a colon cancer-related disease response in the animal; and 2) determining whether at least one of the up- or down-regulated markers has the ability to initiate a colon cancer-related disease response.

In another broad aspect, there is provided herein a pharmaceutical composition for treating a colon cancer-related disease, comprising: at least one miR gene product selected from the group consisting of miR-20a, miR-21, miR-106a, miR-181b, miR-203 and combinations thereof; and, a pharmaceutically-acceptable carrier.

In another broad aspect, there is provided herein a pharmaceutical composition for treating a colon cancer, comprising at least one miR expression-inhibition compound and a pharmaceutically-acceptable carrier, wherein the at least one miR expression-inhibition compound is specific for a miR gene product selected from the group consisting of miR-20a, miR-21, miR-106a, miR-181b, miR-203 and combinations thereof.

In another broad aspect, there is provided herein an article of manufacture comprising: at least one capture reagent that binds to a marker for a colon cancer-related disease selected from at least one of the markers described herein.

In another broad aspect, there is provided herein a kit for screening for a candidate compound for a therapeutic agent to treat a colon cancer-related disease, wherein the kit comprises: one or more reagents of at least one marker described herein, and a cell expressing at least one marker. In certain embodiments, the presence of the marker is detected using a reagent comprising an antibody or an antibody fragment which specifically binds with at least one marker. Also, in certain embodiments, the reagent is labeled, radio-labeled, or biotin-labeled, and/or the antibody or antibody fragment is radio-labeled, chromophore-labeled, fluorophore-labeled, or enzyme-labeled. In a particular embodiment, the kit further includes a container comprising at least one of the markers. Also, the reagent can comprise one or more of: an antibody, a probe to which the reagent is attached or is attachable, and an immobilized metal chelate.

In another broad aspect, there is provided herein a screening test for a colon cancer-related disease comprising: contacting one or more of the markers with a substrate for such marker and with a test agent, and determining whether the test agent modulates the activity of the marker.

In certain embodiments, all method steps can be performed in vitro.

In another broad aspect, there is provided herein a microarray for predicting the presence of a colon cancer-related disease in a subject comprising an antibody directed to at least one marker.

In another broad aspect, there is provided herein methods, compositions and the like, where a level of expression of the marker is assessed by detecting the presence of a transcribed polynucleotide or portion thereof, wherein the transcribed polynucleotide comprises a coding region of the marker. Also, the sample can be a colon cancer-associated body fluid or tissue. In a particular embodiment, the sample comprises cells obtained from the patient.

In another broad aspect, there is provided herein a method for treating, preventing, reversing or limiting the severity of a colon cancer-related disease complication in an individual in need thereof, comprising: administering to the individual an agent that interferes with at least one colon cancer-related disease response signaling pathway, in an amount sufficient to interfere with such signaling, wherein the agent comprises at least one miR gene product selected from the group consisting of miR-20a, miR-21, miR-106a, miR-181b, miR-203 and combinations thereof.

In another broad aspect, there is provided herein the use of an agent that interferes with at least one colon cancer-related disease response signaling pathway, for the manufacture of a medicament for treating, preventing, reversing or limiting the severity of a colon cancer-related disease complication in an individual, wherein the agent comprises at least one miR gene product selected from the group consisting of miR-20a, miR-21, miR-106a, miR-181b, miR-203 and combinations thereof.

In another broad aspect, there is provided herein a method of treating, preventing, reversing or limiting the severity of a colon cancer-related disease complication in an individual in need thereof, comprising administering to the individual an agent that interferes with at least one colon cancer-related disease response cascade, wherein the agent comprises at least one miR gene product selected from the group consisting of miR-20a, miR-21, miR-106a, miR-181b, miR-203 and combinations thereof.

In another broad aspect, there is provided herein the use of an agent that interferes with at least one colon cancer-related disease response cascade, for the manufacture of a medicament for treating, preventing, reversing or limiting the severity of a colon cancer-related disease complication in an individual, wherein the agent comprises at least one miR gene product selected from the group consisting of miR-20a, miR-21, miR-106a, miR-181b, miR-203 and combinations thereof.

In another broad aspect, there is provided herein a computer-readable medium comprising a database having a plurality of digitally-encoded reference profiles, wherein at least a first reference profile represents a level of at least a first marker in one or more samples from one or more subjects exhibiting an indicia of a colon cancer-related disease response, wherein the marker comprises one or more miR gene products selected from the group consisting of miR-20a, miR-21, miR-106a, miR-181b, miR-203 and combinations thereof.

In certain embodiments, the computer readable medium includes at least a second reference profile that represents a level of at least a second marker in one or more samples from one or more subjects exhibiting indicia of a colon cancer-related disease response; or subjects having a colon cancer-related disease.

In another broad aspect, there is provided herein a computer system for determining whether a subject has, is predisposed to having, or has a poor survival prognosis for, a colon cancer-related disease, comprising the database described herein, and a server comprising a computer-executable code for causing the computer to receive a profile of a subject, identify from the database a matching reference profile that is diagnostically relevant to the subject profile, and generate an indication of whether the subject has, or is predisposed to having, a colon cancer-related disease.

In another broad aspect, there is provided herein a computer-assisted method for evaluating the presence, absence, nature or extent of a colon cancer-related disease in a subject, comprising:

1) providing a computer comprising a model or algorithm for classifying data from a sample obtained from the subject, wherein the classification includes analyzing the data for the presence, absence or amount of at least one marker, wherein the marker comprises one or more miR gene products selected from the group consisting of miR-20a, miR-21, miR-106a, miR-181b, miR-203 and combinations thereof;

2) inputting data from the biological sample obtained from the subject; and, 3) classifying the biological sample to indicate the presence, absence, nature or extent of a colon cancer-related disease.

In another broad aspect, at least one miR gene product and combinations thereof includes isolated variants or biologically-active fragments.

In another broad aspect, there is provided herein an animal model for colon cancer wherein at least one of the following biological or chemical processes occurs in the animal model up- or down regulation of one or more miR gene products is selected from the group consisting of miR-20a, miR-21, miR-106a, miR-181b, miR-203 and combinations thereof. In certain embodiments, the animal model is a nonhuman vertebrate. In particular embodiments, the animal model is a mouse, rat, rabbit, or primate.

Various objects and advantages of this invention will become apparent to those skilled in the art from the following detailed description of the preferred embodiment, when read in light of the accompanying drawings.

BRIEF DESCRIPTION OF THE DRAWINGS

The patent or application file contains at least one drawing executed in color. Copies of this patent or patent application publication with color drawings will be provided by the Office upon request and payment of the necessary fee.

(FIG. 1a) In situ hybridization for miR-21 was optimized to distinguish high and low expression of miR-21. Colonic epithelial cells in human tumor (T) express higher levels of miR-21 compared to adjacent nontumorous tissue (N). (FIG. 1c) Nuclei and cytoplasm of colonic epithelial cells in tumor tissue express significant amounts of miR-21 in tumor tissue, at high magnification. (FIG. 1e) Non-tumor tissue shows no significant expression of miR-21 at the same magnification.

(FIG. 1b, FIG. 1d, FIG. 1f) The scramble control probe shows no significant staining at low or high magnification in serial sections of tumor and non-tumor tissue, as expected. Scale bars (FIGS. 1c-f) indicate 500 μM (g) miR-21 is expressed at higher levels in more advanced tumors. Dot plots represent miR-21 relative Ct values (from quantitative RT-PCR) for adenoma and tumor expression levels that have been normalized to paired non-adenoma or nontumorous tissue, respectively. Tissue types have been ordered from adenoma to stage I-IV tumors. Bars indicate median value. There is a significant trend that more advanced tumors have higher expression of miR-21 (nonparametric test for trend across ordered groups).

(FIG. 3a) MicroRNA microarrays were used in the Maryland test cohort to measure microRNA expression levels of tumors and nontumorous tissues. Tissues with undetectable expression of miR-21 based on microarray data were excluded. High miR-21 expression was classified based on highest tertile. Red lines indicate individuals with high expression while green lines correspond to low expression. For nontumorous tissue, 24/69 tissues were classified as high while 26/72 tumors were classified as high. High miR-21 expression in tumors (right) is associated with poor survival while it is not associated in nontumorous tissue.

(FIG. 3b) Validation of the association with high miR-21 expression in tumors and poor prognosis in an independent cohort. Expression levels of miR-21 were measured by quantitative RT-PCR. High expression is based on the highest tertile. 35/103 nontumorous tissues were classified as high and 34/103 tumor tissues were classified as high. P-values are log rank p-values from Kaplan-Meier analysis. X's on all lines indicate the time at which an individual was censored.

(FIG. 4a) MicroRNA microarrays were used in the Maryland test cohort to measure microRNA expression levels of tumors and nontumorous tissues. Tissues with undetectable expression of miR-21 based on microarray data were excluded. High miR21 expression was classified based on highest tertile. Red lines indicate individuals with high expression while green lines correspond to low expression. For nontumorous tissue, 26/74 tissues were classified as high while 28/79 tumors were classified as high. High miR-21 expression in tumors (right) is associated with poor survival while it is not associated in nontumorous tissue.

(FIG. 4b) Validation of the association with high miR-21 expression in tumors and poor prognosis in an independent cohort. Expression levels of miR-21 were measured by quantitative RT-PCR. High expression is based on the highest tertile. 37/111 nontumorous tissues were classified as high and 37/111 tumor tissues were classified as high. All p-values are log rank p-values from Kaplan-Meier analysis. X's on all lines indicate the time at which an individual was censored.

(FIG. 5a) Comparison of survival rates for TNM stage II/III subjects with conventional adenocarcinoma histology by miR-21 expression levels and receipt of adjuvant chemotherapy. For the 77 stage II/III subjects, 25 were classified as low miR-21 receiving therapy, 28 as low miR-21 and not receiving therapy, 11 as high miR-21 receiving therapy, and 13 as high miR-21 and not receiving therapy. For stage II/III subjects who received adjuvant chemotherapy, high miR-21 expression in tumors is associated with a poor survival (p=0.03).

(FIG. 5b) Comparison of TNM stage II subjects with conventional adenocarcinoma histology. For the 33 stage II subjects, 8 were classified as low miR-21 receiving therapy, 15 as low miR-21 and not receiving therapy, 3 as high miR-21 receiving therapy, and 7 as high miR-21 and not receiving therapy. All stage II subjects who received chemotherapy survived for the duration of this study.

(FIG. 5c) Comparison of TNM stage III subjects with conventional adenocarcinoma histology. For the 44 stage III subjects, 17 were classified as low miR-21 receiving therapy, 13 as low miR-21 and not receiving therapy, 8 as high miR-21 receiving therapy, and 6 as high miR-21 and not receiving therapy. For stage III subjects who received adjuvant chemotherapy, high miR-21 expression in tumors is associated with a poor survival (p=0.02). X's on all lines indicate the time at which an individual was censored.

(FIG. 6a) All TNM stage II/III subjects. For the 119 stage II/III subjects, 40 were classified as low miR-21 receiving therapy, 41 as low miR-21 and not receiving therapy, 16 as high miR-21 receiving therapy, and 22 as high miR-21 and not receiving therapy. High miR-21 expression is associated with a poor survival for those who receive chemotherapy (p=0.003) as well as those who do not receive therapy (p=0.04).

(FIG. 6b) All TNM stage II subjects. For the 52 stage II/III subjects, 10 were classified as low miR-21 receiving therapy, 25 as low miR-21 and not receiving therapy, 4 as high miR-21 receiving therapy, and 13 as high miR-21 and not receiving therapy. Associations between high miR-21 expression and prognosis was not statistically significant in individuals who received chemotherapy (p=0.11) or those who did not receive chemotherapy (p=0.06).

(FIG. 6c) All TNM stage III subjects. For the 67 stage III subjects, 30 were classified as low miR-21 receiving therapy, 16 as low miR-21 and not receiving therapy, 12 as high miR-21 receiving therapy, and 9 as high miR-21 and not receiving therapy. High miR-21 expression is significantly associated with poor survival in stage III subjects who received chemotherapy (p=0.007), but not in subjects who did not receive chemotherapy (p=0.30). X's on all lines indicate the time at which an individual was censored.

DETAILED DESCRIPTION OF THE PREFERRED EMBODIMENT

Figures 1A, 1B, 1C, 1D, 1E, 1F:
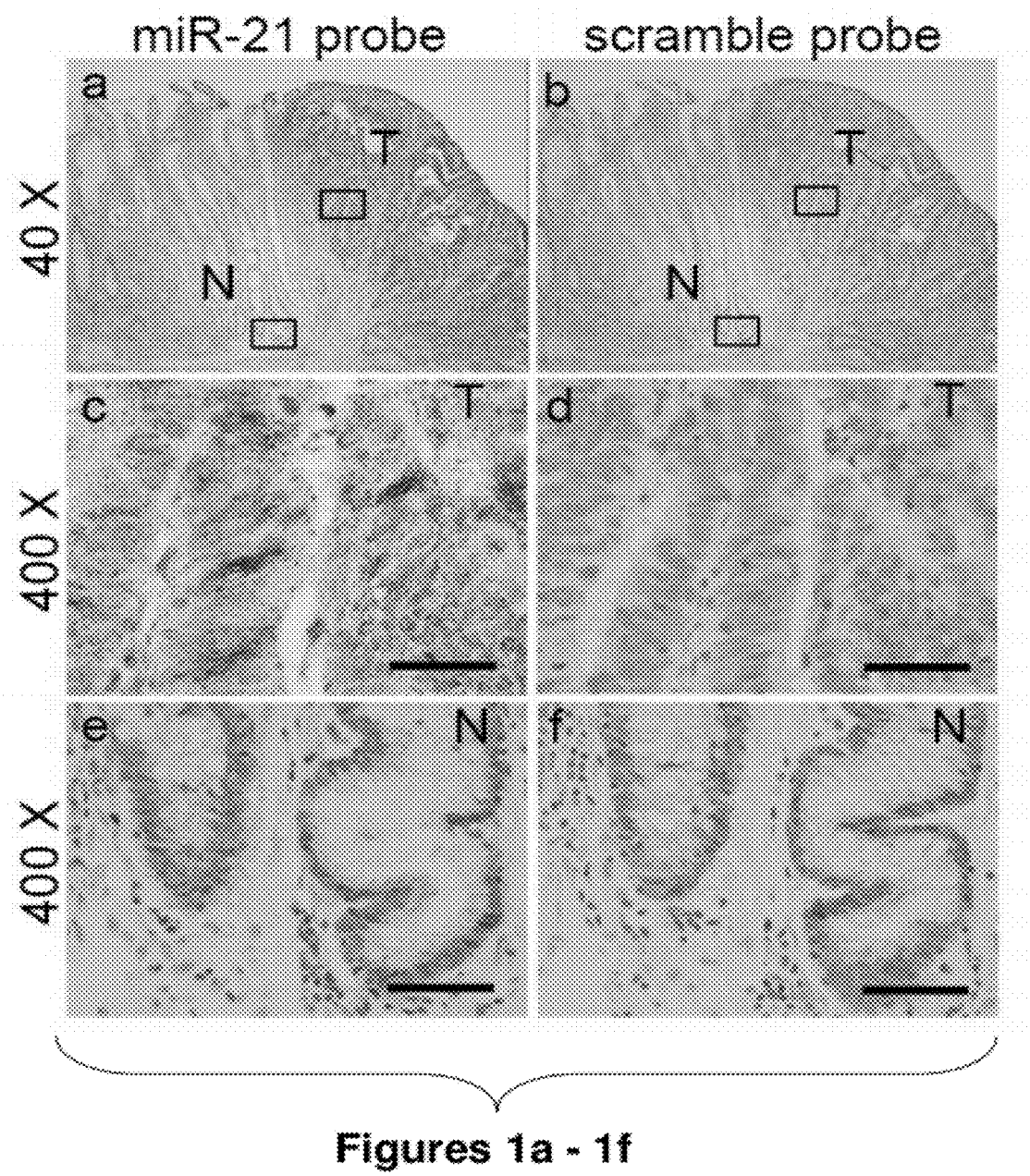
FIGS. 1a-1g: MiR-21 is expressed at higher levels in colon adenocarcinomas with increasing expression in more advanced tumors.

In one broad aspect, there is provided herein the identification of particular microRNAs whose expression is altered in cancer cells associated with different colon cancers, relative to normal control cells.

As used herein interchangeably, a "miR gene product," "microRNA," "miR," or "miRNA" refers to the unprocessed (e.g., precursor) or processed (e.g., mature) RNA transcript from a miR gene. As the miR gene products are not translated into protein, the term "miR gene products" does not include proteins. The unprocessed miR gene transcript is also called a "miR precursor" or "miR prec" and typically comprises an RNA transcript of about 70-100 nucleotides in length. The miR precursor can be processed by digestion with an RNAse (for example, Dicer, Argonaut, or RNAse III (e.g., *E. coli* RNAse III)) into an active 19-25 nucleotide RNA molecule. This active 19-25 nucleotide RNA molecule is also called the "processed" miR gene transcript or "mature" miRNA.

The active 19-25 nucleotide RNA molecule can be obtained from the miR precursor through natural processing routes (e.g., using intact cells or cell lysates) or by synthetic processing routes (e.g., using isolated processing enzymes, such as isolated Dicer, Argonaut, or RNAse III). It is understood that the active 19-25 nucleotide RNA molecule can also be produced directly by biological or chemical synthesis, without having been processed from the miR precursor. When a microRNA is referred to herein by name, the name corresponds to both the precursor and mature forms, unless otherwise indicated.

In one aspect, there is provided herein methods of diagnosing whether a subject has, or is at risk for developing, a colon cancer, comprising measuring the level of at least one miR gene product in a test sample from the subject and comparing the level of the miR gene product in the test sample to the level of a corresponding miR gene product in a control sample. As used herein, a "subject" can be any mammal that has, or is suspected of having, a solid cancer. In a preferred embodiment, the subject is a human who has, or is suspected of having, a colon cancer.

In one embodiment, the at least one miR gene product measured in the test sample is selected from the group consisting of miR-20a, miR-21, miR-106a, miR-181b, miR-203 and combinations thereof. In a particular embodiment, the miR gene product is miR-21.

The colon cancer-related disease can be any disorder or cancer that arises from the colon tissues. Such cancers are typically associated with the formation and/or presence of tumor masses and can be, for example, adenocarcinomas.

In one embodiment, the colon is an adenocarcinoma and the at least one miR gene product measured in the test sample is selected from the group consisting of miR-20a, miR-21, miR-106a, miR-181b, miR-203 and combinations thereof.

In a further embodiment, the at least one miR gene product measured in the test sample is miR-21.

The level of at least one miR gene product can be measured in a biological sample (e.g., cells, tissues) obtained from the subject. For example, a tissue sample (e.g., from a tumor) can be removed from a subject suspected of having a colon cancer-related disease by conventional biopsy techniques. In another embodiment, a blood sample can be removed from the subject, and blood cells (e.g., white blood cells) can be isolated for DNA extraction by standard techniques. The blood or tissue sample is preferably obtained from the subject prior to initiation of radiotherapy, chemotherapy or other therapeutic treatment. A corresponding control tissue or blood sample can be obtained from unaffected tissues of the subject, from a normal human individual or population of normal individuals, or from cultured cells corresponding to the majority of cells in the subject's sample. The control tissue or blood sample is then processed along with the sample from the subject, so that the levels of miR gene product produced from a given miR gene in cells from the subject's sample can be compared to the corresponding miR gene product levels from cells of the control sample. A reference miR expression standard for the biological sample can also be used as a control.

An alteration (e.g., an increase or decrease) in the level of a miR gene product in the sample obtained from the subject, relative to the level of a corresponding miR gene product in a control sample, is indicative of the presence of a colon cancer-related disease in the subject.

In one embodiment, the level of the at least one miR gene product in the test sample is greater than the level of the corresponding miR gene product in the control sample (i.e., expression of the miR gene product is "up-regulated"). As used herein, expression of a miR gene product is "up-regulated" when the amount of miR gene product in a cell or tissue sample from a subject is greater than the amount of the same gene product in a control cell or tissue sample.

In another embodiment, the level of the at least one miR gene product in the test sample is less than the level of the corresponding miR gene product in the control sample (i.e., expression of the miR gene product is "down-regulated"). As used herein, expression of a miR gene is "down-regulated" when the amount of miR gene product produced from that gene in a cell or tissue sample from a subject is less than the amount produced from the same gene in a control cell or tissue sample.

The relative miR gene expression in the control and normal samples can be determined with respect to one or more RNA expression standards. The standards can comprise, for example, a zero miR gene expression level, the miR gene expression level in a standard cell line, the miR gene expression level in unaffected tissues of the subject, or the average level of miR gene expression previously obtained for a population of normal human controls.

The level of a miR gene product in a sample can be measured using any technique that is suitable for detecting RNA expression levels in a biological sample. Suitable techniques (e.g., Northern blot analysis, RT-PCR, in situ hybridization) for determining RNA expression levels in a biological sample (e.g., cells, tissues) are well known to those of skill in the art. In a particular embodiment, the level of at least one miR gene product is detected using Northern blot analysis. For example, total cellular RNA can be purified from cells by homogenization in the presence of nucleic acid extraction buffer, followed by centrifugation. Nucleic acids are precipitated, and DNA is removed by treatment with DNase and precipitation. The RNA molecules are then separated by gel electrophoresis on agarose gels according to standard techniques, and transferred to nitrocellulose filters. The RNA is then immobilized on the filters by heating. Detection and quantification of specific RNA is accomplished using appropriately labeled DNA or RNA probes complementary to the RNA in question. See, for example, Molecular Cloning: A Laboratory Manual, J. Sambrook et al., eds., 2nd edition, Cold Spring Harbor Laboratory Press, 1989, Chapter 7, the entire disclosure of which is incorporated by reference.

Suitable probes for Northern blot hybridization of a given miR gene product can be produced from the nucleic acid sequences and include, but are not limited to, probes having at least about 70%, 75%, 80%, 85%, 90%, 95%, 98%, 99% or complete complementarity to a miR gene product of interest. Methods for preparation of labeled DNA and RNA probes, and the conditions for hybridization thereof to target nucleotide sequences, are described in Molecular Cloning: A Laboratory Manual, J. Sambrook et al., eds., 2nd edition, Cold Spring Harbor Laboratory Press, 1989, Chapters 10 and 11, the disclosures of which are incorporated herein by reference.

In one non-limiting example, the nucleic acid probe can be labeled with, e.g., a radionuclide, such as $^3$H, $^{32}$P, $^{33}$P, $^{14}$C, or $^{35}$S; a heavy metal; a ligand capable of functioning as a specific binding pair member for a labeled ligand (e.g., biotin, avidin or an antibody); a fluorescent molecule; a chemiluminescent molecule; an enzyme or the like.

Probes can be labeled to high specific activity by either the nick translation method of Rigby et al. (1977), *J. Mol. Biol.* 113:237-251 or by the random priming method of Fienberg et al. (1983), *Anal. Biochem.* 132:6-13, the entire disclosures of which are incorporated herein by reference. The latter is the method of choice for synthesizing $^{32}$P-labeled probes of high specific activity from single-stranded DNA or from RNA templates. For example, by replacing preexisting nucleotides with highly radioactive nucleotides according to the nick translation method, it is possible to prepare $^{32}$P-labeled nucleic acid probes with a specific activity well in excess of $10^8$ cpm/microgram. Autoradiographic detection of hybridization can then be performed by exposing hybridized filters to photographic film. Densitometric scanning of the photographic films exposed by the hybridized filters provides an accurate measurement of miR gene transcript levels. Using another approach, miR gene transcript levels can be quantified by computerized imaging systems, such as the *Molecular Dynamics 400-B 2D Phosphorimager* available from Amersham Biosciences, Piscataway, N.J.

Where radionuclide labeling of DNA or RNA probes is not practical, the random-primer method can be used to incorporate an analogue, for example, the dTTP analogue 5-(N—(N-biotinyl-epsilon-aminocaproyl)-3-aminoallyl) deoxyuridine triphosphate, into the probe molecule. The biotinylated probe oligonucleotide can be detected by reaction with biotin-binding proteins, such as avidin, streptavidin, and antibodies (e.g., anti-biotin antibodies) coupled to fluorescent dyes or enzymes that produce color reactions.

In addition to Northern and other RNA hybridization techniques, determining the levels of RNA transcripts can be accomplished using the technique of in situ hybridization. This technique requires fewer cells than the Northern blotting technique, and involves depositing whole cells onto a microscope cover slip and probing the nucleic acid content of the cell with a solution containing radioactive or otherwise labeled nucleic acid (e.g., cDNA or RNA) probes. This technique is particularly well-suited for analyzing tissue biopsy samples from subjects. The practice of the in situ hybridization technique is described in more detail in U.S. Pat. No. 5,427,916, the entire disclosure of which is incorporated herein by reference.

In one non-limiting example, suitable probes for in situ hybridization of a given miR gene product can be produced from the nucleic acid sequences, and include, but are not limited to, probes having at least about 70%, 75%, 80%, 85%, 90%, 95%, 98%, 99% or complete complementarity to a miR gene product of interest, as described above.

The relative number of miR gene transcripts in cells can also be determined by reverse transcription of miR gene transcripts, followed by amplification of the reverse-transcribed transcripts by polymerase chain reaction (RT-PCR). The levels of miR gene transcripts can be quantified in comparison with an internal standard, for example, the level of mRNA from a "housekeeping" gene present in the same sample. A suitable "housekeeping" gene for use as an internal standard includes, e.g., myosin or glyceraldehyde-3-phosphate dehydrogenase (G3PDH). Methods for performing quantitative and semi-quantitative RT-PCR, and variations thereof, are well known to those of skill in the art.

In some instances, it may be desirable to simultaneously determine the expression level of a plurality of different miR gene products in a sample. In other instances, it may be desirable to determine the expression level of the transcripts of all known miR genes correlated with a cancer. Assessing cancer-specific expression levels for hundreds of miR genes or gene products is time consuming and requires a large amount of total RNA (e.g., at least 20 µg for each Northern blot) and autoradiographic techniques that require radioactive isotopes.

To overcome these limitations, an oligolibrary, in microchip format (i.e., a microarray), may be constructed containing a set of oligonucleotide (e.g., oligodeoxynucleotides) probes that are specific for a set of miR genes. Using such a microarray, the expression level of multiple microRNAs in a biological sample can be determined by reverse transcribing the RNAs to generate a set of target oligodeoxynucleotides, and hybridizing them to probe the oligonucleotides on the microarray to generate a hybridization, or expression, profile. The hybridization profile of the test sample can then be compared to that of a control sample to determine which microRNAs have an altered expression level in solid cancer cells.

As used herein, "probe oligonucleotide" or "probe oligodeoxynucleotide" refers to an oligonucleotide that is capable of hybridizing to a target oligonucleotide. "Target oligonucleotide" or "target oligodeoxynucleotide" refers to a molecule to be detected (e.g., via hybridization). By "miR-specific probe oligonucleotide" or "probe oligonucleotide specific for a miR" is meant a probe oligonucleotide that has a sequence selected to hybridize to a specific miR gene product, or to a reverse transcript of the specific miR gene product.

An "expression profile" or "hybridization profile" of a particular sample is essentially a fingerprint of the state of the sample; while two states may have any particular gene similarly expressed, the evaluation of a number of genes simultaneously allows the generation of a gene expression profile that is unique to the state of the cell. That is, normal tissue may be distinguished from cancerous (e.g., tumor) tissue, and within cancerous tissue, different prognosis states (for example, good or poor long term survival prospects) may be determined By comparing expression profiles of the colon cancer tissue in different states, information regarding which genes are important (including both up- and down-regulation of genes) in each of these states is obtained. The identification of sequences that are differentially expressed in colon cancer tissue, as well as differential expression resulting in different prognostic outcomes, allows the use of this information in a number of ways.

In one non-limiting example, a particular treatment regime may be evaluated (e.g., to determine whether a chemotherapeutic drug acts to improve the long-term prognosis in a particular patient). Similarly, diagnosis may be done or confirmed by comparing patient samples with known expression profiles. Furthermore, these gene expression profiles (or individual genes) allow screening of drug candidates that suppress the colon cancer expression profile or convert a poor prognosis profile to a better prognosis profile.

Accordingly, there is also provided herein methods of diagnosing whether a subject has, or is at risk for developing, a colon cancer, comprising reverse transcribing RNA from a test sample obtained from the subject to provide a set of target oligodeoxynucleotides, hybridizing the target oligodeoxynucleotides to a microarray comprising miRNA-specific probe oligonucleotides to provide a hybridization profile for the test sample, and comparing the test sample hybridization profile to a hybridization profile generated from a control sample or reference standard, wherein an alteration in the signal of at least one miRNA is indicative of the subject either having, or being at risk for developing, a solid cancer.

In one embodiment, the microarray comprises miRNA-specific probe oligonucleotides for a substantial portion of all known human miRNAs. In a particular embodiment, the microarray comprises miRNA-specific probe oligonucleotides for one or more miRNAs selected from the group consisting of miR-20a, miR-21, miR-106a, miR-181b, miR-203 and combinations thereof.

The microarray can be prepared from gene-specific oligonucleotide probes generated from known miRNA sequences. The array may contain two different oligonucleotide probes for each miRNA, one containing the active, mature sequence and the other being specific for the precursor of the miRNA. The array may also contain controls, such as one or more mouse sequences differing from human orthologs by only a few bases, which can serve as controls for hybridization stringency conditions. tRNAs or other RNAs (e.g., rRNAs, mRNAs) from both species may also be printed on the microchip, providing an internal, relatively stable, positive control for specific hybridization. One or more appropriate controls for non-specific hybridization may also be included on the microchip. For this purpose, sequences are selected based upon the absence of any homology with any known miRNAs.

The microarray may be fabricated using techniques known in the art. For example, probe oligonucleotides of an appropriate length, e.g., 40 nucleotides, are 5'-amine modified at position C6 and printed using commercially available microarray systems, e.g., the GeneMachine OmniGrid™ 100 Microarrayer and Amersham CodeLink™ activated slides. Labeled cDNA oligomer corresponding to the target RNAs is prepared by reverse transcribing the target RNA with labeled primer. Following first strand synthesis, the RNA/DNA hybrids are denatured to degrade the RNA templates. The labeled target cDNAs thus prepared are then hybridized to the microarray chip under hybridizing conditions, e.g., 6×SSPE/30% formamide at 25° C. for 18 hours, followed by washing in 0.75×TNT (Tris HCl/NaCl/Tween 20) at 37° C. for 40 minutes. At positions on the array where the immobilized probe DNA recognizes a complementary target cDNA in the sample, hybridization occurs. The labeled target cDNA marks the exact position on the array where binding occurs, allowing automatic detection and quantification. The output consists of a list of hybridization events, indicating the relative abundance of specific cDNA sequences, and therefore the relative abundance of the corresponding complementary miRs, in the patient sample.

According to one embodiment, the labeled cDNA oligomer is a biotin-labeled cDNA, prepared from a biotin-labeled primer. The microarray is then processed by direct detection of the biotin-containing transcripts using, e.g., Streptavidin-Alexa647 conjugate, and scanned utilizing conventional scanning methods. Image intensities of each spot on the array are proportional to the abundance of the corresponding miR in the patient sample.

The use of the array has several advantages for miRNA expression detection. First, the global expression of several hundred genes can be identified in the same sample at one time point. Second, through careful design of the oligonucleotide probes, expression of both mature and precursor molecules can be identified. Third, in comparison with Northern blot analysis, the chip requires a small amount of RNA, and provides reproducible results using 2.5 µg of total RNA. The relatively limited number of miRNAs (a few hundred per species) allows the construction of a common microarray for several species, with distinct oligonucleotide probes for each. Such a tool allows for analysis of trans-species expression for each known miR under various conditions.

In addition to use for quantitative expression level assays of specific miRs, a microchip containing miRNA-specific probe oligonucleotides corresponding to a substantial portion of the miRNome, preferably the entire miRNome, may be employed to carry out miR gene expression profiling, for analysis of miR expression patterns. Distinct miR signatures can be associated with established disease markers, or directly with a disease state.

According to the expression profiling methods described herein, total RNA from a sample from a subject suspected of having a colon cancer-related disease quantitatively reverse transcribed to provide a set of labeled target oligodeoxynucleotides complementary to the RNA in the sample. The target oligodeoxynucleotides are then hybridized to a microarray comprising miRNA-specific probe oligonucleotides to provide a hybridization profile for the sample. The result is a hybridization profile for the sample representing the expression pattern of miRNA in the sample. The hybridization profile comprises the signal from the binding of the target oligodeoxynucleotides from the sample to the miRNA-specific probe oligonucleotides in the microarray. The profile may be recorded as the presence or absence of binding (signal vs. zero signal).

More preferably, the profile recorded includes the intensity of the signal from each hybridization. The profile is compared to the hybridization profile generated from a normal, i.e., noncancerous, control sample. An alteration in the signal is indicative of the presence of, or propensity to develop, cancer in the subject.

Other techniques for measuring miR gene expression are also within the skill in the art, and include various techniques for measuring rates of RNA transcription and degradation.

There is also provided herein methods of determining the prognosis of a subject with a colon cancer, comprising measuring the level of at least one miR gene product, which is associated with a particular prognosis in a colon cancer-related disease (e.g., a good or positive prognosis, a poor or adverse prognosis), in a test sample from the subject.

According to these methods, an alteration in the level of a miR gene product that is associated with a particular prognosis in the test sample, as compared to the level of a corresponding miR gene product in a control sample, is indicative of the subject having a solid cancer with a particular prognosis. In one embodiment, the miR gene product is associated with an adverse (i.e., poor) prognosis. Examples of an adverse prognosis include, but are not limited to, low survival rate and rapid disease progression. In certain embodiments, the level of the at least one miR gene product is measured by reverse transcribing RNA from a test sample obtained from the subject to provide a set of target oligodeoxynucleotides, hybridizing the target oligodeoxynucleotides to a microarray that comprises miRNA-specific probe oligonucleotides to provide a hybridization profile for the test sample, and comparing the test sample hybridization profile to a hybridization profile generated from a control sample.

Without wishing to be bound by any one theory, it is believed that alterations in the level of one or more miR gene products in cells can result in the deregulation of one or more intended targets for these miRs, which can lead to the formation of solid cancers. Therefore, altering the level of the miR gene product (e.g., by decreasing the level of a miR gene product that is up-regulated in solid cancer cells, by increasing the level of a miR gene product that is down-regulated in solid cancer cells) may successfully treat the solid cancer.

Accordingly, there is further provided herein methods of inhibiting tumorigenesis in a subject who has, or is suspected of having, a solid cancer wherein at least one miR gene product is deregulated (e.g., down-regulated, up-regulated) in the cancer cells of the subject. When the at least one isolated miR gene product is down-regulated in the cancer cells (e.g., miR-21), the method comprises administering an effective amount of the at least one isolated miR gene product, or an isolated variant or biologically-active fragment thereof, such that proliferation of cancer cells in the subject is inhibited.

For example, when a miR gene product is down-regulated in a cancer cell in a subject, administering an effective amount of an isolated miR gene product to the subject can inhibit proliferation of the cancer cell. The isolated miR gene product that is administered to the subject can be identical to the endogenous wild-type miR gene product (e.g., a miR gene product) that is down-regulated in the cancer cell or it can be a variant or biologically-active fragment thereof.

As defined herein, a "variant" of a miR gene product refers to a miRNA that has less than 100% identity to a corresponding wild-type miR gene product and possesses one or more biological activities of the corresponding wild-type miR gene product. Examples of such biological activities include, but are not limited to, inhibition of expression of a target RNA molecule (e.g., inhibiting translation of a target RNA molecule, modulating the stability of a target RNA molecule, inhibiting processing of a target RNA molecule) and inhibition of a cellular process associated with solid cancer (e.g., cell differentiation, cell growth, cell death). These variants include species variants and variants that are the consequence of one or more mutations (e.g., a substitution, a deletion, an insertion) in a miR gene. In certain embodiments, the variant is at least about 95%, 98%, or 99% identical to a corresponding wild-type miR gene product.

As defined herein, a "biologically-active fragment" of a miR gene product refers to an RNA fragment of a miR gene product that possesses one or more biological activities of a corresponding wild-type miR gene product. As described above, examples of such biological activities include, but are not limited to, inhibition of expression of a target RNA molecule and inhibition of a cellular process associated with a colon cancer. In certain embodiments, the biologically-active fragment is at least about 15 or 17 nucleotides in length. In a particular embodiment, an isolated miR gene product can be administered to a subject in combination with one or more additional anti-cancer treatments. Suitable anti-cancer treatments include, but are not limited to, chemotherapy, radiation therapy and combinations thereof (e.g., chemoradiation).

When the at least one isolated miR gene product is up-regulated in the cancer cells, the method comprises administering to the subject an effective amount of at least one compound for inhibiting expression of the at least one miR gene product, referred to herein as miR gene expression-inhibition compounds, such that proliferation of solid cancer cells is inhibited. In a particular embodiment, the at least one miR expression-inhibition compound is specific for a miR gene product selected from the group consisting miR-20a, miR-21, miR-106a, miR-181b, miR-203 and combinations thereof.

A miR gene expression-inhibiting compound can be administered to a subject in combination with one or more additional anti-cancer treatments. Suitable anti-cancer treatments include, but are not limited to, chemotherapy, radiation therapy and combinations thereof (e.g., chemoradiation).

The terms "treat", "treating" and "treatment", as used herein, refer to ameliorating symptoms associated with a disease or condition, for example, a solid cancer, including preventing or delaying the onset of the disease symptoms, and/or lessening the severity or frequency of symptoms of the disease or condition. The terms "subject", "patient" and "individual" are defined herein to include animals, such as mammals, including, but not limited to, primates, cows, sheep, goats, horses, dogs, cats, rabbits, guinea pigs, rats, mice or other bovine, ovine, equine, canine, feline, rodent, or murine species. In a preferred embodiment, the animal is a human.

As used herein, an "effective amount" of an isolated miR gene product is an amount sufficient to inhibit proliferation of a cancer cell in a subject suffering from a solid cancer. One skilled in the art can readily determine an effective amount of a miR gene product to be administered to a given subject, by taking into account factors, such as the size and weight of the subject; the extent of disease penetration; the age, health and sex of the subject; the route of administration; and whether the administration is regional or systemic.

For example, an effective amount of an isolated miR gene product can be based on the approximate weight of a tumor mass to be treated. The approximate weight of a tumor mass can be determined by calculating the approximate volume of the mass, wherein one cubic centimeter of volume is roughly equivalent to one gram. An effective amount of the isolated miR gene product based on the weight of a tumor mass can be in the range of about 10-500 micrograms/gram of tumor mass. In certain embodiments, the tumor mass can be at least about 10 micrograms/gram of tumor mass, at least about 60 micrograms/gram of tumor mass or at least about 100 micrograms/gram of tumor mass.

An effective amount of an isolated miR gene product can also be based on the approximate or estimated body weight of a subject to be treated. Preferably, such effective amounts are administered parenterally or enterally, as described herein. For example, an effective amount of the isolated miR gene product is administered to a subject can range from about 5 to about 3000 micrograms/kg of body weight, from about 700-1000 micrograms/kg of body weight, or greater than about 1000 micrograms/kg of body weight.

One skilled in the art can also readily determine an appropriate dosage regimen for the administration of an isolated miR gene product to a given subject. For example, a miR gene product can be administered to the subject once (e.g., as a single injection or deposition). Alternatively, a miR gene product can be administered once or twice daily to a subject for a period of from about three to about twenty-eight days, more particularly from about seven to about ten days. In a particular dosage regimen, a miR gene product is administered once a day for seven days. Where a dosage regimen comprises multiple administrations, it is understood that the effective amount of the miR gene product administered to the subject can comprise the total amount of gene product administered over the entire dosage regimen.

As used herein, an "isolated" miR gene product is one that is synthesized, or altered or removed from the natural state through human intervention. For example, a synthetic miR gene product, or a miR gene product partially or completely separated from the coexisting materials of its natural state, is considered to be "isolated." An isolated miR gene product can exist in substantially-purified form, or can exist in a cell into which the miR gene product has been delivered. Thus, a miR gene product that is deliberately delivered to, or expressed in, a cell is considered an "isolated" miR gene product. A miR gene product produced inside a cell from a miR precursor molecule is also considered to be an "isolated" molecule. According to one particular embodiment, the isolated miR gene products described herein can be used for the manufacture of a medicament for treating a solid cancer in a subject (e.g., a human).

Isolated miR gene products can be obtained using a number of standard techniques. For example, the miR gene products can be chemically synthesized or recombinantly produced using methods known in the art. In one embodiment, miR gene products are chemically synthesized using appropriately protected ribonucleoside phosphoramidites and a conventional DNA/RNA synthesizer. Commercial suppliers of synthetic RNA molecules or synthesis reagents include, e.g., Proligo (Hamburg, Germany), Dharmacon Research (Lafayette, Colo., U.S.A.), Pierce Chemical (part of Perbio Science, Rockford, Ill., U.S.A.), Glen Research (Sterling, Va., U.S.A.), ChemGenes (Ashland, Mass., U.S.A.) and Cruachem (Glasgow, UK).

Alternatively, the miR gene products can be expressed from recombinant circular or linear DNA plasmids using any suitable promoter. Suitable promoters for expressing RNA from a plasmid include, e.g., the U6 or H1 RNA pol III promoter sequences, or the cytomegalovirus promoters. Selection of other suitable promoters is within the skill in the art. The recombinant plasmids of the invention can also comprise inducible or regulatable promoters for expression of the miR gene products in cancer cells.

The miR gene products that are expressed from recombinant plasmids can be isolated from cultured cell expression systems by standard techniques. The miR gene products that are expressed from recombinant plasmids can also be delivered to, and expressed directly in, the cancer cells. The use of recombinant plasmids to deliver the miR gene products to cancer cells is discussed in more detail below.

The miR gene products can be expressed from a separate recombinant plasmid, or they can be expressed from the same recombinant plasmid. In one embodiment, the miR gene products are expressed as RNA precursor molecules from a single plasmid, and the precursor molecules are processed into the functional miR gene product by a suitable processing system, including, but not limited to, processing systems extant within a cancer cell. Other suitable processing systems include, e.g., the in vitro *Drosophila* cell lysate system (e.g., as described in U.S. Published Patent Application No. 2002/0086356 to Tuschl et al., the entire disclosure of which is incorporated herein by reference) and the *E. coli* RNAse III system (e.g., as described in U.S. Published Patent Application No. 2004/0014113 to Yang et al., the entire disclosure of which is incorporated herein by reference).

Selection of plasmids suitable for expressing the miR gene products, methods for inserting nucleic acid sequences into the plasmid to express the gene products, and methods of delivering the recombinant plasmid to the cells of interest are within the skill in the art. See, for example, Zeng et al. (2002), *Molecular Cell* 9:1327-1333; Tuschl (2002), *Nat. Biotechnol,* 20:446-448; Brummelkamp et al. (2002), *Science* 296:550-553; Miyagishi et al. (2002), *Nat. Biotechnol.* 20:497-500; Paddison et al. (2002), *Genes Dev.* 16:948-958; Lee et al. (2002), *Nat. Biotechnol.* 20:500-505; and Paul et al. (2002), *Nat. Biotechnol.* 20:505-508, the entire disclosures of which are incorporated herein by reference.

In one embodiment, a plasmid expressing the miR gene products comprises a sequence encoding a miR precursor RNA under the control of the CMV intermediate-early promoter. As used herein, "under the control" of a promoter means that the nucleic acid sequences encoding the miR gene product are located 3' of the promoter, so that the promoter can initiate transcription of the miR gene product coding sequences.

The miR gene products can also be expressed from recombinant viral vectors. It is contemplated that the miR gene products can be expressed from two separate recombinant viral vectors, or from the same viral vector. The RNA expressed from the recombinant viral vectors can either be isolated from cultured cell expression systems by standard techniques, or can be expressed directly in cancer cells. The use of recombinant viral vectors to deliver the miR gene products to cancer cells is discussed in more detail below.

The recombinant viral vectors of the invention comprise sequences encoding the miR gene products and any suitable promoter for expressing the RNA sequences. Suitable promoters include, but are not limited to, the U6 or H1 RNA pol III promoter sequences, or the cytomegalovirus promoters. Selection of other suitable promoters is within the skill in the art. The recombinant viral vectors of the invention can also comprise inducible or regulatable promoters for expression of the miR gene products in a cancer cell.

Any viral vector capable of accepting the coding sequences for the miR gene products can be used; for example, vectors derived from adenovirus (AV); adeno-associated virus (AAV); retroviruses (e.g., lentiviruses (LV), Rhabdoviruses, murine leukemia virus); herpes virus, and the like. The tropism of the viral vectors can be modified by pseudotyping the vectors with envelope proteins or other surface antigens from other viruses, or by substituting different viral capsid proteins, as appropriate.

For example, lentiviral vectors of the invention can be pseudotyped with surface proteins from vesicular stomatitis virus (VSV), rabies, Ebola, Mokola, and the like. AAV vectors of the invention can be made to target different cells by engineering the vectors to express different capsid protein serotypes. For example, an AAV vector expressing a serotype 2 capsid on a serotype 2 genome is called AAV 2/2. This serotype 2 capsid gene in the AAV 2/2 vector can be replaced by a serotype 5 capsid gene to produce an AAV 2/5 vector. Techniques for constructing AAV vectors that express different capsid protein serotypes are within the skill in the art; see, e.g., Rabinowitz, J. E., et al. (2002), *J. Virol.* 76:791-801, the entire disclosure of which is incorporated herein by reference.

Selection of recombinant viral vectors suitable for use in the invention, methods for inserting nucleic acid sequences for expressing RNA into the vector, methods of delivering the viral vector to the cells of interest, and recovery of the expressed RNA products are within the skill in the art. See, for example, Dornburg (1995), *Gene Therapy* 2:301-310; Eglitis (1988), *Biotechniques* 6:608-614; Miller (1990), *Hum. Gene Therapy* 1:5-14; and Anderson (1998), *Nature* 392:25-30, the entire disclosures of which are incorporated herein by reference.

Particularly suitable viral vectors are those derived from AV and AAV. A suitable AV vector for expressing the miR gene products, a method for constructing the recombinant AV vector, and a method for delivering the vector into target cells, are described in Xia et al. (2002), *Nat. Biotech.* 20:1006-1010, the entire disclosure of which is incorporated herein by reference. Suitable AAV vectors for expressing the miR gene products, methods for constructing the recombinant AAV vector, and methods for delivering the vectors into target cells are described in Samulski et al. (1987), *J. Virol.* 61:3096-3101; Fisher et al. (1996), *J. Virol.*, 70:520-532; Samulski et al. (1989), *J. Virol.* 63:3822-3826; U.S. Pat. No. 5,252,479; U.S. Pat. No. 5,139,941; International Patent Application No. WO 94/13788; and International Patent Application No. WO 93/24641, the entire disclosures of which are incorporated herein by reference. In one embodiment, the miR gene products are expressed from a single recombinant AAV vector comprising the CMV intermediate early promoter.

In a certain embodiment, a recombinant AAV viral vector of the invention comprises a nucleic acid sequence encoding a miR precursor RNA in operable connection with a polyT termination sequence under the control of a human U6 RNA promoter. As used herein, "in operable connection with a polyT termination sequence" means that the nucleic acid sequences encoding the sense or antisense strands are immediately adjacent to the polyT termination signal in the 5' direction. During transcription of the miR sequences from the vector, the polyT termination signals act to terminate transcription.

In other embodiments of the treatment methods of the invention, an effective amount of at least one compound that inhibits miR expression can be administered to the subject. As used herein, "inhibiting miR expression" means that the production of the precursor and/or active, mature form of miR gene product after treatment is less than the amount produced prior to treatment. One skilled in the art can readily determine whether miR expression has been inhibited in a cancer cell, using, for example, the techniques for determining miR transcript level discussed above for the diagnostic method. Inhibition can occur at the level of gene expression (i.e., by inhibiting transcription of a miR gene encoding the miR gene product) or at the level of processing (e.g., by inhibiting processing of a miR precursor into a mature, active miR).

As used herein, an "effective amount" of a compound that inhibits miR expression is an amount sufficient to inhibit proliferation of a cancer cell in a subject suffering from a cancer (e.g., a colon cancer). One skilled in the art can readily determine an effective amount of a miR expression-inhibition compound to be administered to a given subject, by taking into account factors, such as the size and weight of the subject; the extent of disease penetration; the age, health and sex of the subject; the route of administration; and whether the administration is regional or systemic.

For example, an effective amount of the expression-inhibition compound can be based on the approximate weight of a tumor mass to be treated, as described herein. An effective amount of a compound that inhibits miR expression can also be based on the approximate or estimated body weight of a subject to be treated, as described herein.

One skilled in the art can also readily determine an appropriate dosage regimen for administering a compound that inhibits miR expression to a given subject.

Suitable compounds for inhibiting miR gene expression include double-stranded RNA (such as short- or small-interfering RNA or "siRNA"), antisense nucleic acids, and enzymatic RNA molecules, such as ribozymes. Each of these compounds can be targeted to a given miR gene product and interfere with the expression of (e.g., inhibit translation of, induce cleavage or destruction of) the target miR gene product.

For example, expression of a given miR gene can be inhibited by inducing RNA interference of the miR gene with an isolated double-stranded RNA ("dsRNA") molecule which has at least 90%, for example at least 95%, at least 98%, at least 99%, or 100%, sequence homology with at least a portion of the miR gene product. In a particular embodiment, the dsRNA molecule is a "short or small interfering RNA" or "siRNA."

siRNA useful in the present methods comprise short double-stranded RNA from about 17 nucleotides to about 29 nucleotides in length, preferably from about 19 to about 25 nucleotides in length. The siRNA comprise a sense RNA strand and a complementary antisense RNA strand annealed together by standard Watson-Crick base-pairing interactions (hereinafter "base-paired"). The sense strand comprises a nucleic acid sequence that is substantially identical to a nucleic acid sequence contained within the target miR gene product.

As used herein, a nucleic acid sequence in an siRNA which is "substantially identical" to a target sequence contained within the target mRNA is a nucleic acid sequence that is identical to the target sequence, or that differs from the target sequence by one or two nucleotides. The sense and antisense strands of the siRNA can comprise two complementary, single-stranded RNA molecules, or can comprise a single molecule in which two complementary portions are base-paired and are covalently linked by a single-stranded "hairpin" area.

The siRNA can also be altered RNA that differs from naturally-occurring RNA by the addition, deletion, substitution and/or alteration of one or more nucleotides. Such alterations can include addition of non-nucleotide material, such as to the end(s) of the siRNA or to one or more internal nucleotides of the siRNA, or modifications that make the siRNA resistant to nuclease digestion, or the substitution of one or more nucleotides in the siRNA with deoxyribonucleotides.

One or both strands of the siRNA can also comprise a 3' overhang. As used herein, a "3' overhang" refers to at least one unpaired nucleotide extending from the 3'-end of a duplexed RNA strand. Thus, in certain embodiments, the siRNA comprises at least one 3' overhang of from 1 to about 6 nucleotides (which includes ribonucleotides or deoxyribonucleotides) in length, from 1 to about 5 nucleotides in length, from 1 to about 4 nucleotides in length, or from about 2 to about 4 nucleotides in length. In a particular embodiment, the 3' overhang is present on both strands of the siRNA, and is 2 nucleotides in length. For example, each strand of the siRNA can comprise 3' overhangs of dithymidylic acid ("TT") or diuridylic acid ("uu").

The siRNA can be produced chemically or biologically, or can be expressed from a recombinant plasmid or viral vector, as described above for the isolated miR gene products. Exemplary methods for producing and testing dsRNA or siRNA molecules are described in U.S. Published Patent Application No. 2002/0173478 to Gewirtz and in U.S. Published Patent Application No. 2004/0018176 to Reich et al., the entire disclosures of both of which are incorporated herein by reference.

Expression of a given miR gene can also be inhibited by an antisense nucleic acid. As used herein, an "antisense nucleic acid" refers to a nucleic acid molecule that binds to target RNA by means of RNA-RNA, RNA-DNA or RNA-peptide nucleic acid interactions, which alters the activity of the target RNA. Antisense nucleic acids suitable for use in the present methods are single-stranded nucleic acids (e.g., RNA, DNA, RNA-DNA chimeras, peptide nucleic acid (PNA)) that generally comprise a nucleic acid sequence complementary to a contiguous nucleic acid sequence in a miR gene product. The antisense nucleic acid can comprise a nucleic acid sequence that is 50-100% complementary, 75-100% complementary, or 95-100% complementary to a contiguous nucleic acid sequence in a miR gene product.

Without wishing to be bound by any theory, it is believed that the antisense nucleic acids activate RNase H or another cellular nuclease that digests the miR gene product/antisense nucleic acid duplex.

Antisense nucleic acids can also contain modifications to the nucleic acid backbone or to the sugar and base moieties (or their equivalent) to enhance target specificity, nuclease resistance, delivery or other properties related to efficacy of the molecule. Such modifications include cholesterol moieties, duplex intercalators, such as acridine, or one or more nuclease-resistant groups.

Antisense nucleic acids can be produced chemically or biologically, or can be expressed from a recombinant plasmid or viral vector, as described above for the isolated miR gene products. Exemplary methods for producing and testing are within the skill in the art; see, e.g., Stein and Cheng (1993), *Science* 261:1004 and U.S. Pat. No. 5,849,902 to Woolf et al., the entire disclosures of which are incorporated herein by reference.

Expression of a given miR gene can also be inhibited by an enzymatic nucleic acid. As used herein, an "enzymatic nucleic acid" refers to a nucleic acid comprising a substrate binding region that has complementarity to a contiguous nucleic acid sequence of a miR gene product, and which is able to specifically cleave the miR gene product. The enzymatic nucleic acid substrate binding region can be, for example, 50-100% complementary, 75-100% complementary, or 95-100% complementary to a contiguous nucleic acid sequence in a miR gene product. The enzymatic nucleic acids can also comprise modifications at the base, sugar, and/or phosphate groups. An exemplary enzymatic nucleic acid for use in the present methods is a ribozyme.

The enzymatic nucleic acids can be produced chemically or biologically, or can be expressed from a recombinant plasmid or viral vector, as described above for the isolated miR gene products. Exemplary methods for producing and testing dsRNA or siRNA molecules are described in Werner and Uhlenbeck (1995), *Nucl. Acids Res.* 23:2092-96; Hammann et al. (1999), *Antisense and Nucleic Acid Drug Dev.* 9:25-31; and U.S. Pat. No. 4,987,071 to Cech et al, the entire disclosures of which are incorporated herein by reference.

Administration of at least one miR gene product, or at least one compound for inhibiting miR expression, will inhibit the proliferation of cancer cells in a subject who has a solid cancer. As used herein, to "inhibit the proliferation of a cancer cell" means to kill the cell, or permanently or temporarily arrest or slow the growth of the cell. Inhibition of cancer cell proliferation can be inferred if the number of such cells in the subject remains constant or decreases after administration of the miR gene products or miR gene expression-inhibition compounds. An inhibition of cancer cell proliferation can also be inferred if the absolute number of such cells increases, but the rate of tumor growth decreases.

The number of cancer cells in the body of a subject can be determined by direct measurement, or by estimation from the size of primary or metastatic tumor masses. For example, the number of cancer cells in a subject can be measured by immunohistological methods, flow cytometry, or other techniques designed to detect characteristic surface markers of cancer cells.

The size of a tumor mass can be ascertained by direct visual observation, or by diagnostic imaging methods, such as X-ray, magnetic resonance imaging, ultrasound, and scintigraphy. Diagnostic imaging methods used to ascertain size of the tumor mass can be employed with or without contrast agents, as is known in the art. The size of a tumor mass can also be ascertained by physical means, such as palpation of the tissue mass or measurement of the tissue mass with a measuring instrument, such as a caliper.

The miR gene products or miR gene expression-inhibition compounds can be administered to a subject by any means suitable for delivering these compounds to cancer cells of the subject. For example, the miR gene products or miR expression-inhibition compounds can be administered by methods suitable to transfect cells of the subject with these compounds, or with nucleic acids comprising sequences encoding these compounds.

In one embodiment, the cells are transfected with a plasmid or viral vector comprising sequences encoding at least one miR gene product or miR gene expression-inhibition compound.

Transfection methods for eukaryotic cells are well known in the art, and include, e.g., direct injection of the nucleic acid into the nucleus or pronucleus of a cell; electroporation; liposome transfer or transfer mediated by lipophilic materials; receptor-mediated nucleic acid delivery, bioballistic or particle acceleration; calcium phosphate precipitation, and transfection mediated by viral vectors.

For example, cells can be transfected with a liposomal transfer compound, e.g., DOTAP (N-[1-(2,3-dioleoyloxy)propyl]-N,N,N-trimethyl-ammonium methylsulfate, Boehringer-Mannheim) or an equivalent, such as LIPOFECTIN. The amount of nucleic acid used is not critical to the practice of the invention; acceptable results may be achieved with 0.1-100 micrograms of nucleic acid/$10^5$ cells. For example, a ratio of about 0.5 micrograms of plasmid vector in 3 micrograms of DOTAP per $10^5$ cells can be used.

A miR gene product or miR gene expression-inhibition compound can also be administered to a subject by any suitable enteral or parenteral administration route. Suitable enteral administration routes for the present methods include, e.g., oral, rectal, or intranasal delivery. Suitable parenteral administration routes include, e.g., intravascular administration (e.g., intravenous bolus injection, intravenous infusion, intra-arterial bolus injection, intra-arterial infusion and catheter instillation into the vasculature); peri- and intra-tissue injection (e.g., peri-tumoral and intra-tumoral injection, intra-retinal injection, or subretinal injection); subcutaneous injection or deposition, including subcutaneous infusion (such as by osmotic pumps); direct application to the tissue of interest, for example by a catheter or other placement device (e.g., a retinal pellet or a suppository or an implant comprising a porous, non-porous, or gelatinous material); and inhalation. Particularly suitable administration routes are injection, infusion and direct injection into the tumor.

In the present methods, a miR gene product or miR gene product expression-inhibition compound can be administered to the subject either as naked RNA, in combination with a delivery reagent, or as a nucleic acid (e.g., a recombinant plasmid or viral vector) comprising sequences that express the miR gene product or miR gene product expression-inhibition compound. Suitable delivery reagents include, e.g., the Mints Transit TKO lipophilic reagent; lipofectin; lipofectamine; cellfectin; polycations (e.g., polylysine), and liposomes.

Recombinant plasmids and viral vectors comprising sequences that express the miR gene products or miR gene expression-inhibition compounds, and techniques for delivering such plasmids and vectors to cancer cells, are discussed herein and/or are well known in the art.

In a particular embodiment, liposomes are used to deliver a miR gene product or miR gene expression-inhibition compound (or nucleic acids comprising sequences encoding them) to a subject. Liposomes can also increase the blood half-life of the gene products or nucleic acids. Suitable liposomes for use in the invention can be formed from standard vesicle-forming lipids, which generally include neutral or negatively charged phospholipids and a sterol, such as cholesterol. The selection of lipids is generally guided by consideration of factors, such as the desired liposome size and half-life of the liposomes in the blood stream. A variety of methods are known for preparing liposomes, for example, as described in Szoka et al. (1980), *Ann. Rev. Biophys. Bioeng.* 9:467; and U.S. Pat. Nos. 4,235,871, 4,501,728, 4,837,028, and 5,019,369, the entire disclosures of which are incorporated herein by reference.

The liposomes for use in the present methods can comprise a ligand molecule that targets the liposome to cancer cells. Ligands that bind to receptors prevalent in cancer cells, such as monoclonal antibodies that bind to tumor cell antigens, are preferred.

The liposomes for use in the present methods can also be modified so as to avoid clearance by the mononuclear macrophage system ("MMS") and reticuloendothelial system ("RES"). Such modified liposomes have opsonization-inhibition moieties on the surface or incorporated into the liposome structure. In a particularly preferred embodiment, a liposome of the invention can comprise both an opsonization-inhibition moiety and a ligand.

Opsonization-inhibiting moieties for use in preparing the liposomes of the invention are typically large hydrophilic polymers that are bound to the liposome membrane. As used herein, an opsonization-inhibiting moiety is "bound" to a liposome membrane when it is chemically or physically attached to the membrane, e.g., by the intercalation of a lipid-soluble anchor into the membrane itself, or by binding directly to active groups of membrane lipids. These opsonization-inhibiting hydrophilic polymers form a protective surface layer that significantly decreases the uptake of the liposomes by the MMS and RES; e.g., as described in U.S. Pat. No. 4,920,016, the entire disclosure of which is incorporated herein by reference.

Opsonization-inhibiting moieties suitable for modifying liposomes are preferably water-soluble polymers with a number-average molecular weight from about 500 to about 40,000 daltons, and more preferably from about 2,000 to about 20,000 daltons. Such polymers include polyethylene glycol (PEG) or polypropylene glycol (PPG) derivatives; e.g., methoxy PEG or PPG, and PEG or PPG stearate; synthetic polymers, such as polyacrylamide or poly N-vinyl pyrrolidone; linear, branched, or dendrimeric polyamidoamines; polyacrylic acids; polyalcohols, e.g., polyvinylalcohol and polyxylitol to which carboxylic or amino groups are chemically linked, as well as gangliosides, such as ganglioside GM1. Copolymers of PEG, methoxy PEG, or methoxy PPG, or derivatives thereof, are also suitable. In addition, the opsonization-inhibiting polymer can be a block copolymer of PEG and either a polyamino acid, polysaccharide, polyamidoamine, polyethyleneamine, or polynucleotide. The opsonization-inhibiting polymers can also be natural polysaccharides containing amino acids or carboxylic acids, e.g., galacturonic acid, glucuronic acid, mannuronic acid, hyaluronic acid, pectic acid, neuraminic acid, alginic acid, carrageenan; aminated polysaccharides or oligosaccharides (linear or branched); or carboxylated polysaccharides or oligosaccharides, e.g., reacted with derivatives of carbonic acids with resultant linking of carboxylic groups. Preferably, the opsonization-inhibiting moiety is a PEG, PPG, or a derivative thereof. Liposomes modified with PEG or PEG-derivatives are sometimes called "PEGylated liposomes."

The opsonization-inhibiting moiety can be bound to the liposome membrane by any one of numerous well-known techniques. For example, an N-hydroxysuccinimide ester of PEG can be bound to a phosphatidyl-ethanolamine lipid-soluble anchor, and then bound to a membrane. Similarly, a dextran polymer can be derivatized with a stearylamine lipid-soluble anchor via reductive amination using $Na(CN)BH_3$ and a solvent mixture, such as tetrahydrofuran and water in a 30:12 ratio at 60° C.

Liposomes modified with opsonization-inhibition moieties remain in the circulation much longer than unmodified liposomes. For this reason, such liposomes are sometimes called "stealth" liposomes. Stealth liposomes are known to accumulate in tissues fed by porous or "leaky" microvasculature. Thus, tissue characterized by such microvasculature defects, for example, solid tumors, will efficiently accumulate these liposomes; see Gabizon, et al. (1988), Proc. Natl. Acad. Sci., U.S.A., 18:6949-53. In addition, the reduced uptake by the RES lowers the toxicity of stealth liposomes by preventing significant accumulation of the liposomes in the liver and spleen. Thus, liposomes that are modified with opsonization-inhibition moieties are particularly suited to deliver the miR gene products or miR gene expression-inhibition compounds (or nucleic acids comprising sequences encoding them) to tumor cells.

The miR gene products or miR gene expression-inhibition compounds can be formulated as pharmaceutical compositions, sometimes called "medicaments," prior to administering them to a subject, according to techniques known in the art. Accordingly, the invention encompasses pharmaceutical compositions for treating a solid cancer. In one embodiment, the pharmaceutical composition comprises at least one isolated miR gene product, or an isolated variant or biologically-active fragment thereof, and a pharmaceutically-acceptable carrier. In a particular embodiment, the at least one miR gene product corresponds to a miR gene product that has a decreased level of expression in solid cancer cells relative to suitable control cells. In certain embodiments the isolated miR gene product is selected from the group consisting of miR-20a, miR-21, miR-106a, miR-181b, miR-203 and combinations thereof.

In other embodiments, the pharmaceutical compositions of the invention comprise at least one miR expression-inhibition compound. In a particular embodiment, the at least one miR gene expression-inhibition compound is specific for a miR gene whose expression is greater in colon cancer cells than control cells. In certain embodiments, the miR gene expression-inhibition compound is specific for one or more miR gene products selected from the group consisting of miR-20a, miR-21, miR-106a, miR-181b, miR-203 and combinations thereof.

Pharmaceutical compositions of the present invention are characterized as being at least sterile and pyrogen-free. As used herein, "pharmaceutical compositions" include formulations for human and veterinary use. Methods for preparing pharmaceutical compositions of the invention are within the skill in the art, for example as described in Remington's Pharmaceutical Science, 17th ed., Mack Publishing Company, Easton, Pa. (1985), the entire disclosure of which is incorporated herein by reference.

The present pharmaceutical compositions comprise at least one miR gene product or miR gene expression-inhibition compound (or at least one nucleic acid comprising sequences encoding them) (e.g., 0.1 to 90% by weight), or a physiologically-acceptable salt thereof, mixed with a pharmaceutically-acceptable carrier. In certain embodiments, the pharmaceutical compositions of the invention additionally comprise one or more anti-cancer agents (e.g., chemotherapeutic agents). The pharmaceutical formulations of the invention can also comprise at least one miR gene product or miR gene expression-inhibition compound (or at least one nucleic acid comprising sequences encoding them), which are encapsulated by liposomes and a pharmaceutically-acceptable carrier. In one embodiment, the pharmaceutical composition comprises a miR gene or gene product that is miR-21.

Especially suitable pharmaceutically-acceptable carriers are water, buffered water, normal saline, 0.4% saline, 0.3% glycine, hyaluronic acid and the like.

In a particular embodiment, the pharmaceutical compositions of the invention comprise at least one miR gene product or miR gene expression-inhibition compound (or at least one nucleic acid comprising sequences encoding them) that is resistant to degradation by nucleases. One skilled in the art can readily synthesize nucleic acids that are nuclease resistant, for example, by incorporating one or more ribonucleotides that is modified at the 2'-position into the miR gene product. Suitable 2'-modified ribonucleotides include those modified at the 2'-position with fluoro, amino, alkyl, alkoxy, and O-allyl.

Pharmaceutical compositions of the invention can also comprise conventional pharmaceutical excipients and/or additives. Suitable pharmaceutical excipients include stabilizers, antioxidants, osmolality adjusting agents, buffers, and pH adjusting agents. Suitable additives include, e.g., physiologically biocompatible buffers (e.g., tromethamine hydrochloride), additions of chelants (such as, for example, DTPA or DTPA-bisamide) or calcium chelate complexes (such as, for example, calcium DTPA, CaNaDTPA-bisamide), or, optionally, additions of calcium or sodium salts (for example, calcium chloride, calcium ascorbate, calcium gluconate or calcium lactate). Pharmaceutical compositions of the invention can be packaged for use in liquid form, or can be lyophilized.

For solid pharmaceutical compositions of the invention, conventional nontoxic solid pharmaceutically-acceptable carriers can be used; for example, pharmaceutical grades of mannitol, lactose, starch, magnesium stearate, sodium saccharin, talcum, cellulose, glucose, sucrose, magnesium carbonate, and the like.

For example, a solid pharmaceutical composition for oral administration can comprise any of the carriers and excipients listed above and 10-95%, preferably 25%-75%, of the at least one miR gene product or miR gene expression-inhibition compound (or at least one nucleic acid comprising sequences encoding them). A pharmaceutical composition for aerosol (inhalational) administration can comprise 0.01-20% by weight, preferably 1%-10% by weight, of the at least one miR gene product or miR gene expression-inhibition compound (or at least one nucleic acid comprising sequences encoding them) encapsulated in a liposome as described above, and a propellant. A carrier can also be included as desired; e.g., lecithin for intranasal delivery.

The pharmaceutical compositions of the invention can further comprise one or more anti-cancer agents. In a particular embodiment, the compositions comprise at least one miR gene product or miR gene expression-inhibition compound (or at least one nucleic acid comprising sequences encoding them) and at least one chemotherapeutic agent. Chemotherapeutic agents that are suitable for the methods of the invention include, but are not limited to, DNA-alkylating agents, anti-tumor antibiotic agents, anti-metabolic agents, tubulin stabilizing agents, tubulin destabilizing agents, hormone antagonist agents, topoisomerase inhibitors, protein kinase inhibitors, HMG-CoA inhibitors, CDK inhibitors, cyclin inhibitors, caspase inhibitors, metalloproteinase inhibitors, antisense nucleic acids, triple-helix DNAs, nucleic acids aptamers, and molecularly-modified viral, bacterial and exotoxic agents. Examples of suitable agents for the compositions of the present invention include, but are not limited to, cytidine arabinoside, methotrexate, vincristine, etoposide (VP-16), doxorubicin (adriamycin), cisplatin (CDDP), dexamethasone, arglabin, cyclophosphamide, sarcolysin, methylnitrosourea, fluorouracil, 5-fluorouracil (5FU), vinblastine, camptothecin, actinomycin-D, mitomycin C, hydrogen peroxide, oxaliplatin, irinotecan, topotecan, leucovorin, carmustine, streptozocin, CPT-11, taxol, tamoxifen, dacarbazine, rituximab, daunorubicin, 1-β-D-arabinofuranosylcytosine, imatinib, fludarabine, docetaxel, FOLFOX4.

There is also provided herein methods of identifying an inhibitor of tumorigenesis, comprising providing a test agent to a cell and measuring the level of at least one miR gene product in the cell. In one embodiment, the method comprises providing a test agent to a cell and measuring the level of at least one miR gene product associated with decreased expression levels in cancer cells. An increase in the level of the miR gene product in the cell after the agent is provided, relative to a suitable control cell (e.g., agent is not provided), is indicative of the test agent being an inhibitor of tumorigenesis. In a particular embodiment, at least one miR gene product associated with decreased expression levels in cancer cells is selected from the group consisting miR-20a, miR-21, miR-106a, miR-181b, miR-203 and combinations thereof.

In other embodiments, the method comprises providing a test agent to a cell and measuring the level of at least one miR gene product associated with increased expression levels in cancer cells. A decrease in the level of the miR gene product in the cell after the agent is provided, relative to a suitable control cell (e.g., agent is not provided), is indicative of the test agent being an inhibitor of tumorigenesis. In a particular embodiment, at least one miR gene product associated with increased expression levels in cancer cells is selected from the group consisting of miR-20a, miR-21, miR-106a, miR-181b, miR-203 and combinations thereof.

Suitable agents include, but are not limited to drugs (e.g., small molecules, peptides), and biological macromolecules (e.g., proteins, nucleic acids). The agent can be produced recombinantly, synthetically, or it may be isolated (i.e., purified) from a natural source. Various methods for providing such agents to a cell (e.g., transfection) are well known in the art, and several of such methods are described hereinabove. Methods for detecting the expression of at least one miR gene product (e.g., Northern blotting, in situ hybridization, RT-PCR, expression profiling) are also well known in the art. Several of these methods are also described hereinabove.

The invention will now be illustrated by the following non-limiting examples.

Example 1

MicroRNA Expression Patterns are Altered in Colon Tumors

We compared microRNA profiles of 84 pairs of colon tumorous and adjacent nontumorous tissues using microRNA microarrays[30]. These 84 subjects were patients recruited from the greater Baltimore, Md. area with incident colon adenocarcinoma and are referred to as the Maryland test cohort (Table 1).

TABLE 1

Characteristics of Population and Tumors

| | Maryland Test Cohort N = 84 | Hong Kong Validation Cohort N = 113 |
|---|---|---|
| | Recruitment area | |
| | Baltimore, Maryland, USA | Hong Kong, China |
| Age at enrollment - yr | | |
| Mean ± SD | 64.6 ± 10.7 | 55.8 ± 15 |
| Range | 32-87 | 32-84 |
| Sex - no. (%) | | |
| Male | 66 (79) | 56 (50) |
| Female | 18 (21) | 57 (50) |
| Race - no. (%) | | |
| White | 52 (62) | 0 (0) |
| Black | 32 (38) | 0 (0) |
| Asian | 0 (0) | 113 (100) |
| Tumor location - no. (%) | | |
| Distal | 48 (59) | 90 (80) |
| Proximal | 34 (41) | 23 (20) |
| Adenocarcinoma Histology - no. (%) | | |
| Adenocarcinoma | 75 (89) | 105 (93) |
| Mucinous adenocarcinoma | 8 (10) | 7 (6) |
| Adenosquamous carcinoma | 1 (1) | 0 (0) |
| Signet ring cell and mucinous | 0 (0) | 1 (1) |
| Adjuvant Chemotherapy2 - no. (%) | | |
| Received | 22 (37) | 40 (35) |
| Did not receive | 37 (63) | 73 (65) |
| TNM Stage - no. (%) | | |
| II | 29 (34) | 37 (33) |
| III | 36 (43) | 48 (42) |
| IV | 10 (12) | 19 (17) |

[1]Distal includes tumors located in or distal to the descending colon. Proximal tumors include tumors in or proximal to the splenic flexure. Tumor location was available for 82 subjects in the original cohort and all subjects in the validation cohort.
[2]Detailed information pertaining to receipt of chemotherapy was available for 59 subjects in the test cohort and all subjects in the validation cohort. Chemotherapy was primarily fluorouracil-based (in forms of either intravenous 5-fluorouracil or oral drugs including tegafur with uracil [UFT]) with or without Levamisole or Leucovorin.

Tumor microRNA profiles were distinctly different than nontumor profiles. Thirty-seven independent microRNAs were found to be differentially expressed in tumors (p<0.001 with false discovery rate <0.5%; Table 2.

TABLE 2

| Probe | mature miR | p-value[1] | FDR[2] | Fold Change | Chromosomal location |
|---|---|---|---|---|---|
| MicroRNAs the are Differentially Expressed in Tumors | | | | | |
| hsa-mir-21No1 | miR-21 | <1e-07 | <1e-07 | 1.7 | 17q23.2 |
| hsa-mir-021-prec-17No1 | miR-21 | <1e-07 | <1e-07 | 1.8 | 17q23.2 |
| hsa-mir-092-prec-13 = 092-1No2 | miR-92 | <1e-07 | <1e-07 | 1.4 | 13g31.3 |
| hsa-mir-222-precNo2 | miR-222 | 1.40E-06 | 8.05E-05 | 1.2 | Xp11.3 |
| hsa-mir-181b-2No1 | miR-181b | 1.90E-06 | 8.74E-05 | 1.2 | 9q33.3 |
| hsa-mir-210-prec | mIR-210 | 1.12E-05 | 0.00032 | 1.2 | 11p15.5 |
| hsa-mir-020-prec | miR-20a | 2.53E-05 | 0.00057 | 1.5 | 13q31.3 |
| hsa-mir-106-prec-X | miR-106a | 3.30E-05 | 0.00058 | 1.4 | X26.2 |
| hsa-mir-106aNo1 | miR-106a | 3.51E-05 | 0.00058 | 1.4 | X26.2 |
| hsa-mir-093-prec-7.1⁻093-1 | miR-93 | 3.52E-05 | 0.00058 | 1.2 | 7q22.1 |
| hsa-mir-335No2 | miR-335 | 3.55E-05 | 0.00058 | 1.2 | 7q32.2 |

TABLE 2-continued

| Probe | mature miR | p-value[1] | FDR[2] | Fold Change | Chromosomal location |
|---|---|---|---|---|---|
| hsa-mir-222-precNo1 | miR-222 | 4.27E−05 | 0.00065 | 1.2 | Xp11.3 |
| hsa-mir-338No1 | miR-338 | 5.78E−05 | 0.00074 | 1.1 | 17q25.3 |
| hsa-mir-133bNo2 | miR-133b | 6.50E−05 | 0.00079 | 1.1 | 6p12.2 |
| hsa-mir-092-prec-X = 092-2 | miR-92 | 7.95E−05 | 0.00083 | 1.4 | Xq26.2 |
| hsa-mir-346No1 | miR-346 | 8.42E−05 | 0.00084 | 1.2 | 10q23.2 |
| hsa-mir-106bNo1 | miR-106b | 0.0002091 | 0.00178 | 1.2 | 7q22.1 |
| hsa-mir-135-2-prec | miR-153a | 0.0002363 | 0.00194 | 1.1 | 12q23.1 |
| hsa-mir-219-1No2 | miR-219 | 0.0002515 | 0.00199 | 1.3 | 9q34.11 |
| hsa-mir-34aNo1 | miR-34a | 0.000265 | 0.00203 | 1.1 | 1p36.22 |
| hsa-mir-099b-prec-19No1 | miR-99b | 0.0003758 | 0.00259 | 1.1 | 19q13.41 |
| hsa-mir-185-precNo2 | miR-185 | 0.0003827 | 0.00259 | 1.2 | 22q11.21 |
| hsa-mir-223-prec | miR-223 | 0.0004038 | 0.00265 | 1.4 | Xq12 |
| hsa-mir-211-precNo2 | miR-211 | 0.0004338 | 0.00277 | 1.1 | 15q13.3 |
| hsa-mir-135-1-prec | miR-135a | 0.0004648 | 0.00287 | 1.1 | 3p21.1 |
| hsa-mir-127-prec | miR-127 | 0.0004748 | 0.00287 | 1.1 | 14q32.31 |
| hsa-mir-203-precNo1 | miR-203 | 0.0004993 | 0.00294 | 1.4 | 14q32.33 |
| hsa-mir-212-precNo1 | miR-212 | 0.0006339 | 0.00364 | 1.1 | 17p13.3 |
| hsa-mir-095-prec-4 | miR-95 | 0.0006996 | 0.00392 | 1.2 | 4p16.1 |
| hsa-mir-017-precNo2 | miR-17-5p | 0.0007252 | 0.00392 | 1.3 | 13q31.3 |
| MicroRNAs with reduced Expression in Tumors ||||||
| hsa-mir-342No2 | miR-342 | 4.00E−06 | 0.00015 | 0.9 | 14q32.2 |
| hsa-mir-192-2/3No1 | miR-192 | 8.70E−06 | 0.00029 | 0.7 | 11q13.1 |
| hsa-mir-1-2No2 | miR-1 | 2.22E−05 | 0.00057 | 0.9 | 18g11.2 |
| hsa-mir-34bNo2 | miR-34b | 4.78E−05 | 0.00069 | 0.8 | 11q23.1 |
| hsa-mir-215-precNo1 | miR-215 | 5.26E−05 | 0.00071 | 0.7 | 1q41 |
| hsa-mir-192No1 | miR-192 | 7.36E−05 | 0.00081 | 0.7 | 11q13.1 |
| hsa-mir-301 No2 | miR-301 | 7.44E−05 | 0.00081 | 0.7 | 17q23.2 |
| hsa-miR-324-5pNo2 | miR-324-5p | 1.00E−04 | 0.00096 | 0.9 | 17p13.1 |
| hsa-mir-030a-precNo2 | miR-30a-3p | 0.0001933 | 0.00171 | 0.9 | 6q13 |
| hsa-mir-1-1 No2 | miR-1 | 0.0002906 | 0.00216 | 0.9 | 20q13.33 |
| hsa-mir-34cNo2 | miR-34c | 0.0007334 | 0.00392 | 0.9 | 11q23.1 |
| hsa-mir-331 No2 | miR-331 | 0.0008555 | 0.00446 | 0.9 | 12q22 |
| hsa-mir-148bNo2 | miR-148b | 0.0008726 | 0.00446 | 0.9 | 12q13.13 |

[1]P-values reported are the result of paired class comparison analysis of microRNA expression patterns from 84 pairs colon adenocarcinomas and nontumorus tissue.
[2]FDR = False Discovery Rate Twenty-six microRNAs were expressed at higher levels in tumors with miR-21 enriched the most at 1.8-fold. Global microRNA profiles distinguish between tumor and paired nontumorous tissue with 89% accuracy using either the 3-nearest neighbors or nearest centroid class prediction algorithms (10-fold cross validation repeated 100 times), suggesting a systematic change in microRNA expression patterns during tumor formation.

We chose miR-20a, miR-21, miR-106a, miR-181b and miR-203 for validation based on their expression differences between tumor and paired nontumorous tissue combined with their association to poor survival. For validation, we measured the expression levels of these microRNAs with qRT-PCR in tumor and paired nontumorous tissue from an independent cohort. The validation cohort consists of 113 patients recruited from Hong Kong, China with incident colon cancer (Table 1).

MiR-20a (2.3-fold), miR-21 (2.8-fold), miR106a (2.4-fold), miR-181 lb (1.4-fold) and miR-203 (1.8-fold) were all expressed at higher levels in tumors (p<0.001, Wilcoxon matched pairs test) (Table 3a).

TABLE 3

MicroRNA Expression in Tumors vs. Paired Nontumorous Tissue

Table 3a - the Hong Kong Validation Cohort

| microRNA | ΔΔCt[1] | SD (ΔΔ Ct) | Fold change in tumors[2] | p-value[3] |
|---|---|---|---|---|
| miR-20a | 1.18 | 0.97 | 2.3 fold | p < 0.001 |
| miR-21 | 1.47 | 1.20 | 2.8 fold | p < 0.001 |
| miR-106a | 1.25 | 0.94 | 2.4 fold | p < 0.001 |
| miR-181 b | 0.47 | 1.03 | 1.4 fold | p < 0.001 |
| miR-203 | 0.83 | 1.40 | 1.8 fold | p < 0.001 |

Table 3b - MicroRNA Expression in Adenoma vs. Paired Non-adenoma Tissue

| microRNA | Average ΔΔ Ct[1] | SD (ΔΔ Ct) | Fold change in adenomas[2] | p-value[3] |
|---|---|---|---|---|
| miR-20a | −0.11 | 0.97 | 0.9 fold | p = 0.82 |
| miR-21 | 0.64 | 0.90 | 1.6 fold | p = 0.006 |
| miR-106a | 0.28 | 1.22 | 1.2 fold | p = 0.19 |
| miR-181 b | 0.30 | 1.24 | 1.2 fold | p = 0.27 |
| miR-203 | 0.77 | 1.98 | 1.7 fold | p = 0.14 |

[1]Average (tumor ΔCt − paired non-tumor ΔCt) or Average (adenoma ΔCt − paired nonadenoma ΔCt) from qRT-PCR.
[2]Calcluated by $2^{ΔΔ}$
[3]Wilcoxon matched pairs test.
SD = standard deviation.
Bolded numbers are statistically significant. For the tumor/nontumor comparisons, 113 pairs of tissues were used for miR-20a and miR-203 while 111 pairs of tissue were used for miR-21, miR-106a, and miR-181b. For all adenoma/non-adenoma comparisons, 18 pairs of tissue were used.

Most tumors (89% for miR-20a, 87% for miR-21, 90% for miR-106a, 71% for miR-181b and 74% for miR-203) had higher expression of these microRNAs than paired nontumorous tissue. Expression patterns for these five microRNAs distinguish tumor versus paired nontumor status with 96% or 98% accuracy based on 3-nearest neighbors or nearest centroid algorithms, respectively (10-fold cross validation, repeated 100 times).

We used in situ hybridization to visualize miR-21 expression in tumor and adjacent non-tumor tissue (see FIGS. 1a-f).

MiR-21 is expressed at high levels in both the nuclei and cytoplasm of colonic epithelial cells in human tumor tissue compared to adjacent nontumorous tissue. These results are consistent with the qRT-PCR and microarray data and support a role for microRNAs in carcinogenesis.

MiR-21 is Expressed at Higher Levels in Colon Adenomas

Adenomas represent a precursor stage for colon adenocarcinomas. We tested miR-20a, miR21, miR-106a, miR-181b and miR-203 expression levels by qRT-PCR in 18 pairs of adenoma and adjacent nonadenoma tissue. Although four of five microRNAs showed increased levels in adenoma tissue, only miR-21 was significantly enriched at 1.6-fold higher ($p=0.006$, Wilcoxon matched pairs test) (see Table 3b).

Adenoma tissue expressed higher levels of miR-21 in 15/18 matched pairs. More advanced stages of tumors express higher levels of miR-21. Subjects were stratified based on the diagnosis of adenoma and TNM staging, where adenoma was considered the least advanced and TNM Stage IV was most advanced. Adenomas expressed lower levels of miR-21 expression than tumors from the validation cohort ($p<0.001$, Mann-Whitney test). More advanced tumors expressed higher levels of miR-21 expression (test for trend, $p<0.001$) (see FIG. 1g).

Figure 2:
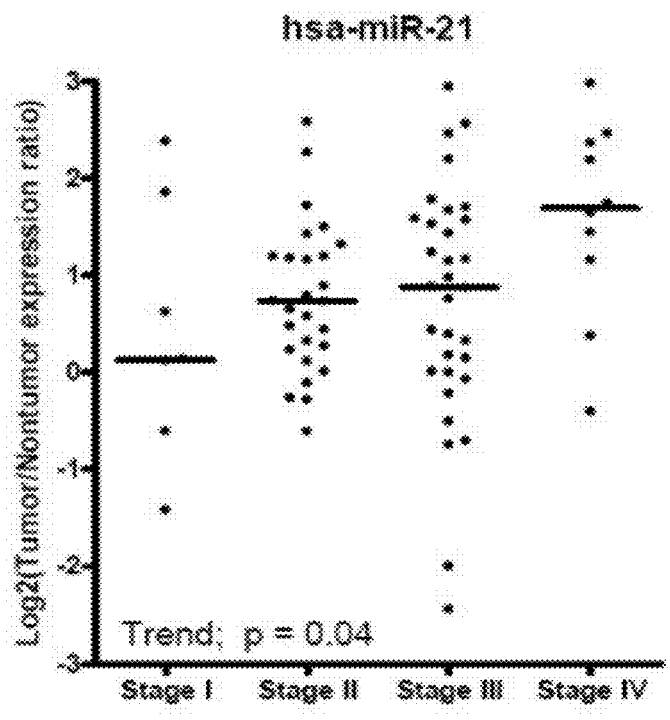
FIG. 2: miR-21 is expressed at higher levels in more advanced tumors. MicroRNA microarrays were used to measure miR-21 expression levels. Dot plots represent miR-21 $\log_2$ (tumor/nontumor ratios) as calculated from microRNA microarrays from the original cohort. The probe hsa-miR-21-prec 17No 1 from the microarray was used to measure miR-21 expression. Tissues with undetectable expression of miR-21 based on microarray data were excluded. Tissue types have been ordered from TNM stage I to stage IV tumors. Bars indicate median value. There is a significant trend that more advanced tumors have higher expression of miR-21 (p=0.04; nonparametric test for trend across ordered groups).

This trend was also observed using microRNA microarray data from the Maryland test cohort ($p=0.04$) (see FIG. 2).

High miR-21 Expression Predicts a Poor Prognosis in Two Independent Cohorts

We analyzed individual microRNA tumor/nontumor (T/N) expression ratios to determine if any were associated with poor prognosis. T/N microRNA expression ratios were classified as high based on highest tertile. We searched for any microRNA where high T/N ratios were associated with cancer survival ($p<0.05$). From those, we selected microRNAs that were differentially expressed in tumors ($p<0.001$). Five microRNAs satisfied these criteria. Kaplan-Meier analysis indicated that high T/N ratios for miR-20a ($p=0.02$), miR-21 ($p=0.004$), miR-106a ($p=0.01$), miR-181b ($p=0.04$), and miR-203 ($p=0.004$) were each associated with a poor survival. These five microRNAs were selected for further analysis.

Colon adenocarcinomas from 89-93% of the subjects in this study were of a typical histology. A minority of tumors were of mucinous adenocarcinoma, adenosquamous carcinoma, or signet ring cell carcinoma histologies (see Table 1). Different subtypes of adenocarcinomas can be associated with different clinical outcomes, including survival prognosis. To remove potential confounding associated with histology, we excluded all subjects with mucinous adenocarcinomas, adenosquamous carcinomas and signet ring cell carcinomas from the initial analysis.

Figure 3A:
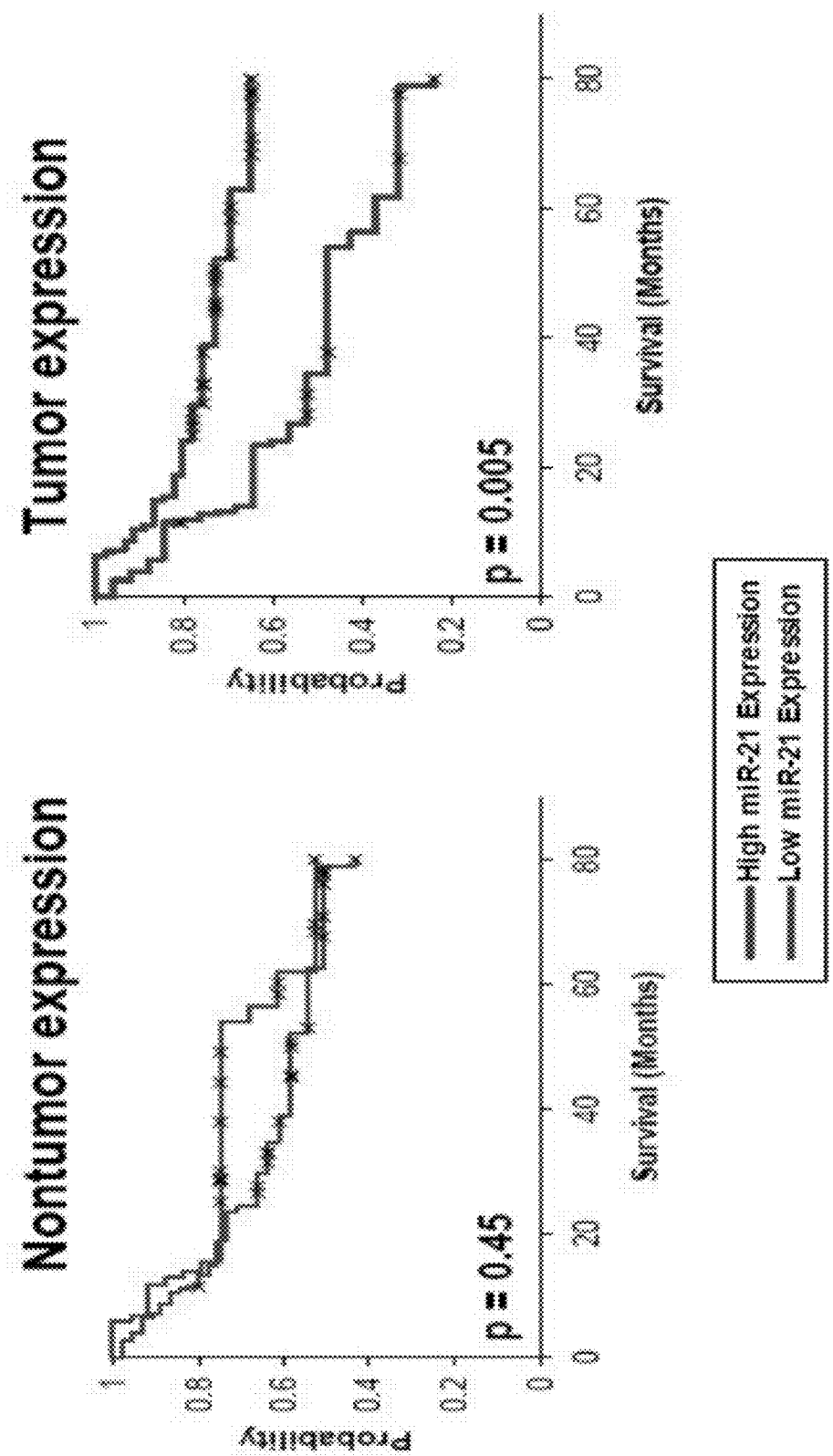
FIGS. 3a and 3b: High miR-21 expression in tumors predicts a poor survival in subjects with typical adenocarcinoma histology in both independent cohorts. This analysis excludes subjects with either mucinous adenocarcinoma or adenosquamous carcinoma histology.

Associations of T/N ratios with poor survival could be due to microRNA expression levels in the tumor tissue, the surrounding nontumorous tissue, or a combination of both. To distinguish these possibilities we analyzed the association of microRNA expression in tumors and paired nontumors separately. High expression levels in tumors (based on highest tertile) for miR-20a, miR-21, miR106a, miR-181b and miR-203 were each associated with a poor survival in the Maryland test cohort (see FIG. 3a, also from data not shown). No significant association with microRNA expression in nontumorous tissue was observed for any of the five microRNAs.

Univariate and multivariate Cox proportional hazards analysis was used to evaluate the association of tumor expression levels with prognosis in individuals with typical adenocarcinoma (Table 4a).

TABLE 4

Univariate and Multivariate Cox Regression Analysis of miR-21 Expression Levels and Overall Cancer Survival in Subjects with Colon Adenocarcinoma Table 4a

| Characteristic | Maryland Test Cohort | | | |
|---|---|---|---|---|
| | Univariate analysis | | Multivariate analysis2 | |
| | HR (95% CI) | p-value | HR (95% CI) | p-value |
| miR-21 expression[3] N = 71 | | | | |
| Low | 1.0 | | 1.0 | |
| High | 2.5 (1.2-5.2) | 0.01 | 2.9 (1.4-6.1) | 0.004 |
| TNM Stage | | | | |
| I-II | 1.0 | | 1.0 | |
| III-IV | 3.5 (1.6-7.9) | 0.002 | 3.4 (1.5-7.8) | 0.004 |
| Age at enrollment | | | | |
| <50 | 1.0 | | | |
| ≧50 | 0.7 (0.2-2.3) | 0.52 | | |
| Sex | | | | |
| Female | 1.0 | | | |
| Male | 1.4 (0.5-3.9) | 0.57 | | |
| Race | | | | |
| White | 1.0 | | | |
| Black | 1.0 (0.5-2.1) | 0.97 | | |
| Tumor Location | | | | |
| Distal | 1.0 | | | |
| Proximal | 0.6 (0.3-1.4) | 0.26 | | |

Table 4b

| Characteristic | Hong Kong Validation Cohort | | | |
|---|---|---|---|---|
| | Univariate analysis | | Multivariate analysis[2] | |
| | HR (95% CI) | p-value | HR (95% CI) | p-value |
| miR-21 expression[3] n = 103 | | | | |
| Low | 1.0 | | 1.0 | |
| High | 2.4 (1.4-3.9) | 0.002 | 2.4 (1.4-4.1) | 0.002 |

TABLE 4-continued

Univariate and Multivariate Cox Regression Analysis of miR-21 Expression Levels and Overall Cancer Survival in Subjects with Colon Adenocarcinoma TNM Stage

| | | | | |
|---|---|---|---|---|
| I-II | 1.0 | | 1.0 | |
| III-IV | 4.7 (2.4-9.5) | <0.001 | 4.7 (2.4-9.5) | <0.001 |

Age at enrollment

| | | |
|---|---|---|
| <50 | 1.0 | |
| ≧50 | 1.5 (0.9-2.6) | 0.14 |

Sex

| | | |
|---|---|---|
| Female | 1.0 | |
| Male | 1.4 (0.8-2.3) | 0.29 |

Tumor Location

| | | |
|---|---|---|
| Distal | 1.0 | |
| Proximal | 0.7 (0.3-1.4) | 0.27 |

MicroRNA expression was measured with miRNA microarrays for the Maryland cohort and with qRT-PCR with the Hong Kong cohort.
[1]Cases with mucinous adenocarcinoma, adenosquamous carcinoma or signet ring cell carcinomas were excluded from this analysis.
[2]Multivariate analysis used stepwise addition and removal of clinical covariates found to be associated with survival in univariate models (p < 0.10) and final models include only those covariates which were significantly associated with survival (Wald statistic p < 0.05).
[3]High expression in tumors for all miRNAs was defined based on the highest tertile.

Individuals with tumors expressing high levels of miR-21 were at a significantly higher risk of dying from colon cancer in both univariate (HR=2.5 [1.2-5.2], p=0.01) and multivariate (HR=2.9 [1.4-6.1], p=0.004) analyses.

Figure 3B:
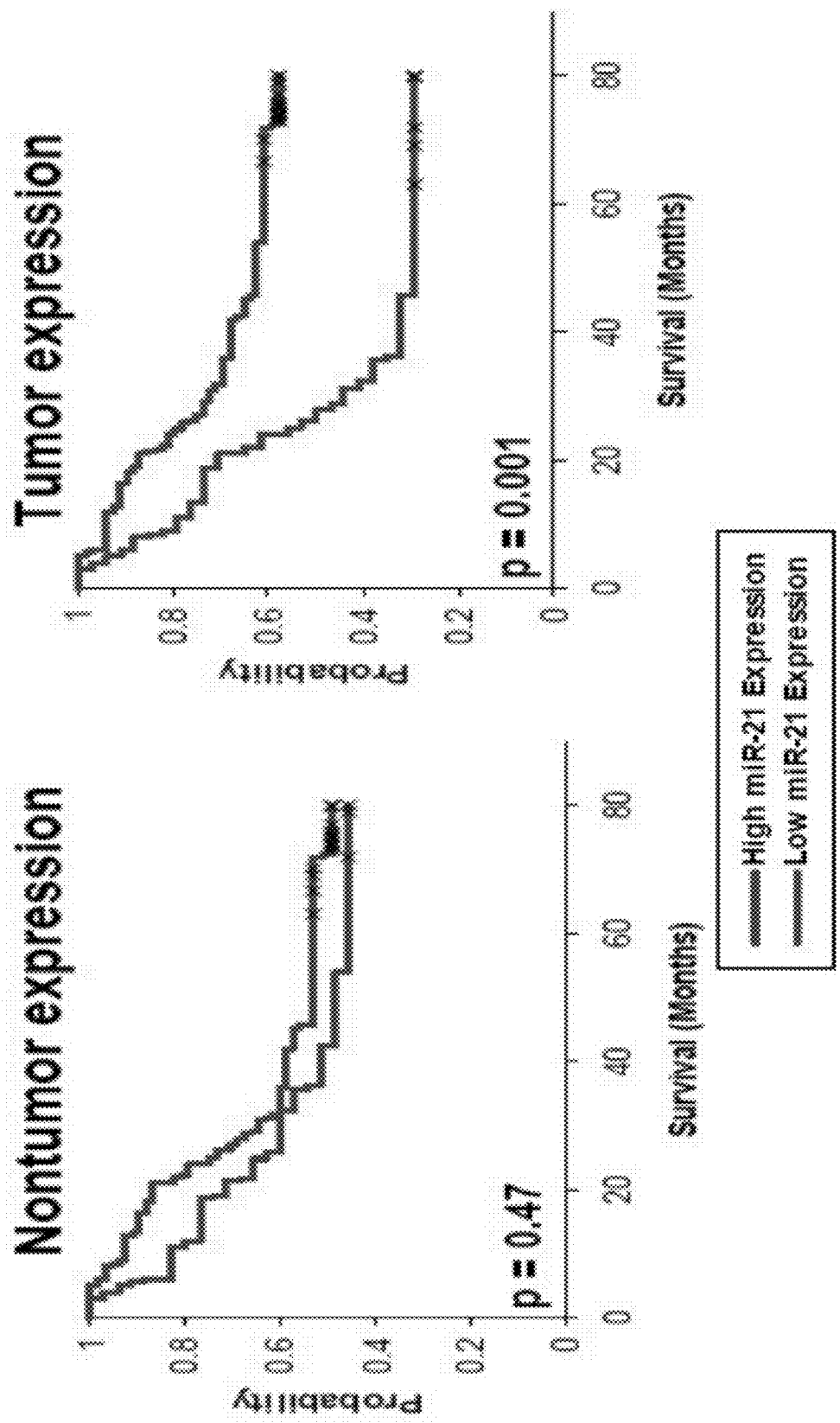

To validate these findings, we used qRT-PCR to measure tumor and nontumor expression levels for these five microRNAs in the Hong Kong validation cohort and analyzed associations with prognosis. High miR-21 tumor expression predicts a poor prognosis in the Hong Kong validation cohort (p=0.001, Kaplan-Meier log rank test) while expression in nontumorous tissue does not (see FIG. 3b).

We did not find statistically significant associations with prognosis and expression of miR-20a, miR-106a, 181b or miR-203 in this cohort.

High miR-21 expression in tumors was not significantly associated with age, gender, tumor histology, or tumor location (Fisher's exact test) in the Hong Kong validation cohort. All covariates were examined by Cox proportional hazards analysis (Table 4b).

High miR-21 expression in tumors (HR=2.4 [1.4-3.9], p=0.002) and TNM staging (HR=4.7 [2.4-9.5], p<0.001) were significantly associated with survival in univariate models. Multivariate Cox regression analysis demonstrated that high miR-21 expression in tumors predicts poor survival prognosis (HR=2.4 [1.4-4.1], p=0.002) independent of other clinical covariates, consistent with our findings in the Maryland test cohort.

Figure 4A:
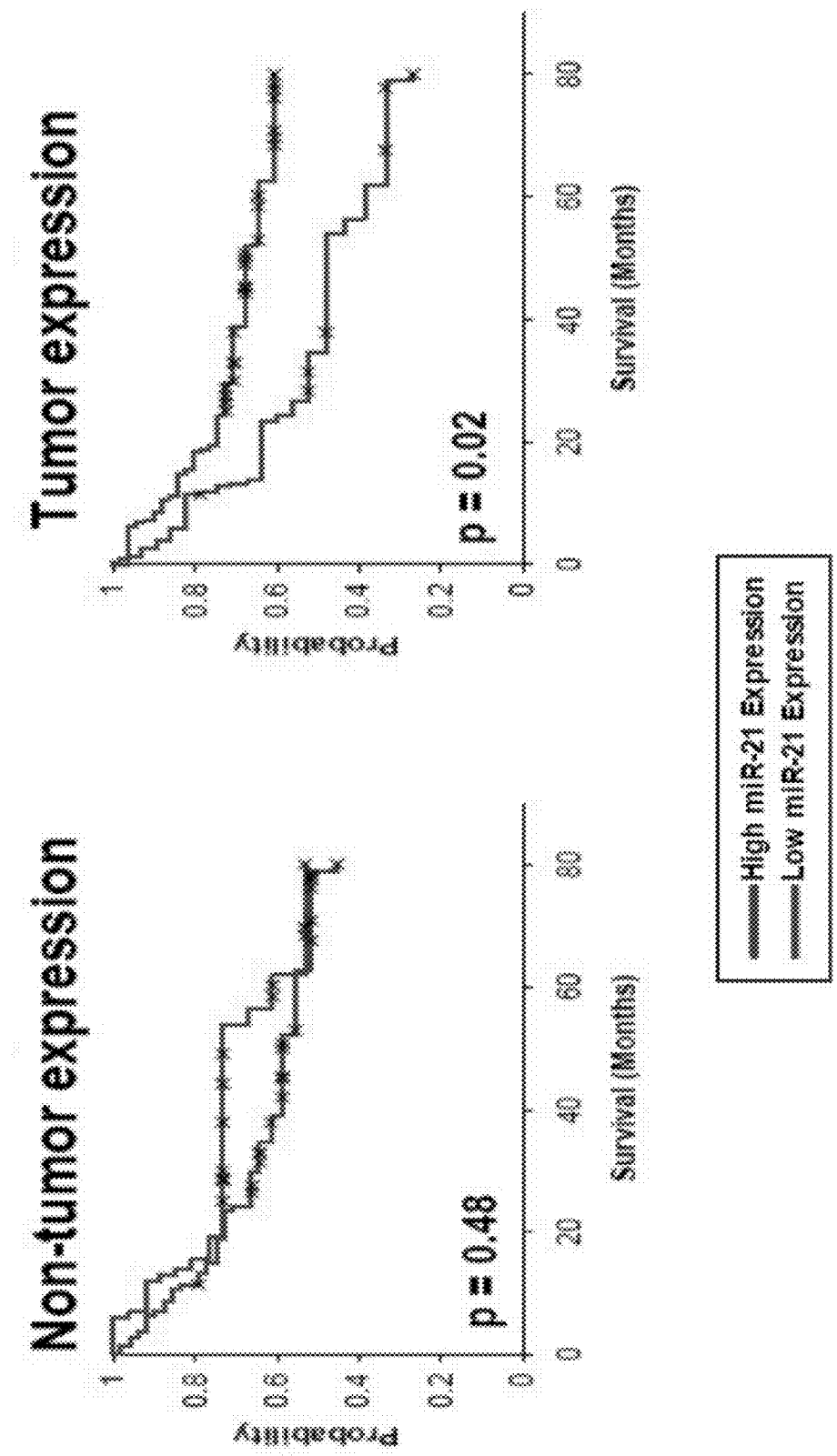
FIGS. 4a and 4b: High miR-21 expression in tumors predicts poor survival in both independent cohorts. This analysis includes all subjects regardless of adenocarcinoma histology.
Figure 4B:
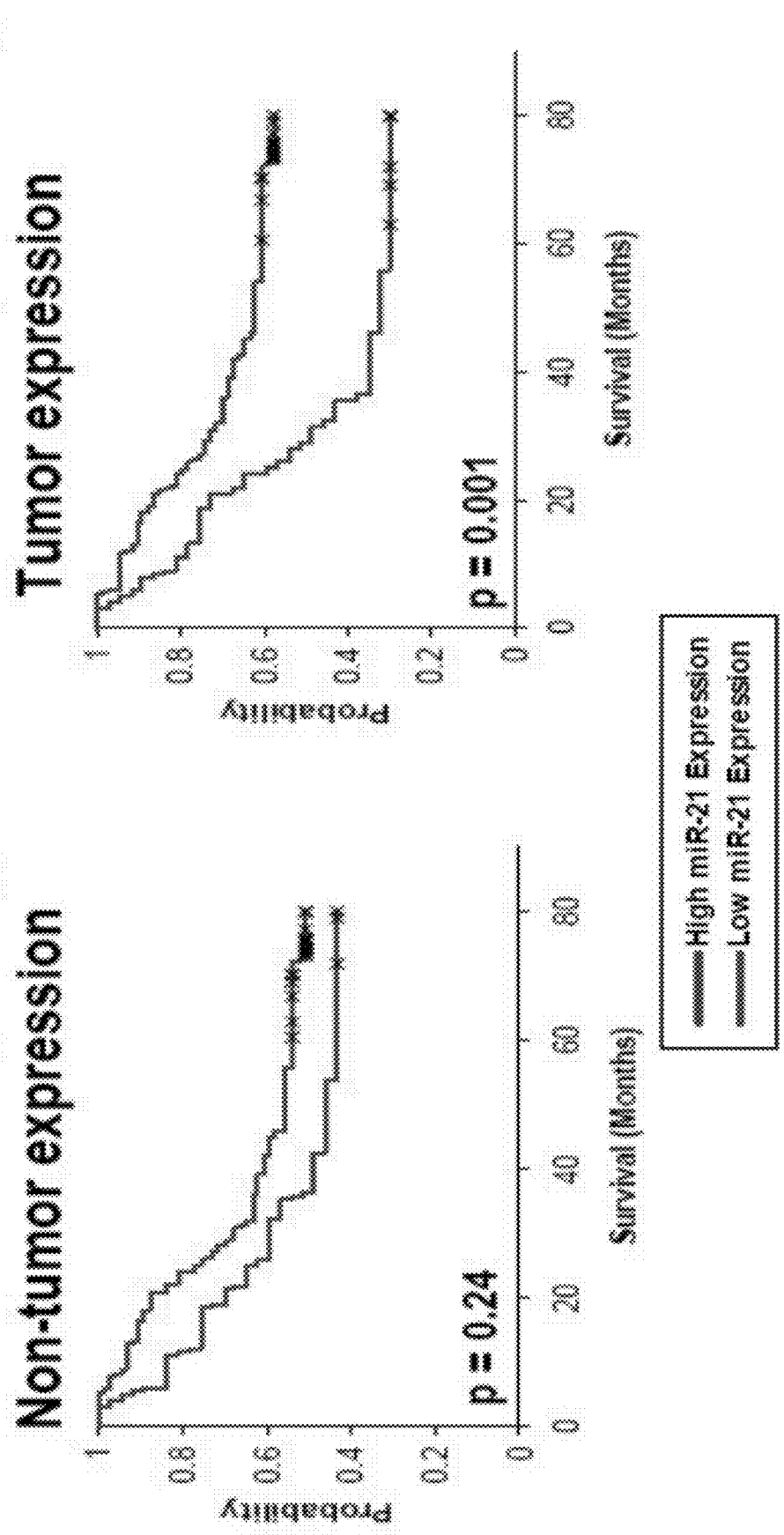

We repeated the analysis including all subjects regardless of tumor histology. In both cohorts, the association with high miR-21 expression and prognosis remained (See FIG. 4, See Table 5).

TABLE 5

Univariate and Multivariate Cox Regression Analysis of miR-21 Expression Levels and Overall Cancer Survival in Subjects with All Subjects Table 5a

| | Maryland Test Cohort | | | |
|---|---|---|---|---|
| | Univariate analysis | | Multivariate analysis | |
| Characteristic | HR (95% CI) | p-value | HR (95% CI) | p-value |
| miR-21 expression[3] N = 79 | | | | |
| Low | 1.0 | | 1.0 | |
| High | 2.0 (1.1-4.0) | 0.04 | 2.1 (1.1-4.0) | 0.03 |
| TNM Stage | | | | |
| I-II | 1.0 | | 1.0 | |
| III-IV | 3.2 (1.5-6.9) | 0.002 | 3.2 (1.5-6.8) | 0.003 |
| Age at enrollment | | | | |
| <50 | 1.0 | | | |
| ≧50 | 0.7 (0.2-2.4) | 0.59 | | |
| Sex | | | | |
| Female | 1.0 | | | |
| Male | 1.6 (0.7-4.2) | 0.33 | | |
| Race | | | | |
| White | 1.0 | | | |
| Black | 1.0 (0.5-2.0) | 0.99 | | |
| Tumor Location | | | | |
| Distal | 1.0 | | | |
| Proximal | 0.8 (0.3-2.1) | 0.65 | | |
| Histology | 1.0 | | | |
| Adenocarcinoma | | | | |
| Mucinous or Adenosquamous | 0.7 (0.3-2.1) | 0.57 | | |

Table 5b

| | Hong Kong Validation Cohort | | | |
|---|---|---|---|---|
| | Univariate analysis | | Multivariate analysis[2] | |
| Characteristic | HR (95% CI) | p-value | HR (95% CI) | p-value |
| miR-21 expression[3] n = 111 | | | | |
| Low | 1.0 | | 1.0 | |
| High | 2.3 (1.4-3.9) | 0.002 | 2.3 (1.4-3.9) | 0.002 |
| TNM Stage | | | | |
| I-II | 1.0 | | 1.0 | |
| III-IV | 4.9 (2.5-97) | <0.001 | 4.9 (2.5-98) | <0.001 |
| Age at enrollment | | | | |
| <50 | 1.0 | | | |
| ≧50 | 1.4 (0.8-2.4) | 0.20 | | |
| Sex | | | | |
| Female | 1.0 | | | |
| Male | 1.3 (0.8-2.3) | 0.27 | | |
| Tumor Location | | | | |
| Distal | 1.0 | | | |
| Proximal | 0.7 (0.3-1.4) | 0.27 | | |

TABLE 5-continued

Univariate and Multivariate Cox Regression Analysis of miR-21 Expression Levels and Overall Cancer Survival in Subjects with All Subjects

| | | |
|---|---|---|
| Histology | 1.0 | |
| Adenocarcinoma | | |
| Mucinous or | 1.2 (0.4-3.3) | 0.74 |
| Adenosquamous | | |

MicroRNA expression was measured with miRNA microarrays for the Maryland cohort and with qRT-PCR with the Hong Kong cohort.
[1] All individuals were included in this analysis regardless of tumor histology.
[2] Multivariate analysis used stepwise addition and removal of clinical covariates found to be associated with survival in univariate models (p < 0.10) and final models include only those covariates which were significantly associated with survival (Wald statistic p < 0.05).
[3] High expression in tumors for all miRNAs was defined based on the highest tertile.

MiR-21 Expression Levels and Response to Therapy

Identifying biomarkers associated with a response to adjuvant chemotherapy will allow physicians to better predict the benefits of therapy. To this end, we analyzed associations with miR-21 expression and the response to adjuvant chemotherapy in stage II and III cancer patients. Information on the administration of adjuvant chemotherapy was available for 47 of 65 stage II or III subjects in the Maryland test cohort and all subjects in the Hong Kong validation cohort.

In both cohorts, chemotherapy regimens were primarily fluorouracil-based (in forms of either intravenous 5-fluorouracil or oral drugs including tegafur with uracil [UFT]) with or without Levamisole or Leucovorin. Only subjects with typical adenocarcinoma histology were used for this analysis, leaving 20 of 42 stage II/III individuals who received chemotherapy in the Maryland cohort. For those who received chemotherapy, high miR-21 expression in tumors predicted worse overall survival (p=0.01, Kaplan-Meier log rank test) giving preliminary support that high miR-21 is associated with poor response to adjuvant chemotherapy.

Figure 5A:
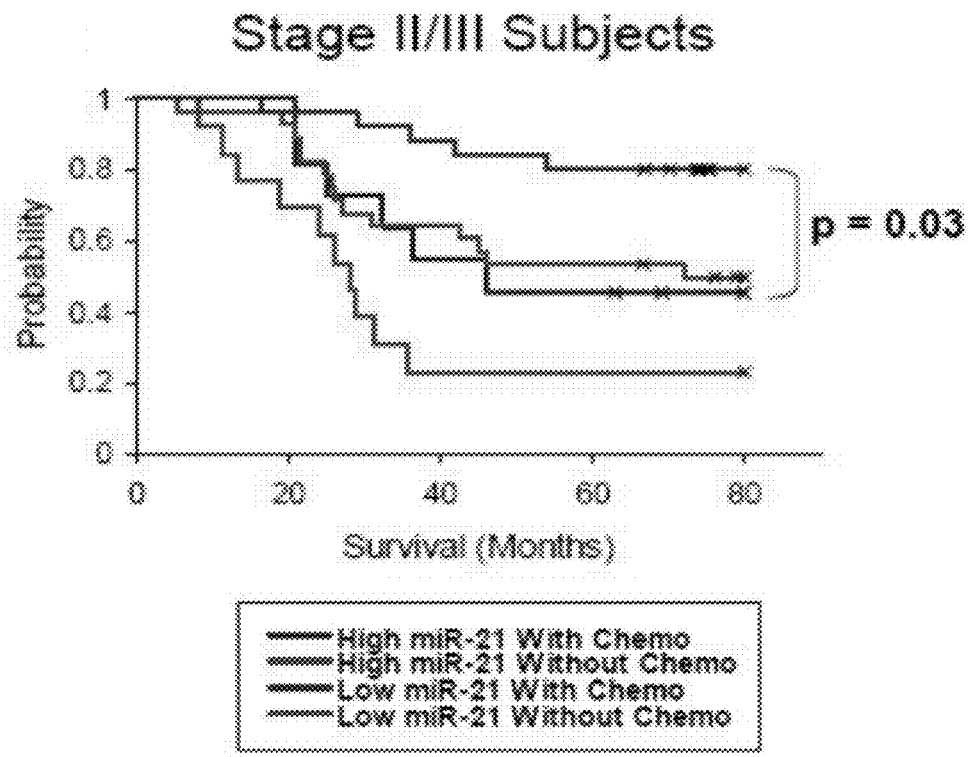
FIGS. 5a, 5b and 5c: High miR-21 expression is associated with a poor response to adjuvant chemotherapy for cases with conventional adenocarcinoma histology. This analysis includes subjects from the validation cohort, excluding subjects with mucinous adenocarcinoma or adenosquamous carcinoma histologies.

For the Hong Kong validation cohort, 77 individuals with stage cancer with typical adenocarcinoma histology were used for this analysis. Stage II/III subjects who received adjuvant chemotherapy had better survival prognosis than those who did not (p=0.02, Kaplan-Meier log rank test). Among those subjects that received adjuvant chemotherapy (n=36), high miR-21 expression in tumors was associated with a poor response to treatment (p=0.03, Kaplan-Meier log rank test), consistent with observations in the Maryland cohort (see FIG. 5a).

Figure 5B:
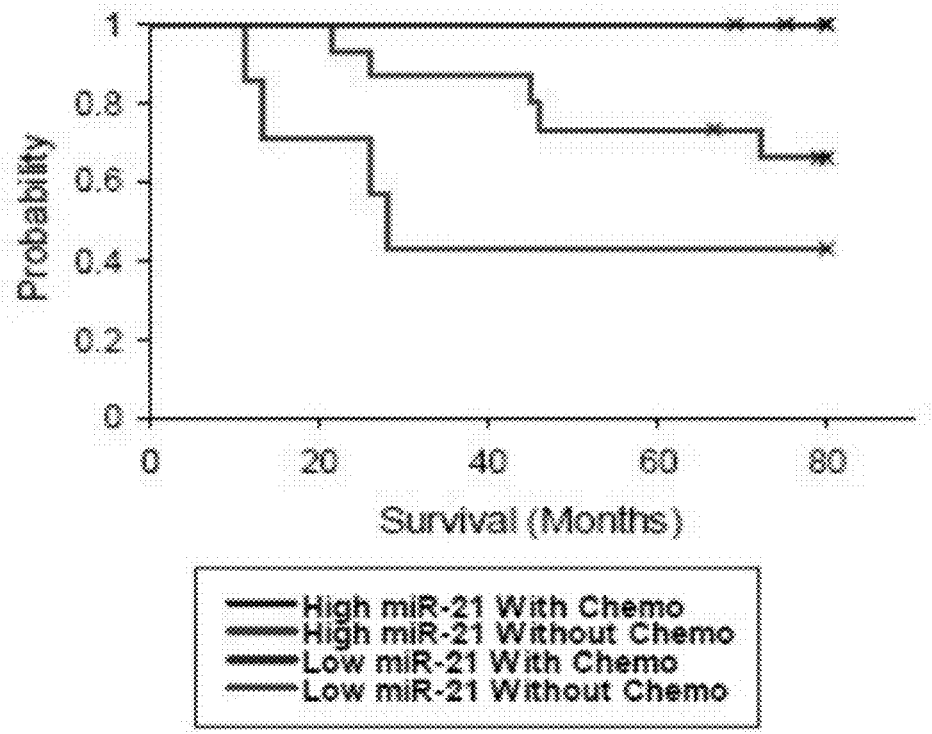
Figure 5C:
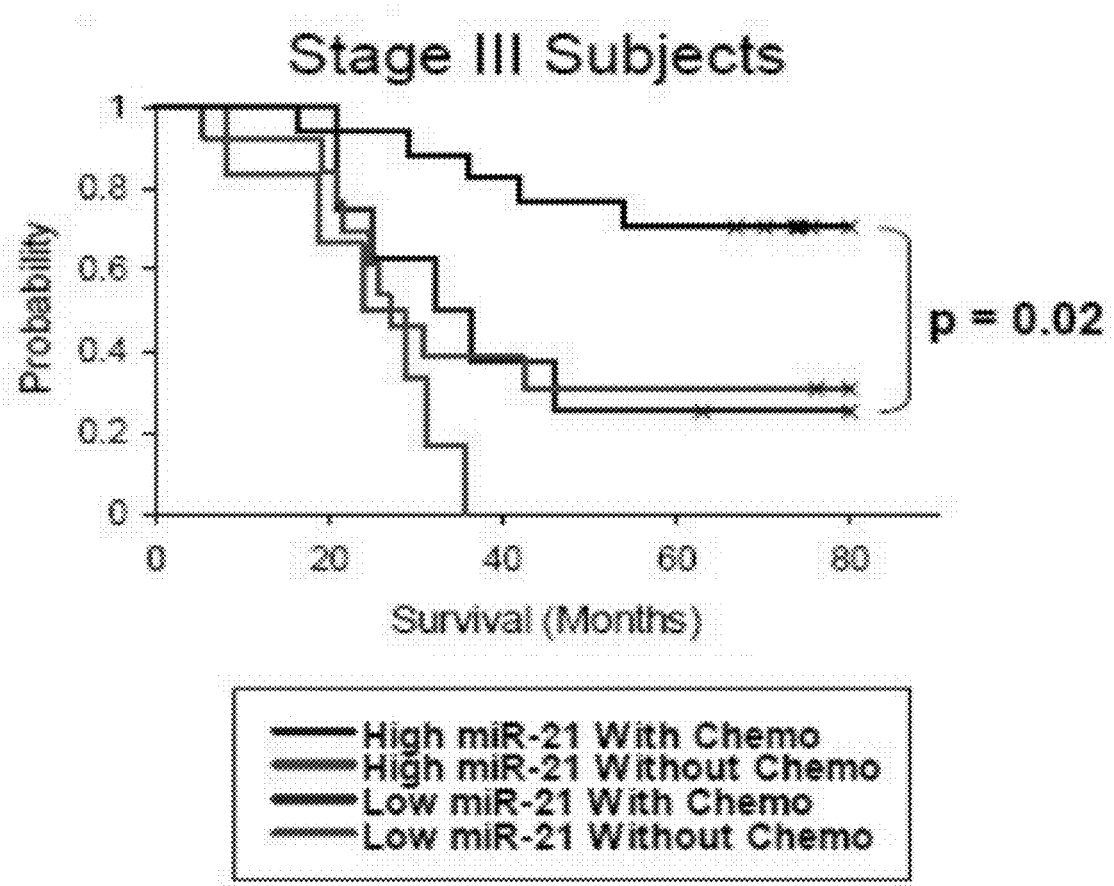

In this cohort, all stage II subjects who received adjuvant chemotherapy (n=11) survived (see FIG. 5b), but for stage III subjects who received adjuvant chemotherapy (n=25), high miR-21 expression was associated with poor survival (p=0.02, Kaplan-Meier log rank test) (see FIG. 5c).

Multivariate Cox regression analysis was used to analyze these observations to show that high miR-21 expression predicted a poor prognosis (HR=3.1 [1.5-6.1]; p=0.001) and receiving chemotherapy was predictive of improved survival outcomes (HR=0.3 [0.1-0.5]; p<0.001) independent of other clinical covariates (Table 6a).

TABLE 6

Univariate and Multivariate Cox Regression Analysis of miR-21 Expression, Receipt of Adjuvant Chemotherapy and Cancer Survival in Stage I/III[1] Subjects with Adenocarcinoma

Table 6a

| | Maryland Test Cohort | | | |
|---|---|---|---|---|
| | Univariate analysis | | Multivariate analysis[2] | |
| Characteristic | HR (95% CI) | p-value | HR (95% CI) | p-value |
| miR-21 expression[3] N = 77 | | | | |
| Low | 1.0 | | 1.0 | |
| High | 2.6 (1.3-5.1) | 0.005 | 3.1 (1.5-6.1) | 0.001 |
| Adjuvant Chemotherapy | | | | |
| Did not receive | 1.0 | | 1.0 | |
| Received | 04. (0.2-0.8) | 0.01 | 0.3 (0.1-0.5) | <0.001 |
| TNM Stage | | | | |
| II | 1.0 | | 1.0 | |
| III | 2.8 (1.3-6.0) | 0.008 | 5.4 (2.4-12) | <0.001 |
| Tumor Location | | | | |
| Distal | 1.0 | | 1.0 | |
| Proximal | 0.3(0.1-1.0) | 0.04 | 0.2 (0.1-0.8) | 0.02 |
| Age at enrollment | | | | |
| <50 | 1.0 | | | |
| ≧50 | 1.6 (0.8-3.1) | 0.20 | | |
| Sex | | | | |
| Female | 1.0 | | | |
| Male | 1.2 (0.6-2.3) | 0.61 | | |

Table 6b

| | Hong Kong Validation Cohort | | | |
|---|---|---|---|---|
| | Univariate analysis | | Multivariate analysis[2] | |
| Characteristic | HR (95% CI) | p-value | HR (95% CI) | p-value |
| miR-21 expression[3] N = 119 | | | | |
| Low | 1.0 | | 1.0 | |
| High | 2.6 (1.5-4.5) | 0.001 | 3.0 (1.7-5.4) | <0.001 |
| Adjuvant Chemotherapy | | | | |
| Did not receive | 1.0 | | 1.0 | |
| Received | 07. (0.4-1.2) | 0.21 | 0.4 (0.2-0.8) | 0.004 |
| TNM Stage | | | | |
| II | 1.0 | | 1.0 | |
| III | 3.2 (1.7-6.1) | 0.001 | 5.2 (2.6-11) | <0.001 |
| Tumor Location | | | | |
| Distal | 1.0 | | 1.0 | |
| Proximal | 0.4 (0.2-0.8) | 0.02 | 0.3 (0.1-0.7) | 0.007 |
| Age at enrollment | | | | |
| <50 | 1.0 | | | |
| ≧50 | 1.4 (0.7-2.5) | 0.32 | | |

TABLE 6-continued

Univariate and Multivariate Cox Regression Analysis of miR-21 Expression, Receipt of Adjuvant Chemotherapy and Cancer Survival in Stage I/III[1] Subjects with Adenocarcinoma Sex Female       1.0
Male         1.3 (0.7-2.2)    0.44

Expression of miRNAs was measured with qRT-PCR.
[1]TNM stage II/III subjects with typical adenocarcinoma histology were included in this analysis.
[2]Multivariate analysis used stepwise addition and removal of clinical covariates found to be associated with survival in univariate models (p < 0.10) and final models include only those covariates which were significantly associated with survival (Wald statistic p < 0.05).
[3]High expression in tumors for all miRNAs was defined based on the highest tertile. Race was not associated with poor prognosis.

Analyses using cancer relapse as an endpoint instead of cancer death resulted in similar associations with high miR-21 expression in tumors predicting a more rapid disease recurrence (data not shown).

Figure 6A:
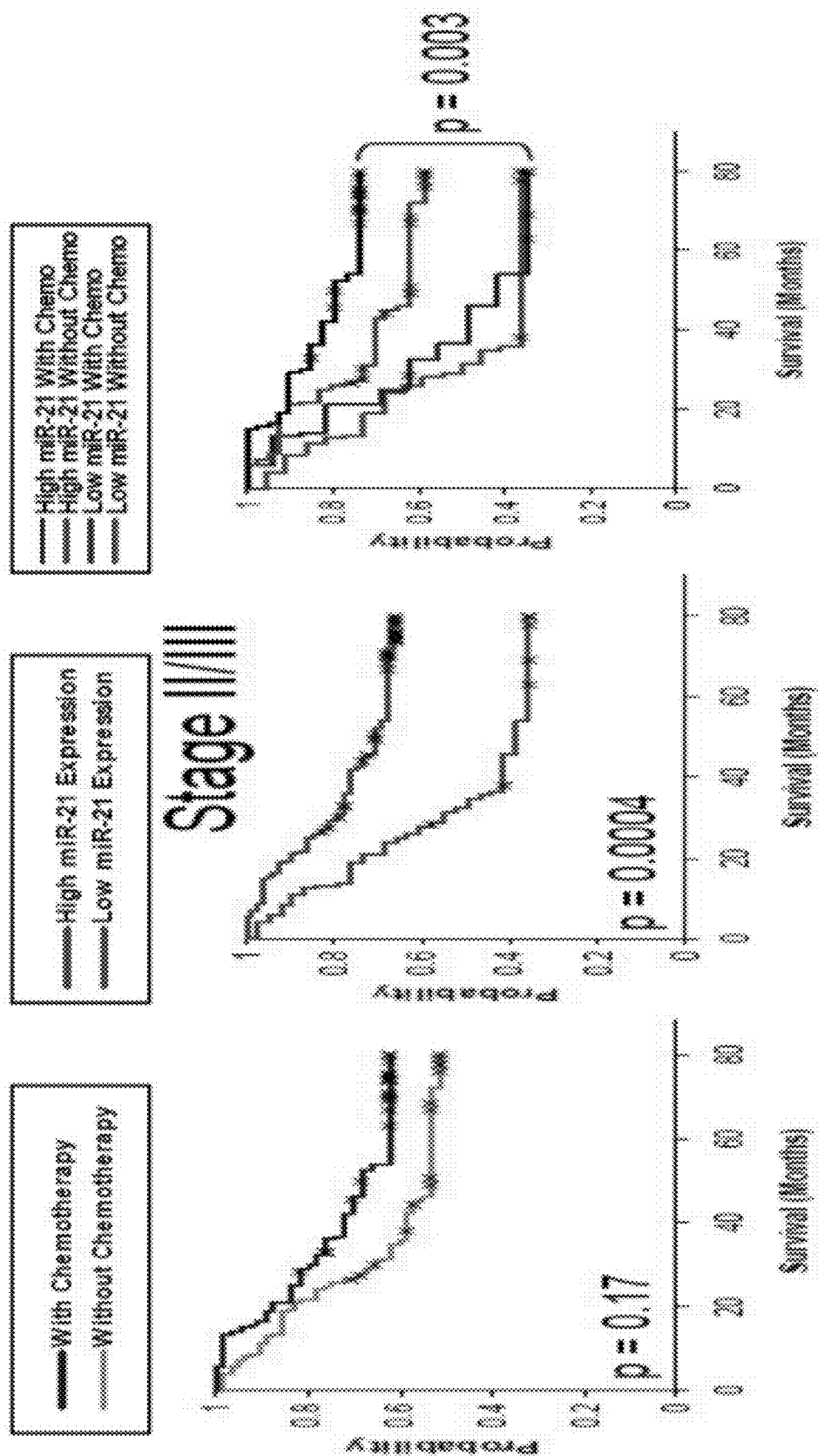
FIGS. 6a, 6b and 6c: Combined analysis of Maryland test cohort and Hong Kong validation cohort examining associations between miR-21 expression in tumors and receipt of adjuvant chemotherapy with prognosis. This analysis includes all TNM stage II/III subjects from both cohorts. Excluded were individuals with mucinous adenocarcinoma or adenosquamous carcinoma histologies. The left column includes Kaplan-Meier plots analyzing the association between receipt of adjuvant therapy and prognosis. The center column includes analysis of the association between high miR-21 expression in tumors and prognosis, and the right column subdivides individuals based on both chemotherapy and miR-21 expression status.
Figure 6B:
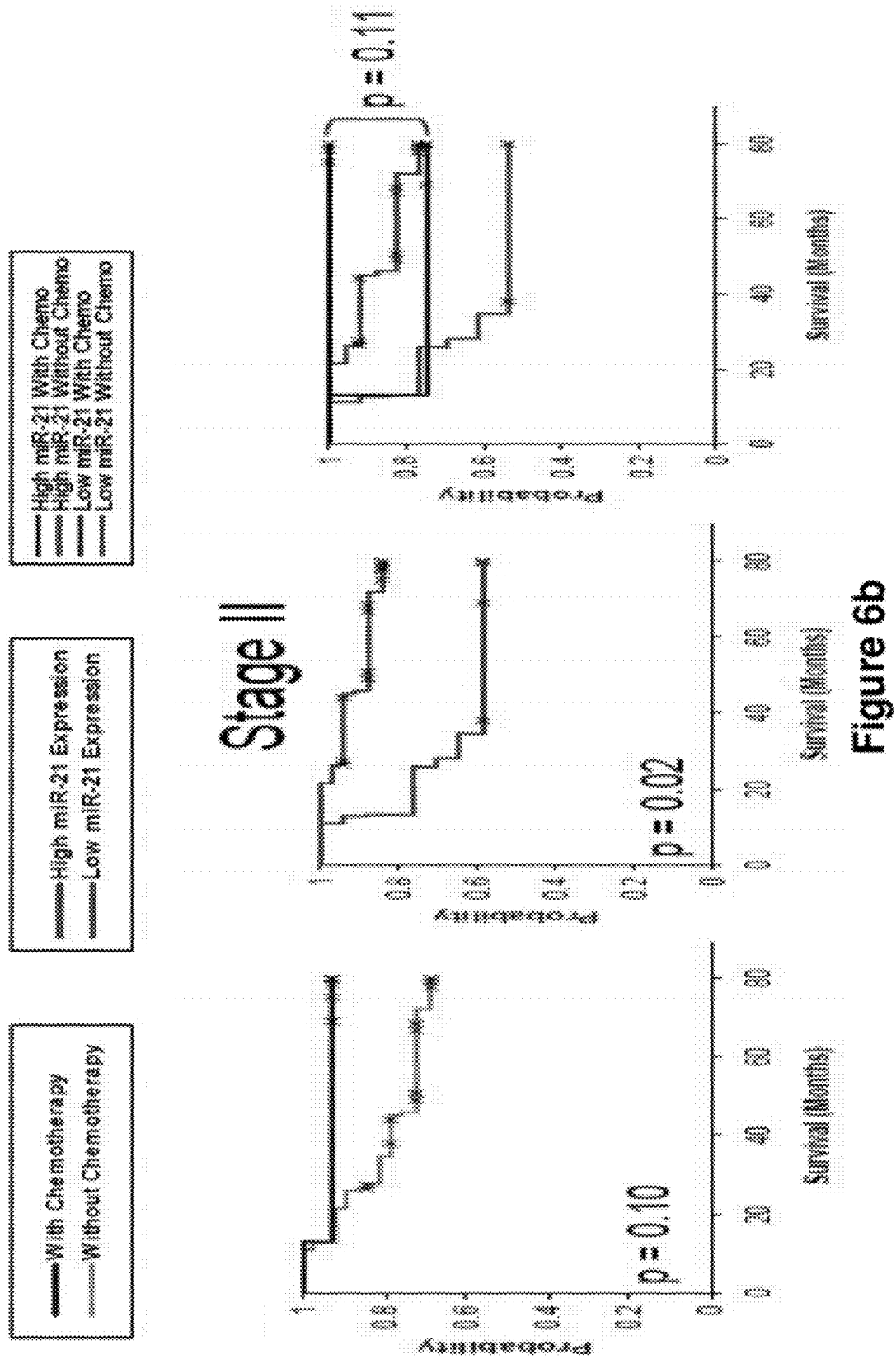
Figure 6C:
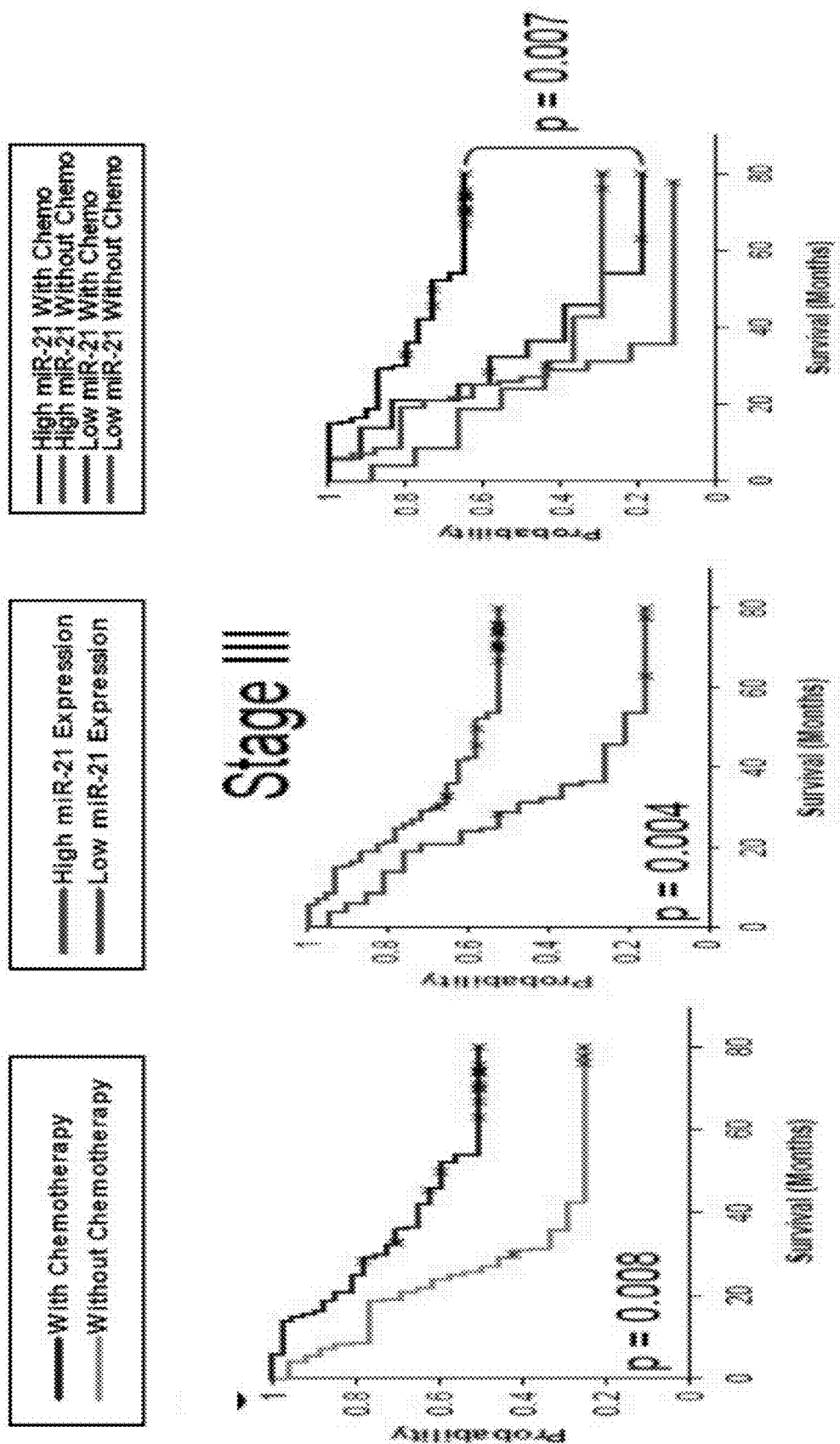

An analysis combining both cohorts resulted in similar associations. Kaplan-Meier analysis demonstrated that high miR-21 expression predicted a poor prognosis in either stage II (p=0.02) or stage III (p=0.004) subjects (See FIG. 6).

High miR-21 expression predicted a poor response to chemotherapy in stage II/III subjects (p=0.003) or in stage III subjects alone (p=0.007). Multivariate Cox regression demonstrated that high miR-21 expression predicted poor prognosis (HR=3.0 [1.7-5.4]; p<0.001) and treatment with adjuvant chemotherapy predicted improved survival (HR=0.4 [0.2-0.8]; p=0.004) independent of other clinical covariates (Table 6b).

Discussion

We analyzed microRNA profiles in colon cancer tissues using two independent cohorts. Thirty-seven microRNAs were differentially expressed in tumor tissues by microRNA microarray analysis. Expression patterns of all five tested microRNAs were validated in the Hong Kong cohort. The discriminatory power of five microRNAs to differentiate between tumor and nontumorous tissue indicates that predictable and systematic changes of microRNA expression patterns occur during tumorigenesis and are likely representative of the majority of sporadic colon adenocarcinomas.

MiR-20a, miR-21, miR-106a, miR-181b and miR-203 were all found to be expressed at higher levels in colon tumors. These changes in microRNA expression patterns may be merely associated with colon cancer or causal to the histologic progression to cancer. There is strong evidence suggesting that changes in microRNA expression patterns promote tumor formation, especially for miR-20a and miR-21. MiR-20a is part of the miR-17-92 polycistronic microRNA cluster.

Overexpression of this cluster enhances cell proliferation in vitro and accelerates tumor formation in animal models. Enforced expression of the miR-17-92 cluster causes increased tumor size and tumor vascularization in mice by negatively regulating the anti-angiogenic Tsp1 protein. Experimental evidence also suggests that increased miR-21 expression promotes tumor development. MiR-21 is expressed at high levels in most solid tumors. Overexpression of miR-21 acts as an anti-apoptotic factor in human glioblastoma cells Inhibition of miR-21 inhibits cell growth in vitro and inhibits tumor growth in xenograft mouse models through an indirect downregulation of the anti-apoptotic factor Bcl-2. Studies in human cell lines have shown miR-21 can also target the tumor suppressor genes PTEN[3] and TPM1. All of these data taken together support a causal role for altered microRNA expression during tumorigenesis.

Adenomas represent a precursor stage of adenocarcinoma. Adenomas express high levels of miR-21. If increased miR-21 expression promotes colon tumor progression, increased expression in adenomas may be an early cellular event in the progression to cancer. Inhibiting miR-21 activity may help prevent tumor promotion in populations at high risk for colon cancer, such as individuals with familial adenomatous polyposis.

Thus, there is presented herein evidence that demonstrates an association with microRNA expression patterns with colon cancer prognosis and response to adjuvant chemotherapy. More advanced tumors express higher levels of miR-21. A robust association with high miR-21 expression in tumors and poor survival was observed in the Maryland test cohort and the Hong Kong validation cohort, separately.

In each cohort, these associations were independent of all other clinical covariates indicating that miR-21 expression may be a useful prognostic indicator, in addition to TNM staging and other clinical parameters, to help identify patients at a higher risk of terminal cancer. These observations were made in two independent cohorts with very different racial and geographical compositions. Therefore, it is likely that our observations are broadly applicable to other populations.

High miR-21 expression in tumors was associated with a poor response to adjuvant chemotherapy in both cohorts. These results can help predict the benefits of therapy in individuals whose miR-21 expression status is known. In addition, if high miR-21 expression is causal to the poor survival of colon cancer patients, antagomirs or other antisense therapeutics that target miR-21 can have therapeutic benefits in subjects with high miR-21 expressing tumors. These may be used in addition to current therapies to improve survival outcomes.

The inventors herein have found systematic differences in microRNA expression patterns between colon tumors and paired nontumorous tissue. High miR-21 expression in tumors predicts poor survival outcome and poor response to adjuvant chemotherapy in two independent cohorts, independent of staging and other clinical covariates suggesting that it may be a useful diagnostic biomarker for colon adenocarcinomas and survival prognosis including response to therapy.

Methods

Tissue Collection and RNA Isolation:

Pairs of primary colon tumor and adjacent nontumorous tissues came from 84 patients recruited from the University of Maryland Medical Center between 1993 and 2002, and from 113 patients recruited from Queen Mary Hospital in Hong Kong between 1991 and 2000. Detailed backgrounds for each tissue donor, including age, gender, clinical staging, tumor location, survival times from diagnosis and receipt of adjuvant chemotherapy have been collected. Tumor histopathology was classified according to the World Health Organization Classification of Tumor system. The adenoma tissue was obtained from the Cooperative Human Tissue Network. This study was approved by the Institutional Review Board of the National Institutes of Health, the Institutional Review Board of the University of Hong Kong/Hospital Authority Hong Kong West Cluster and the Institutional Review Board for Human Subject Research at the University of Maryland.

RNA Isolation and MicroRNA Profiling:

RNA was extracted from tissue using standard TRIZOL (Invitrogen, Carlsbad) methods. MicroRNA microarray profiling was performed as previously described. Briefly, 5 lag of total RNA was labeled and hybridized to each microRNA microarray containing quadruplicates of approximately 400 human microRNA probes. Slides were scanned using a PerkinElmer ScanArray LX5K scanner. qRT-PCR of microRNAs was performed using Taqman MicroRNA assays (Applied Biosystems, Foster City) according to manufacturer's instructions with the 7500 real time RT-PCR system (Applied Biosystems, Foster City). U6B was the normalization control for all qRT-PCR experiments. All assays were performed in duplicate (miR-20a, miR-203) or triplicate (miR-21, miR-106a, miR-181b). qRT-PCR for miR-21, miR-106a and miR-181b was performed by AJS, who was blinded to the survival outcomes and clinical data for members of the validation cohort at that time.

Microarray Analysis:

The data discussed in this publication have been deposited in NCBIs Gene Expression Omnibus (GEO, http://www.ncbi.nlm.nih.gov/geo/) and are accessible through GEO Series accession number GSE7828. LOESS normalized microarray data were imported into BRB array tools 3.5.0 (http://linus.nci.nih.gov/.BRB-ArrayTools.html) and all subsequent microarray analyses were performed with this software.

Microarray analyses were performed. Probes with values missing from >20% of the arrays were removed from the analysis leaving 230 probes. Paired, class comparison analysis identified microRNAs that were differentially expressed in tumors (p<0.001).

To initially search for microRNAs associated with poor survival, tumor/nontumor (T/N) microRNA expression ratios were analyzed in the Maryland cohort using microarray data. TN expression ratios for microRNAs were created by subtracting the $\log_2$ nontumor from the $\log_2$ tumor expression values. MicroRNAs missing >25% of T/N ratios were filtered out leaving 208. T/N expression ratios were dichotomized with the highest tertile classified as high and the lower 2 tertiles classified as low (see Supplemental Methods). This high/low cutoff was used universally throughout this study. Tumor and nontumor microRNA expression levels were batch normalized based on the date of microarray experiments for all analysis of associations with survival.

In Situ Hybridization:

In situ hybridization (ISH) was performed with probes for human miR-21, scramble, and U6 (Exiqon, Woburn) with a modified version of the manufacturer's protocol for formalin-fixed paraffin-embedded (FFPE) tissue written by W. Kloosterman (http://www.exiqon.com/uploads/LNA 52-FFPE miRNA in situj.rotocol.pdf) on human colon tissue. Modifications included the use of polyclonal rabbit anti-DIG/HRP-conjugated antibody and DakoCytomation GenPoint Tyramide Signal Amplication System (DakoCytomation, Carpinteria), and VECTOR® NovaRed™ substrate (Vector Laboratories, Burlingame). Images were taken on an Olympus BX40 microscope using the Olympus DP70 digital camera and DP controller software (Olympus, Champaign).

Statistical Analysis:

Statistical analyses were performed. Wilcoxon matched pairs tests were used to analyze differences in microRNA expression between tumors and paired nontumorous tissue as well as differences between adenoma and paired non-adenoma tissue for all qRT-PCR data. All trend tests reported are nonparametric tests for trend across ordered groups. All Kaplan-Meier analysis was performed with WINSTAT 2001 (R. Fitch Software). Multivariate Cox regression analysis was performed using Intercooled Stata 9.2 (StataCorp LP, College Station). Final multivariate models were based on stepwise addition and removal of clinical covariates found to be associated with poor survival in univariate models (p<0.10). A Wald statistic of p<0.05 was used as criteria for inclusion in final multivariate models. All p-values reported are 2-sided. Hazards ratios are reported with 95% confidence intervals in parentheses. Expression graphs were made using Graphpad Prism 4.0 (Graphpad Software Inc., San Diego).

Additional Microarray Analyses

The microarrays used for this analysis were pin-spotted microRNA microarrays (from the Ohio State University Comprehensive Cancer Center, version 2.0). Intensities of each spot were the median intensities of foreground. Each of the 170 microarrays used for this study contained 11520 spots. All spots where foreground intensity was less than background were reassigned as NA (NA marks missing data spots). All spots flagged as deficient by the scanner were also reassigned as NA. All blank (no oligo) spots with high foreground intensity were reassigned as NA. Each microRNA oligo is represented by quadruplicate spots on these arrays as two distant pairs of two adjacent spots. If there were 0 or 1 NA for an oligo quadruple, and the means of the distant oligo pairs differed by >1 on the $\log_2$ scale, all of the quadruplicate spots were reassigned as NA. If there were 2 NAs for an oligo quadruple and the two non-NA spot intensities differed by >1 on the $\log_2$ scale, all of the quadruplicate spots were reassigned NA. If there were 3 NA spots for a quadruple, the final spot was reassigned as NA. In total, 1,082,689 of 1,958,400 spots were reassigned as NA using these methods. LOESS (Locally Weighted Scatterplot Smoothing) normalization was performed using the R software package. All data was then imported into BRB array tools version 3.5.0 for analysis and all replicate spots were averaged. There were originally 85 pairs (tumor and paired nontumorous tissue) of arrays used. One case that was originally identified as an incident colon carcinoma patient was later found to have been diagnosed as carcinoma in situ and was removed from the analysis leaving the study population of 84 subjects. MicroRNA lists were filtered to include only the 389 human hsa-miR probesets. They were further filtered to remove any probeset missing from more than 25% of the arrays, leaving 230 human microRNA probesets. Paired class comparison analysis was used to identify microRNAs that were differentially expressed between tumor and paired nontumorous tissue. For two microRNAs (miR-181b and miR-338), two independent probes measuring each gave contradictory results with one probe showing higher expression in tumors and one probe showing lower expression in tumors for each microRNA. For each, we discarded the less significant result which designated both miR-181b and miR-388 as enriched in tumors. Additionally, qRT-PCR confirmed that miR-181b was enriched in tumors.

We initially used tumor/nontumor (T/N) expression profiles for each microRNA to search for microRNAs that were associated with poor survival. For this analysis, we decided to dichotomize all expression data with a universal high and low cutoff to look for associations with poor survival. To determine what universal high/low cutoff to use, we dichotomized the T/N expression data three separate ways and determined which method gave the greatest number of significant results in the test cohort. High expression was classified based on higher than median, highest tertile, or highest quartile and we tested associations with these cutoffs with a poor survival using univariate Cox regression analysis. Of the 37 microRNAs that were differentially expressed in tumors, high expression of four were associated with poor survival based on higher than median, five based on highest tertile, and two based on highest quartile (p<0.05, data not shown). Dichotomization based on highest tertile gave the most microRNAs associated with poor survival based on these criteria in the Maryland test cohort; therefore, classification based on highest tertile was used uniformly throughout this study to analyze associations between microRNA expression levels and a poor prognosis in both the Maryland test cohort and the Hong Kong validation cohort.

We used microRNA microarrays to compare miR-21 expression levels in tumors with prognosis. The microarray probe used for this analysis was hsa-miR-21-prec17No1. This analysis required batch normalization of the data based on the date of the microarray experiment. To normalize by date, arrays expressing the highest ⅓ of a given microRNA were classified as high for each day, separately. Up to twelve pairs of tissue were profiled on any given day. For any day in which less than 10 pairs of microarrays were performed, arrays performed on those days were discarded, resulting in the loss of 5 pairs of arrays. These data were then combined together for analysis of associations with survival outcomes. We checked and found no significant differences in the frequency distribution of age, sex, race, tumor location, TNM stage, or cancer survival between groups categorized based on date of microarray experiment (Fisher's exact test).

Statistical Analyses

Cox proportional hazards regression was used to analyze the effect of mir-21 expression levels and other clinical variable on patient survival. Clinical variables included were age, sex, race, tumor location, tumor histology, receipt of adjuvant therapy and TNM staging. For these models, we chose to dichotomized age as age>50 versus age<50 as the recommended screening age for colon cancer is at age 50; tumor location was defined as proximal if tumor was located within or proximal to the splenic flexure and distal if tumor was located within or distal to the descending colon; TNM staging was dichotomized based on metastasic versus nonmetastasic disease resulting in stage I-II versus III-IV. One patient in the Maryland cohort died on the day of surgery resulting in a survival time of 0 months. This case was included in Kaplan-Meier analysis and removed for Cox regression analysis causing the difference in cases between miR-21 expression in tumors for FIG. 2 (n=72) and the number of cases in the Table 4 Cox regression analysis (n=71). Univariate Cox regression was performed on each clinical covariate to examine influence of each on patient survival. Final multivariate models were based on stepwise addition and removal of clinical covariates found to be associated with poor survival in univariate models (p<0.10). A Wald statistic of p<0.05 was used as criteria for inclusion in final multivariate models. The most parsimonious Cox regression model was used for the final multivariate model.

Example 2

Initial Results mrNAs are Differentially Expressed in Colon Tumors

We analyzed miRNA profiles of 85 pairs of cancerous and adjacent non-cancerous colon tissues using miRNA microarrays. We found that miRNA expression profiles of tumors were quite different than normal tissues suggesting that miRNAs may play significant roles in colon carcinogenesis. Paired class comparison analysis identified 27 independent miRNAs that were differentially expressed in these tumors (Table 7).

TABLE 7

27 miRNAs are differentially expressed in colon tumors compared to paired, normal tissue. 27 miRNAs were found to be differentially expressed in tumors using paired class comparisons analysis in BRB array tools 3.4. A significance value of $p < 0.001$ was used as the criteria for differentially expressed which resulted in an estimated false discovery rate of 0.08%. Up refers to miRNAs that were expressed at higher levels in tumors while down indicates that miRNA levels were lower in tumors.

|  | MicroRNA | Up/Downregulated | P-Value |
|---|---|---|---|
| 1 | miR-331 | Down | 1.00E−07 |
| 2 | miR-21 | Up | 1.00E−07 |
| 3 | miR-34b | Down | 2.00E−07 |
| 4 | miR-342 | Down | 2.00E−07 |
| 5 | miR-215 | Down | 2.20E−05 |
| 6 | miR-371 | Down | 7.00E−07 |
| 7 | miR-373 | Down | 6.30E−06 |
| 8 | miR-192 | Down | 7.70E−06 |
| 9 | miR-148b | Down | 1.03E−05 |
| 10 | miR-138 | Down | 1.49E−05 |
| 11 | miR-301 | Down | 1.85E−05 |
| 12 | miR-338 | Down | 2.63E−05 |
| 13 | miR-153 | Down | 2.67E−05 |
| 14 | miR-129 | Down | 3.20E−05 |
| 15 | miR-222 | Up | 9.08E−05 |
| 16 | miR-346 | Up | 0.000126 |
| 17 | miR-204 | Up | 0.000244 |
| 18 | miR-181 b | Up | 0.000263 |
| 19 | let-7a-2 | Down | 0.000272 |
| 20 | miR-106a | Up | 0.000305 |
| 21 | miR-093 | Up | 0.000334 |
| 22 | miR-34c | Down | 0.000341 |
| 23 | miR-219 | Up | 0.000352 |
| 24 | miR-019b | Up | 0.000364 |
| 25 | miR-210 | Up | 0.000389 |
| 26 | miR-185 | Up | 0.000516 |
| 27 | miR-1 | Down | 0.00064 |

The false discovery rate, to account for the multiple comparisons testing, was approximately 0.8% indicating that most, if not all of these miRNAs are differentially expressed and not the result of multiple comparisons testing. Eleven miRNAs were found to have elevated expression levels in tumors while 16 miRNAs were found to be reduced in tumors. Additionally, miRNA profiles could be used to predict whether or not the tissue was tumor or non-tumor with 92% accuracy. Based on 2000 random permutations, the probability of these predictions occurring by random chance was extremely low (p<0.0005). These results show that there are systematic differences in mi RNA expression profiles between tumors and normal tissue indicating that miRNA expression profiles become altered during colon carcinogenesis.

Global miRNA Expression Profiles Predict Colon Cancer Survival Prognosis

Figure 7A:
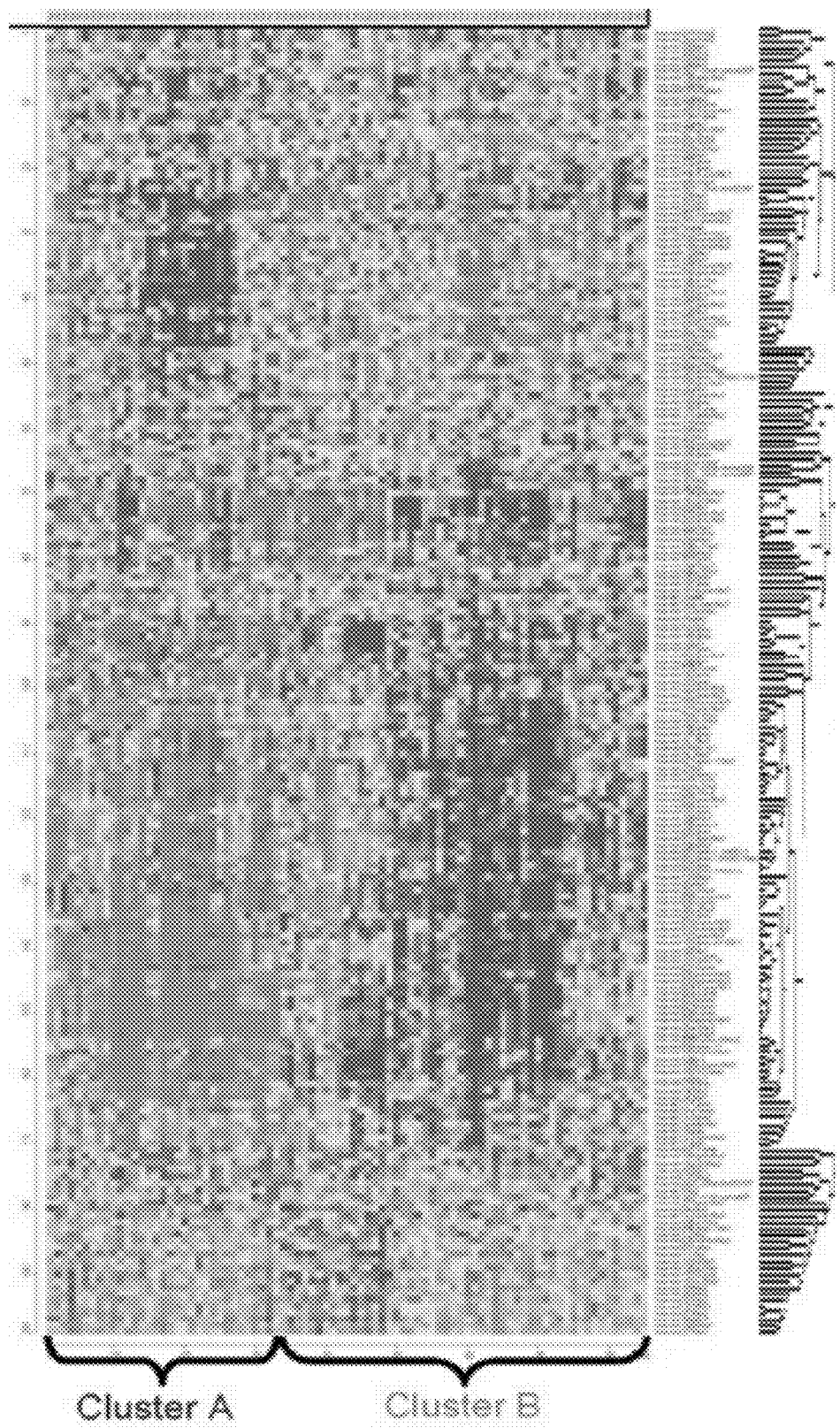
FIGS. 7a-7c. Global miRNA profiles are associated with clinical TNM staging and survival prognosis. Hierarchical clustering of miRNA TIN ratios resulted in forming two groups arbitrarily named group A and group B. The resulting HEAT map and cluster assignments are shown in FIG. 7a. These two groups were composed of individuals with significantly different survival prognoses for TNM staging with group B individuals more likely to be diagnosed as either stage III or IV compared to group A individuals (FIG. 7b). Kaplan-Meier analysis shows that Group B individuals also have a worse survival prognosis (FIG. 7c).
Figure 7B:
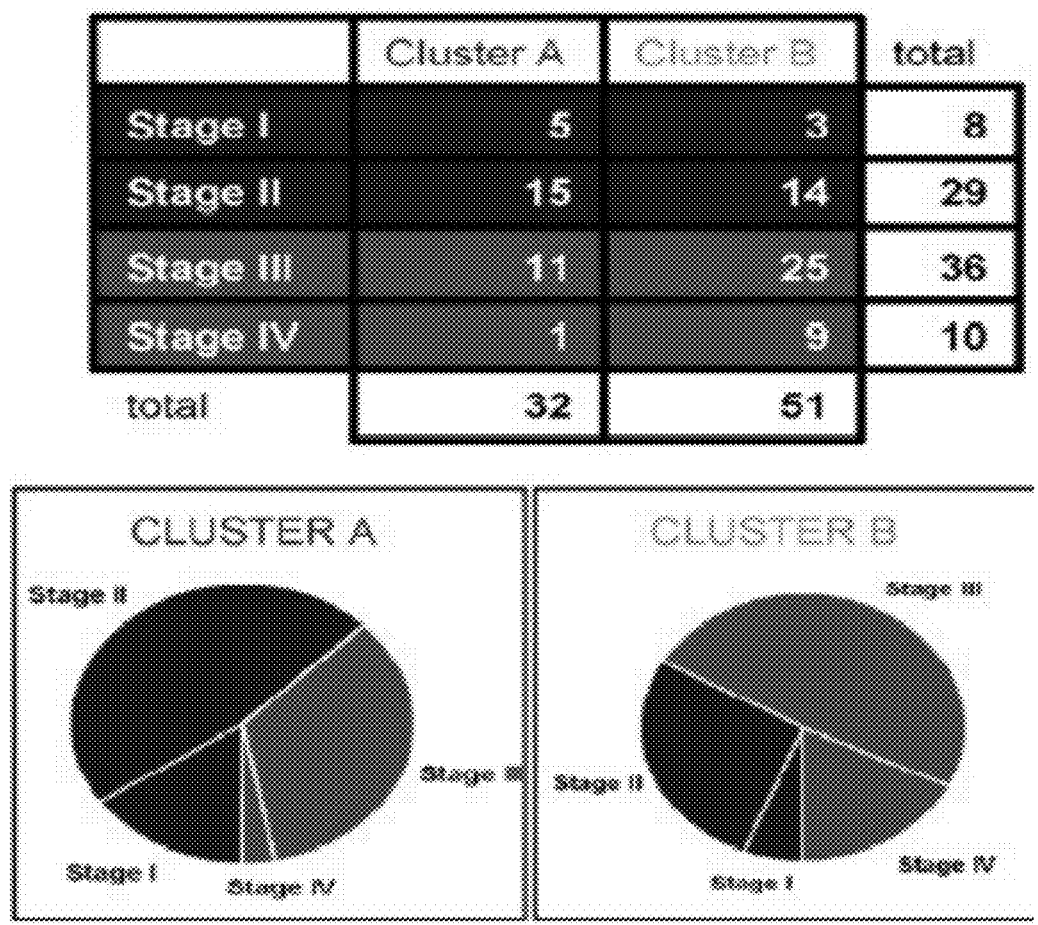

We determined whether miRNA expression profiles predict patient survival. For this analysis we calculated the tumor versus normal miRNA expression ratios (TIN ratio) for each miRNA for every individual. Unsupervised hierarchical clustering of all miRNA TIN ratios grouped individuals into two groups arbitrarily labeled group A and group B (FIG. 7).

Figure 1G:
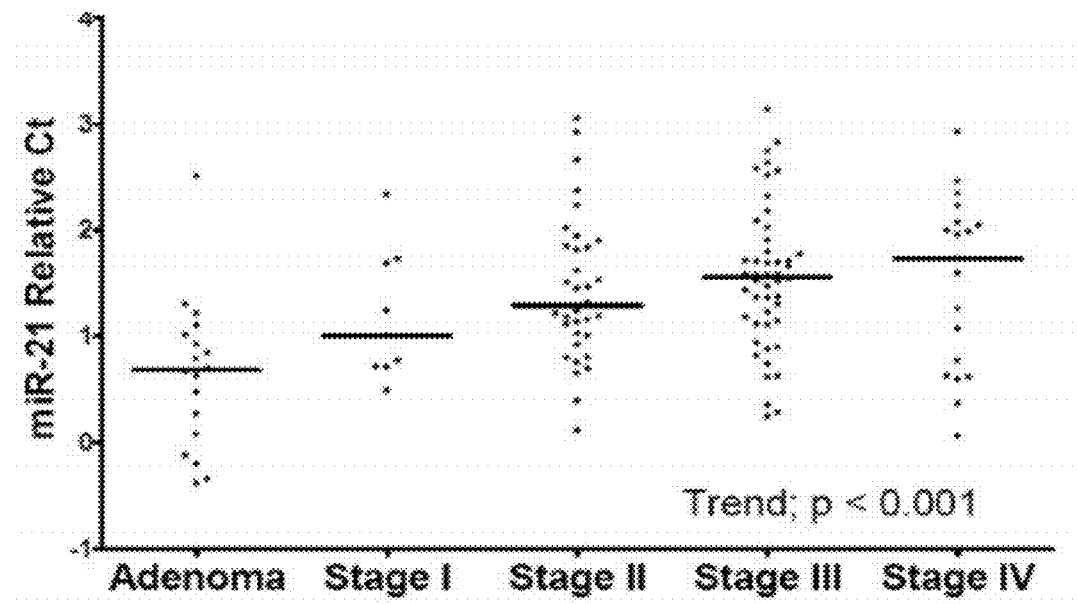
Figure 7C:
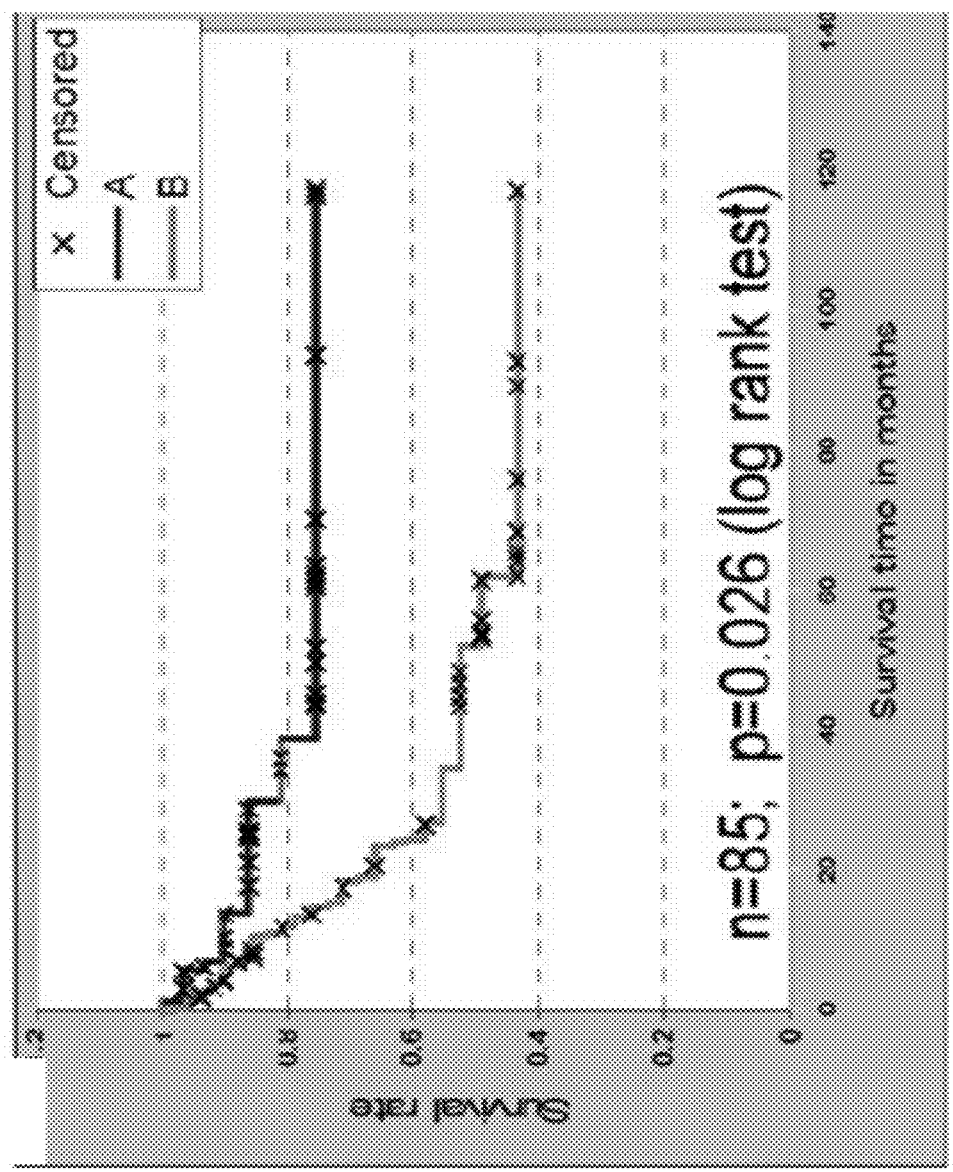

These two groups differ significantly in both clinical staging (p=0.009; FIG. 1b) and survival prognosis (p=0.026; FIG. 7c).

This indicated that global miRNA profiles are predictive of clinical staging and more importantly, survival prognosis.

Univariate and multivariate Cox regression analysis was used to interrogate this relationship in more detail (Table 8).

TABLE 8

Cox Regression Analysis of global miRNA Profiles
Univariate (above) and multivariate (below) Cox regression analyses
were performed to show that individuals classified in miRNA
group B were at higher risk of dying of colon cancer.
Neither age, gender or race was significant contributors to
survival risk. For the purposes of these analyses, age was
dichotomized into greater than or less than 50 and race
dichotomized into African American (AA) and Caucasian.

| Variable | HR (95% CI) | p value |
|---|---|---|
| Univariate Analysis | | |
| Cluster B/A | 2.6 (1.0-6.3) | 0.042 |
| age ≧ 50/age < 50 | 0.62 (0.14--2.7) | 0.53 |
| male/female | 1.4 (0.48-4.0) | 0.54 |
| AA/Caucasian | 1.1 (0.83-2.3) | 0.83 |
| Multivariate, adjusting for age, gender and race | | |
| Cluster B/A | 2.7 (1.1-6.8) | 0.034 |
| age ≧ 50/age < 50 | 0.49 (0.11--2.2) | 0.35 |
| male/female | 1.5 (0.52-4.4) | 0.45 |
| AA/Caucasian | 1.0 (0.45-2.2) | 0.99 |

Group B individuals were to have a significantly higher risk of dying from colon cancer (hazard ratio [HR]=2.6 (p=0.04). This risk remained significantly high after adjusting for age, ethnicity and gender (HR=2.7; p=0.03). These results demonstrate the potential for using miRNA profiles of colon tumors to predict prognosis. These results suggest that miR-NAs may also play a role in colon carcinogenesis.

Profiles of miR-21, miR-106a, miR-181b, miR-16b, miR-203, let-7g, miR-29a, miR-103-2 and miR-10a Predict Colon Cancer Prognosis We identified individual miRNAs whose expression levels were predictive of colon cancer prognosis. We used Kaplan Meier survival plots and multivariate Cox regression analysis on TIN ratios to identify miRNA expression patterns that were associated with poor survival prognosis. BRB array tools were used to identify TIN ratios correlated with poor survival (data not shown). We chose to analyze these miRNAs in further detail. We also analyzed any miRNA that was differentially expressed in tumors (p<0.01). TIN ratios for each individual were dichotomized based on median or highest quartile TIN ratios. We also removed any miRNA from the analysis where TIN ratios were missing in greater than 18 individuals. We identified at least 9 miRNAs, including miR-21, miR-106a, miR-181b, miR-16h, miR-203, let-7g, miR-29a, miR-103-2 and miR-10a whose TIN ratios are predictive of colon cancer prognosis (FIG. 8, Table 9).

COX Regression Analysis of TIN Ratios for Individual miRNAS.

Univariate and multivariate Cox regression analyses were performed to show that TIN ratios of individual miRNAs could by used to classify individuals at higher risk of dying of colon cancer. TIN ratios for these 9 miRNAs were significant predictors of survival prognosis independent of TNM staging, age, gender and race. Note that High/Low distinctions for miR-16b, miR-21, miR-29a, miR-103-2, miR-106a and miR-203 were classified based on median TIN ratio values while let-7g, miR-10a and miR-181b were classified based on highest quartile TIN ratios.

TABLE 9

Cox regression analysis of TIN ratios for individual miRNAs

| Variable | HR (95% CI) | p = | n |
|---|---|---|---|
| Univariate analysis | | | |
| miR-21 High/Low | 3.0 (11.3-7.0) | 0.01 | 80 |
| Multivariate analysis | | | |
| miR-21 High/Low | 2.8 (1.2-6.8) | 0.02 | |
| age ≧ 50/age < 50 | 0.46 (0.10-2.1) | 0.32 | |
| male/female | 3.1 (0.9-11.0) | 0.07 | |
| AA/Caucasian | 1.2 (0.5-2.7) | 0.66 | |
| Stage III-IV/Stage I-II | 4.4 (1.6-11.9) | 0.004 | |
| Univariate analysis | | | |
| miR-181b High/Low | 3.4 (1.6-7.5) | 0.002 | 78 |
| Multivariate analysis | | | |
| miR-181b High/Low | 3.3 (1.3-8.2) | 0.01 | |
| age ≧ 50/age < 50 | 0.39 (0.08-1.8) | 0.23 | |
| Male/female | 2.2 (0.7-7.2) | 0.17 | |
| AA/Caucasian | 1.1 (0.5-2.5) | 0.82 | |
| Stage III-IV/Stage I-II | 3.1 (1.2-8.1) | 0.02 | |
| Univariate analysis | | | |
| let-7g High/Low | 2.7 (1.3-5.9) | 0.01 | 84 |
| Multivariate analysis | | | |
| let-7g High/Low | 2.5 (1.1-5.5) | 0.03 | |
| age ≧ 50/age < 50 | 0.5 (0.1-2.4) | 0.39 | |
| Male/female | 1.5 (0.5-4.4) | 0.50 | |
| AA/Caucasian | 1.3 (0.6-2.9) | 0.50 | |
| Stage III-VI/Stage I-II | 3.6 (1.4-9.2) | 0.006. | |
| Univariate analysis | | | |
| miR-103-2 High/Low | 2.5 (1.1-5.6) | 0.03 | 81 |
| Multivariate analysis | | | |
| miR-103-2 High/Low | 3.1 (1.3-7.5) | 0.01 | |
| age ≧ 50/age < 50 | 0.5 (0.1-2.2) | 0.36 | |
| male/female | 1.6 (0.6-4.9) | 0.38 | |
| AA/Caucasian | 0.8 (0.4-1.9) | 0.69 | |
| Stage III-IV/Stage I-II | 4.4 (1.7-11.1) | 0.002 | |
| Univariate analysis | | | |
| miR-16b High/Low | 4.6 (1.7-12.5) | 0.003 | 69 |
| Multivariate analysis | | | |
| miR-16b High/Low | 5.1 (1.8-15.9) | 0.003 | |
| age ≧ 50/age < 50 | 0.4 (0.08-1.7) | 0.20 | |
| male/female | 3.2 (0.8-1.7) | 0.12 | |
| AA/Caucasian | 0.9 (1.9-22.4) | 0.003 | |
| Stage III-IV/Stage I-II | 6.5 (1.9-22.4 | 0.003 | |
| Univariate analysis | | | |
| miR-106a High/Low | 2.6 (1.1-6.1) | 0.01 | 82 |
| Multivariate analysis | | | |
| miR-106a High/Low | 2.4 (1.0-5.7) | 0.05 | |
| age ≧ 50/age < 50 | 0.54 (0.11--2.5) | 0.44 | |
| male/female | 1.8 (0.5-6.5) | 0.34 | |
| AA/Caucasian | 1.1 (0.5-2.5) | 0.84 | |
| Stage III-IV/Stage I-II | 5.4 (1.8-16.0) | 0.002 | |
| Univariate analysis | | | |
| miR-203 High/Low | 3.8 (1.4-10.5) | 0.01 | 57 |
| Multivariate analysis | | | |
| miR-203 High/Low | 3.2 (1.1-9.4) | 0.03 | |
| age ≧ 50/age < 50 | 1.0 (0.1--8.1) | 0.97 | |
| male/female | 1.4 (0.4-5.1) | 0.61 | |
| AA/Caucasian | 0.9 (0.4-2.3) | 0.83 | |
| Stage III-IV/Stage I-II | 3.9 (1.3-11.8) | 0.02 | |
| Univariate analysis | | | |
| miR-29a High/Low | 3.1 (1.3-7.3) | 0.01 | 77 |

TABLE 9-continued

Cox regression analysis of TIN ratios for individual miRNAs

| Variable | HR (95% CI) | p = | n |
|---|---|---|---|
| Multivariate analysis | | | |
| miR-29a High/Low | 3.2 (1.3-7.9) | 0.01 | |
| age ≧ 50/age < 50 | 0.5 (0.1--2.2) | 0.35 | |
| male/female | 2.2 (0.6-7.4) | 0.22 | |
| AA/Caucasian | 0.9 (0.4-2.1) | 0.76 | |
| Stage III-IV/Stage I-II | 4.5 (1.7-12.2) | 0.003 | |
| Univariate analysis | | | |
| miR-10a High/Low | 2.7 (1.3-5.7) | 0.01 | 84 |
| Multivariate analysis | | | |
| miR-10a High/Low | 3.5 (1.5-7.8) | 0.003 | |
| age ≧ 50/age < 50 | 0.4 (0.1--1.9) | 0.26 | |
| male/female | 1.7 (0.6-5.0) | 0.34 | |
| AA/Caucasian | 1.0 (0.45-2.3) | 0.98 | |
| Stage III-IV/Stage I-II | 4.9 (1.9-12.2) | 0.001 | |

MiR-21 expression is elevated in tumors (Table 7). The miR-21 TIN ratios are also associated with clinical staging and survival prognosis for colon cancer patients as well (Table 9, FIG. 8a).

There was a trend that individuals with more advanced TNM staging have higher TIN ratios (p=0.034). TIN ratios were dichotomized based on median values for each of the 80 individuals with data. Individuals with high miR-21 TIN expression ratios had a worse survival prognosis based on Kaplan Meier analysis (p=0.004) suggesting that tumors expressing high levels of miR-21 is predictive of poor prognosis. These results were further analyzed with Cox regression analysis.

Individuals with high TIN ratios of miR-21 were at higher risk with both univariate (HR=3.0; p=0.01) and multivariate (HR=2.8; p=0.02) analysis adjusting for age, gender, race and TNM staging (Table 9).

This result suggested that miR-21 expression levels can be useful as prognostic prediction methods and can provide more predictive value for survival prognosis than TNM staging alone. miR-21 has been found to be differentially expressed in many tumor types.

Studies have also demonstrated that high levels of miR-21 can lead to an inhibition of apoptosis in glioblastoma cells while inhibition of miR-21 can lead to increased cell proliferation in HeLa cells.

The inventors herein discovered that miR-21 is now believed to be contributing to colon carcinogenesis in a similar manner.

Figure 8A:
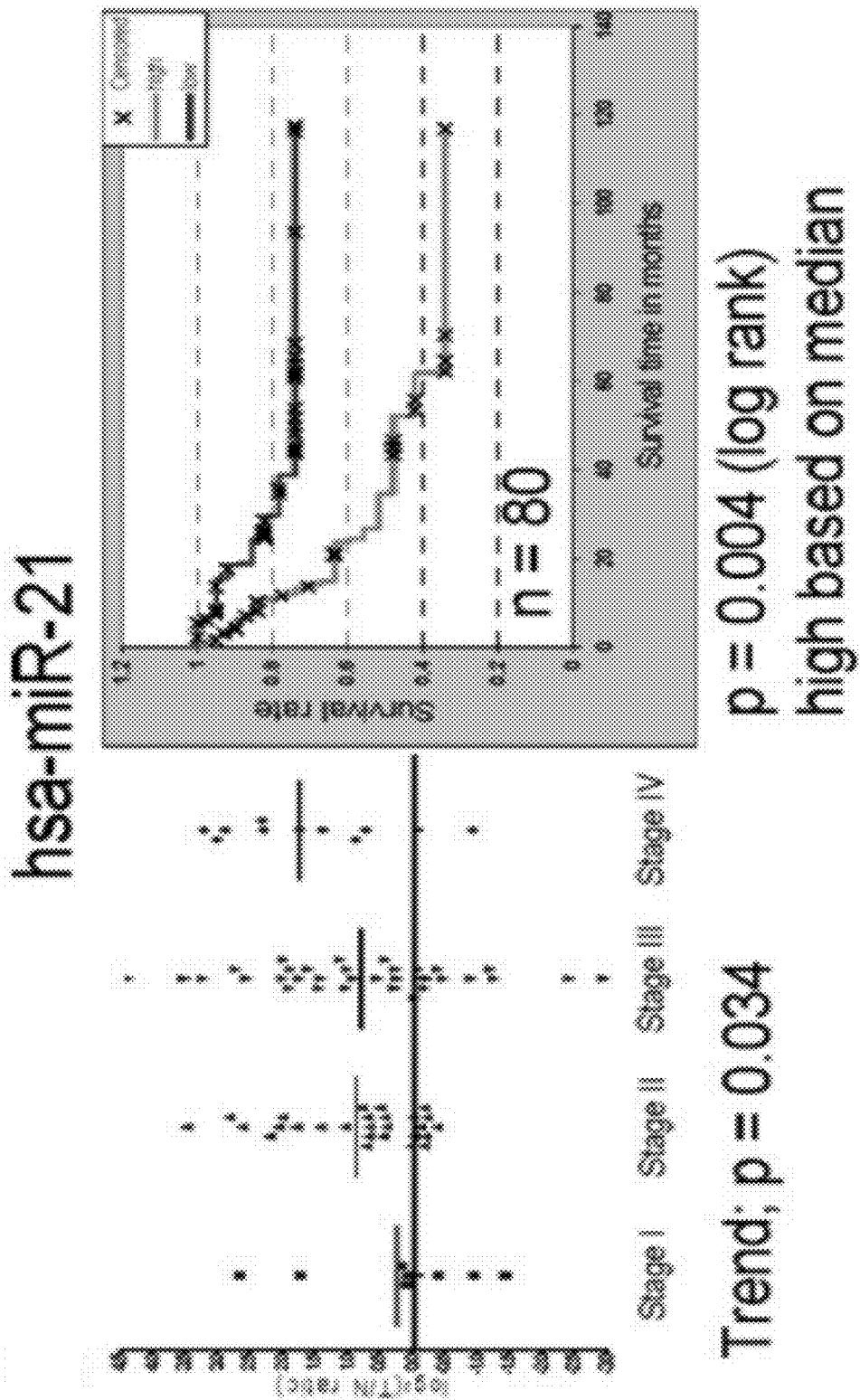
FIGS. 8a-8i. TIN ratios of individual miRNAs are predictive of survival prognosis. Displayed here are graphs showing TIN ratios by TNM staging (left) and Kaplan-Meier analysis (right) for each of these 9 miRNAs. The Y axis (TIN ratio by TNM staging graphs) indicates the log(2) transformed TIN ratio for each individual while the Y axis groups individuals by TNM staging (I, II, III or IV). The significance values shown are the result of a nonparametric test for trend of average TIN ratio values across individuals grouped by staging. Kaplan-Meier plots include all individuals with TIN ratio data for that particular miRNA. We found that TIN ratios were associated with both clinical staging and survival prognosis.
Figure 8B:
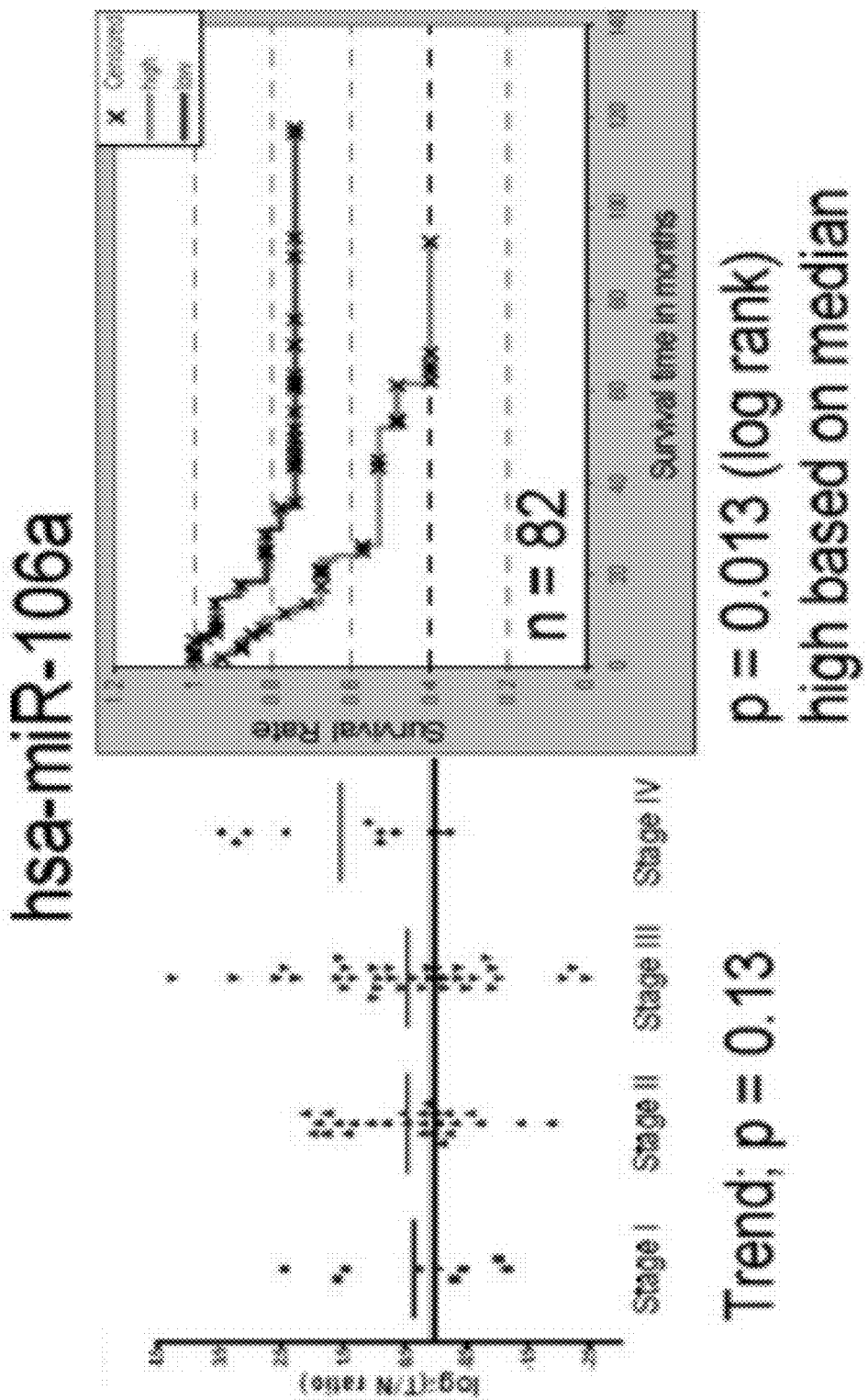
Figure 8C:
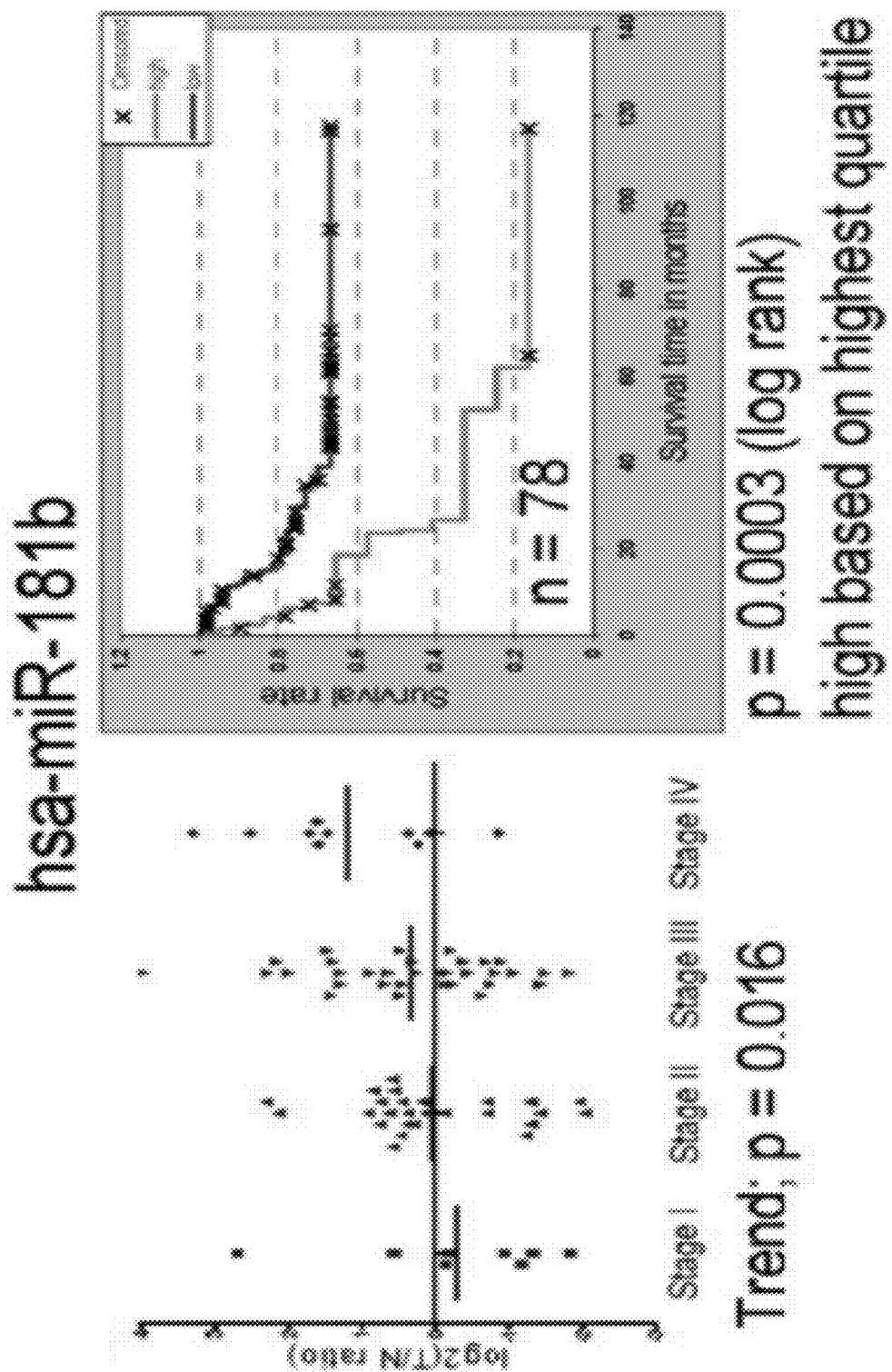
Figure 8D:
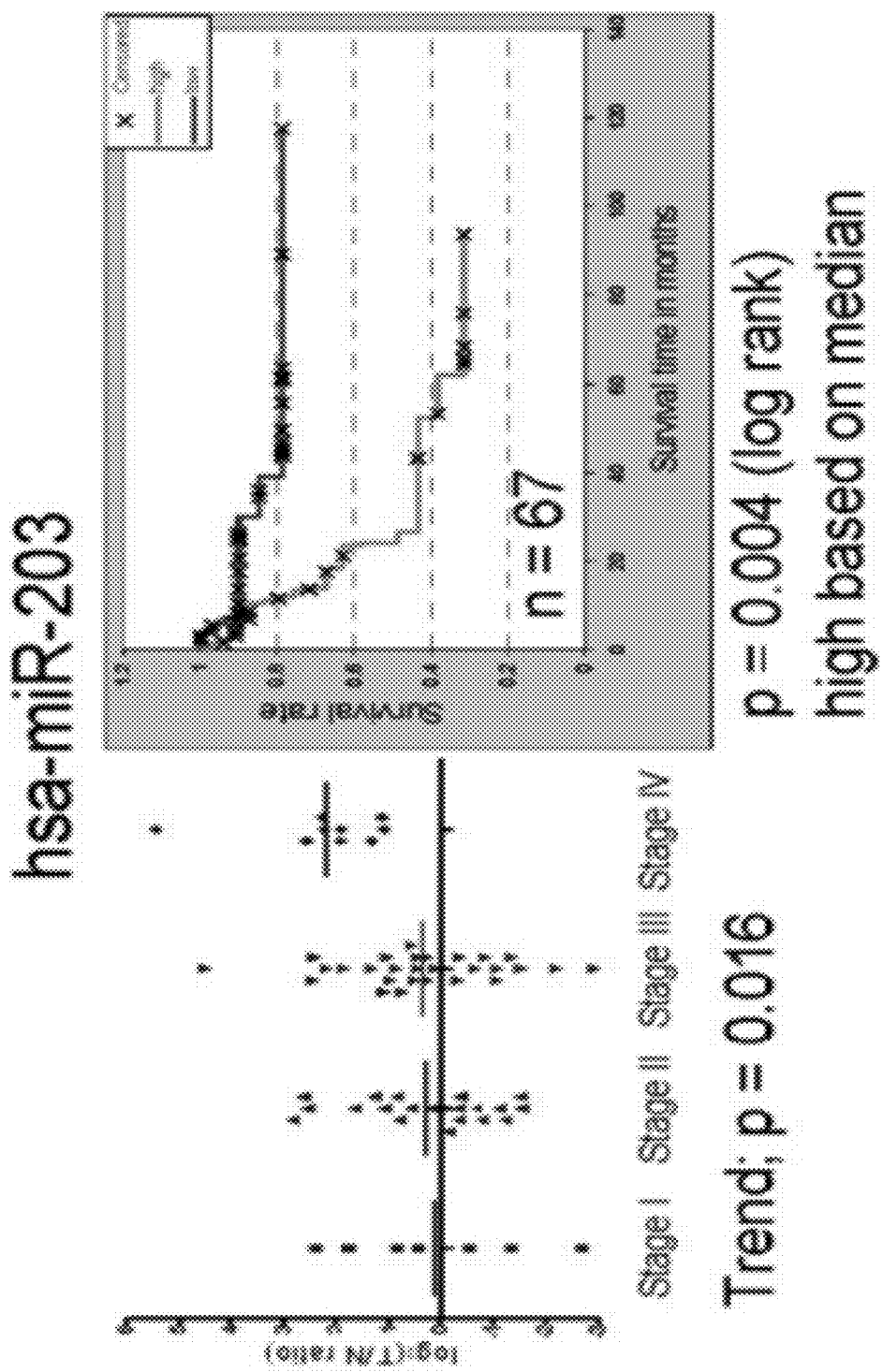
Figure 8E:
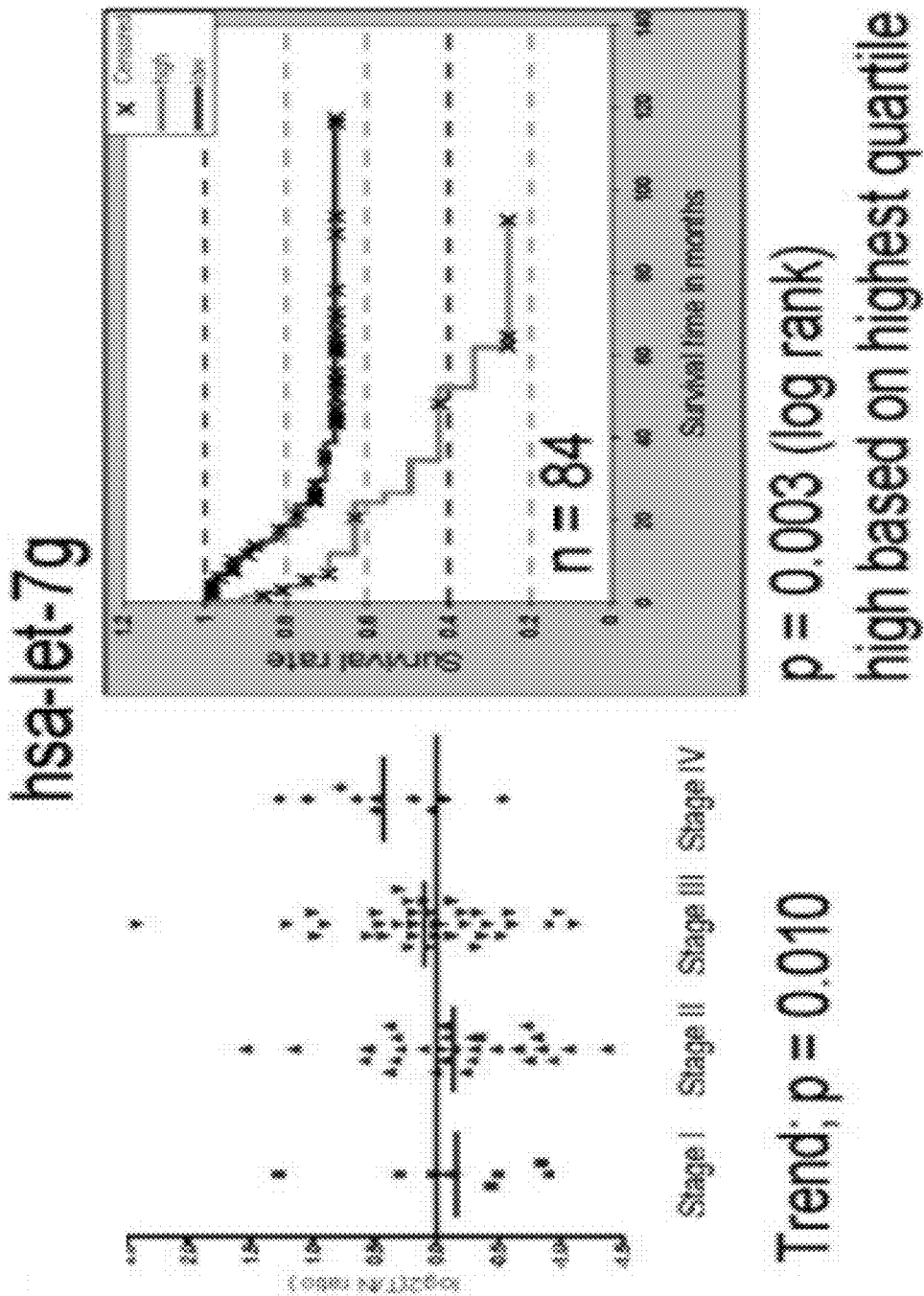
Figure 8F:
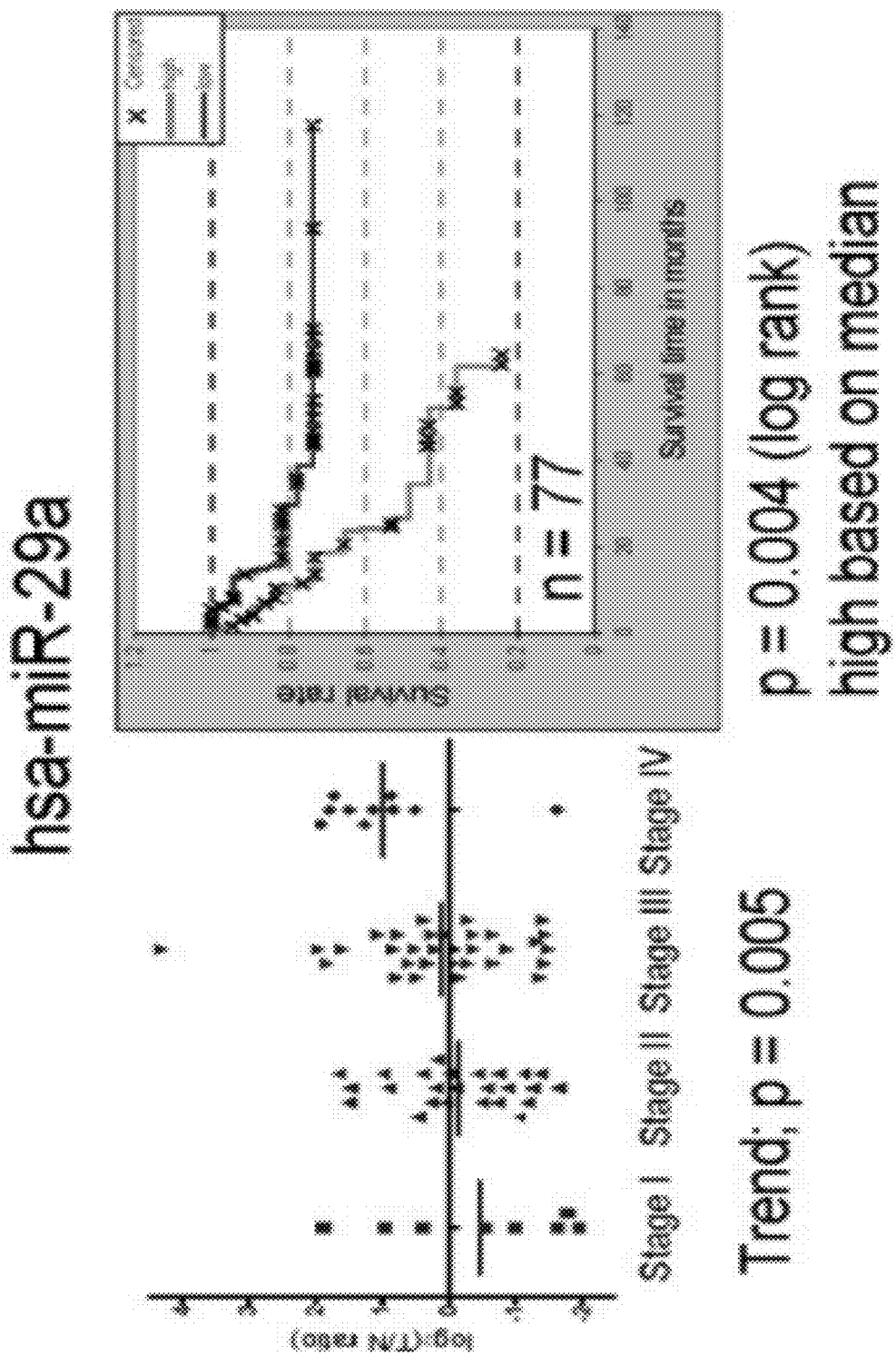
Figure 8G:
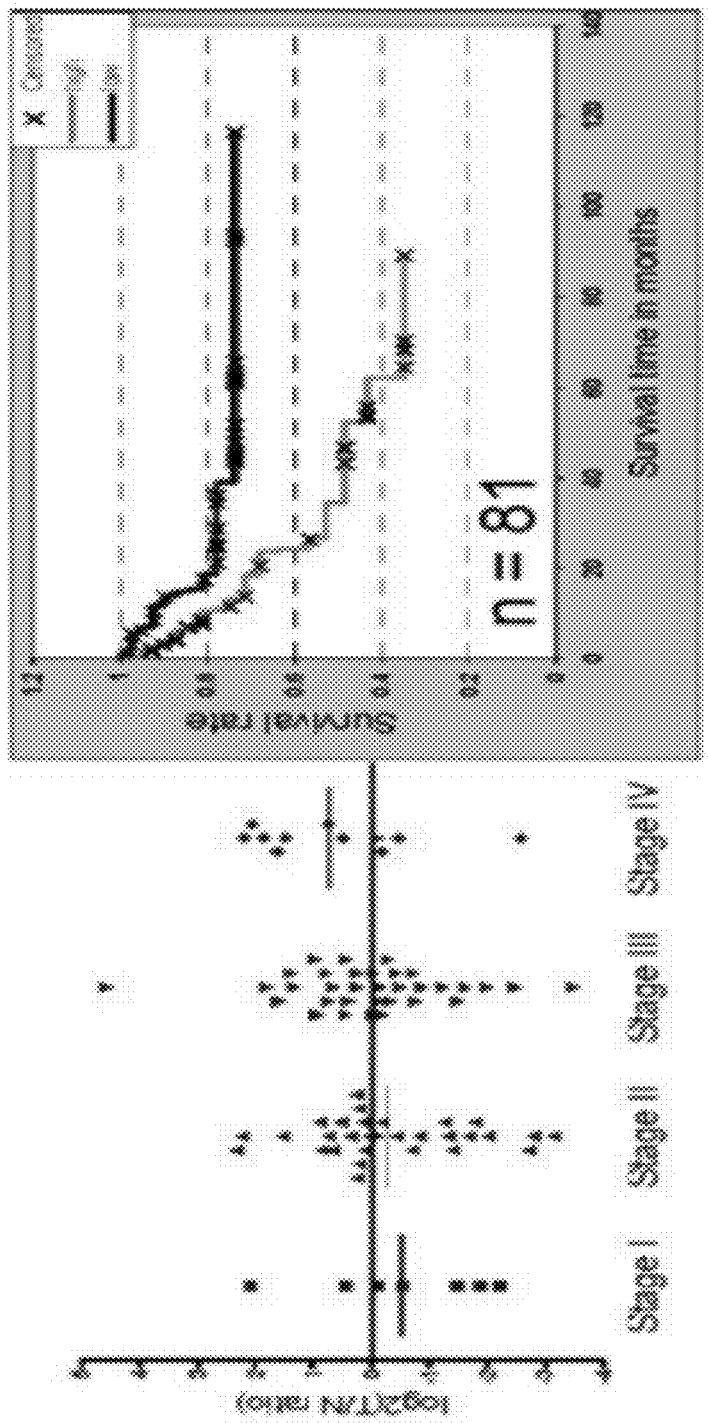
Figure 8H:
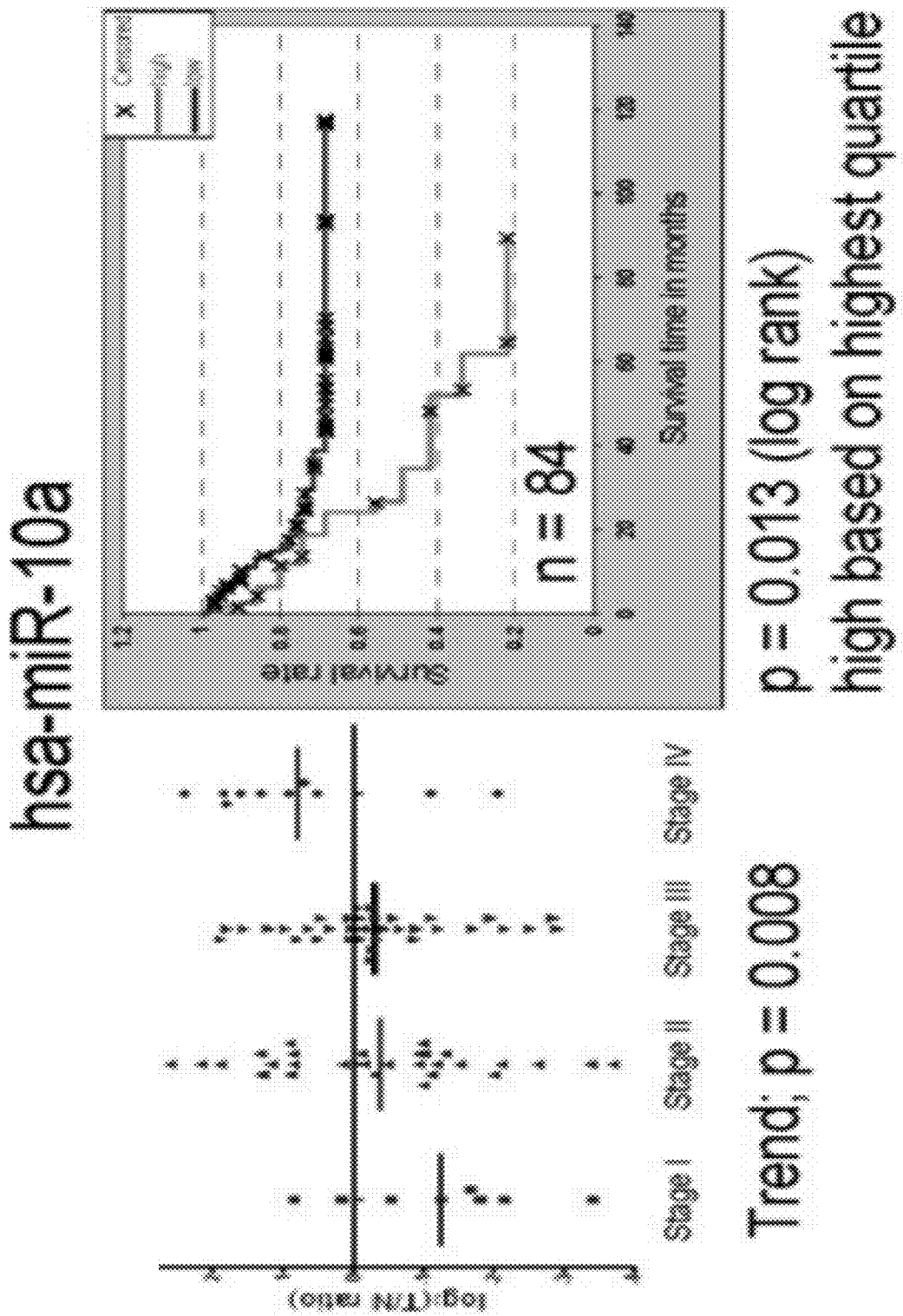
Figure 8I:
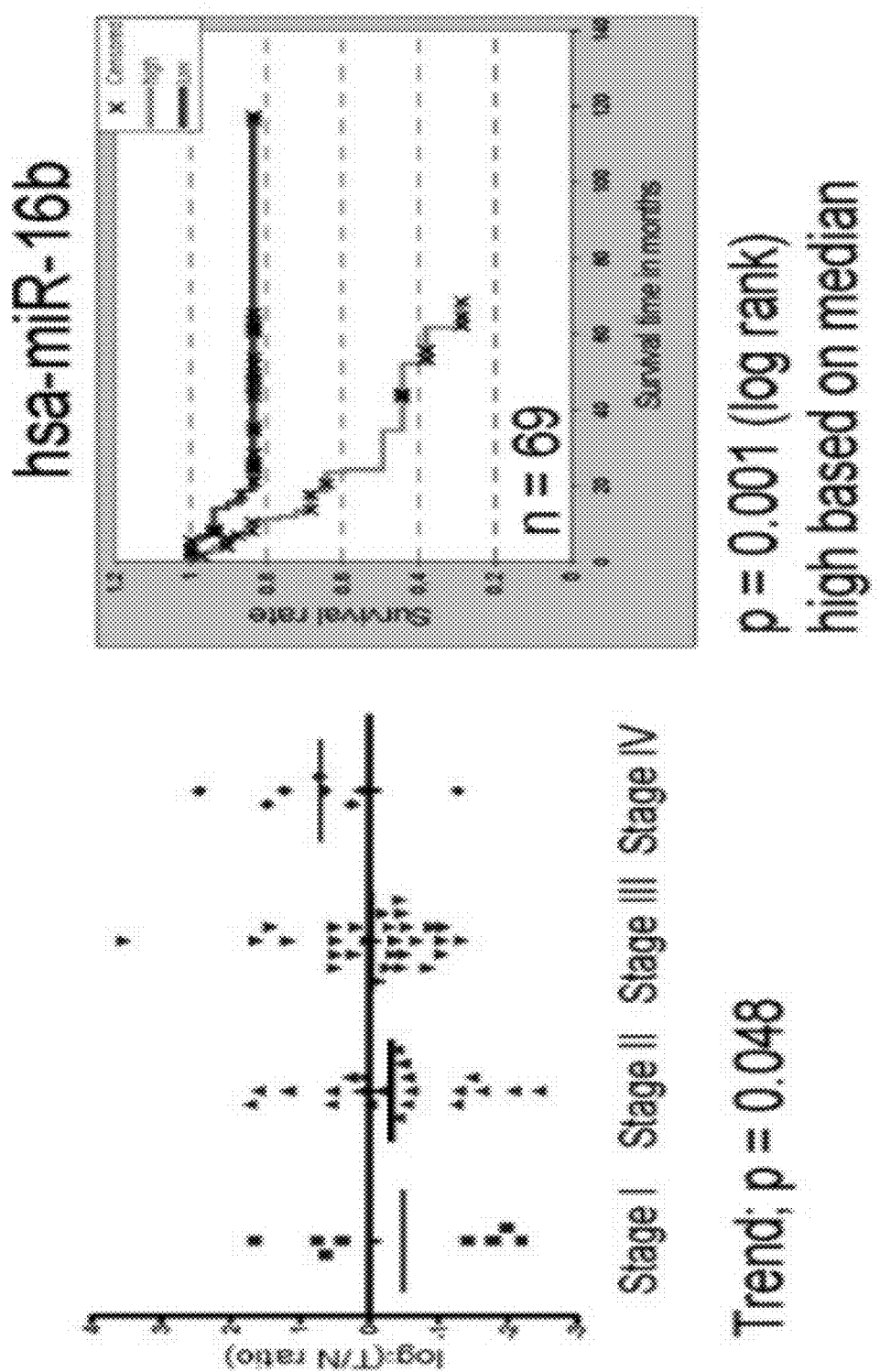

We found that miR-106a elevated in tumors (Table 7) and miR-106a TIN ratios are associated with survival prognosis (Table 9, FIG. 8b).

MiR-106a is a member of a class of paralogous miRNAs including miR-17, miR-20, miR-106a, and miR-106h. These miRNAs are very similar to one another in that they differ by only 1-2 nucleotides. Due to their similarity, they are all likely to have similar targets. Interestingly, all four of these miRNAs show similar patterns of expression and associations with prognosis (data not shown). We present herein associations for miR-106a, but we do not formally rule out the possibility that any or all of the other miRNA paralogs are contributing to this association. MiR-106a TIN ratios were dichotomized based on median values for each of the 82 individuals with data. Individuals with high miR-106a TIN expression ratios had a worse survival prognosis based on Kaplan Meier analysis (p=0.013; FIG. 8b).

This suggests that tumors expressing high levels of miR-106a are predictive of poor survival prognosis. Individuals with high TIN ratios of miR-106a were at higher risk with both univariate (FIR=2.6, p=0.01) and multivariate (HR=2.4; p=0.05) analysis adjusting for age, gender, race and TNM staging (Table 7). Therefore, miR-106a may be a useful prognostic predictor of colon cancer prognosis independent of TNM staging, Interestingly, the Retinoblastoma tumor suppressor gene has been shown to be a functional target of miR-106a, supporting a mechanism of how miR-106a may be mechanistically contributing to colon carcinogenesis.

Overexpression of the miR-17-92 cluster, which contains paralogs of miR-106a, resulted in accelerated tumor development in mice. This experimentally shows that miRNAs of the miR-106a family are capable of affecting carcinogenesis further strengthening the hypothesis that miR-106a may be contributing to carcinogenesis and tumor progression. Expression patterns of seven additional miRNAs were associated with clinical staging and poor survival prognosis (Table 9, FIGS. 8c-8i).

There is a trend that individuals diagnosed with more advanced TNM staging had higher TIN ratios for let-7g (p=0.010), miR-10a (p=0.008), miR-16h (p=0.048), miR-29a (p=0.005), miR-103-2 (p=0.033), miR-181b (p=0.016), and miR-203 (p=0.016) (FIG. 8).

TIN ratios were dichotomized based on median (miR-16h, miR-29a, miR-103-2, miR-203) or highest quartile (let-7g, miR-10a, miR-181b) and Kaplan Meier analysis revealed that high TIN ratios for each were found to be predictors of poor survival prognosis (FIG. 8c-8i).

Univariate and multivariate Cox regression analysis confirmed that high TIN ratios of any one of these miRNAs were predictive of poor colon cancer prognosis independent of TNM staging (Table 9). Multivariate Cox regression models that adjusted for age, gender, race and TNM staging showed that high TIN ratios for miR-16b (HR=5.1; p=0.003), let-7g (HR=2.5; p=0.03), miR-10a (HR=3.4; p=0.003), miR-29a (HR=3.2; p=0.01), miR-103-2 (HR=3.1; p=0.01), miR-181b (HR=3.2; p=0.01), and miR-203 (HR=3.2; p=0.03) were each predictive of poor survival prognosis. These results suggested that patients with tumors expressing high levels of any of these miRNAs are at an increased risk of dying from colon cancer. Therefore, expression levels of any these miRNAs may be useful biomarkers that can help predict survival risks for colon cancer patients independent of staging.

Figure 9A:
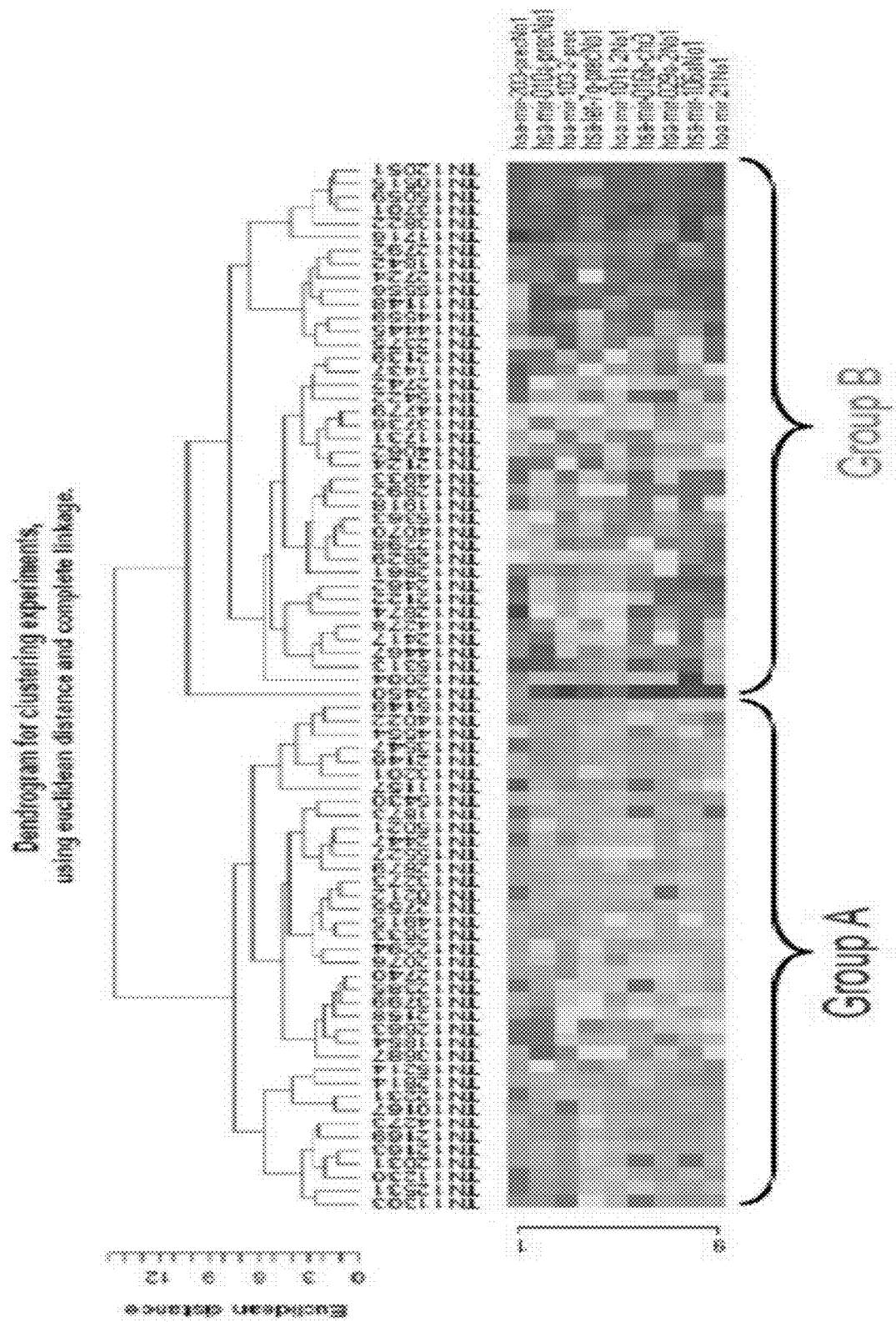
FIGS. 9a and 9b. A miRNA signature of 9 miRNAs predicts risk of dying of colon cancer. TIN ratios of miR-21, miR-106a, miR181b, miR-16b, miR-203, let-7g, miR-29a, miR-103-2 and miR-10a were each shown to be predictive of colon cancer prognosis. Hierarchical clustering of TIN ratios of these 9 miRNAs resulted in dividing individuals into two groups (1A) with significantly different survival prognoses (1B). Group B individuals were at a significantly higher risk for dying from colon cancer than group A. Individuals were excluded from this analysis if they were missing greater than 2 of the 9 TIN ratios making up the miRNA signature.

MiRNA Expression Signature of 9 miRNAS Predicts Survival Prognosis:

We used the TIN ratios for all 9 of the previously mentioned miRNAs to develop a miRNA signature that could be used to predict colon cancer prognosis. Individuals missing more than 2 of 9 of these values were excluded from this analysis. Hierarchical clustering of the TIN ratios of the 9 miRNAs resulted in grouping the remaining 78 patients into two groups (FIG. 9a).

Figure 9B:
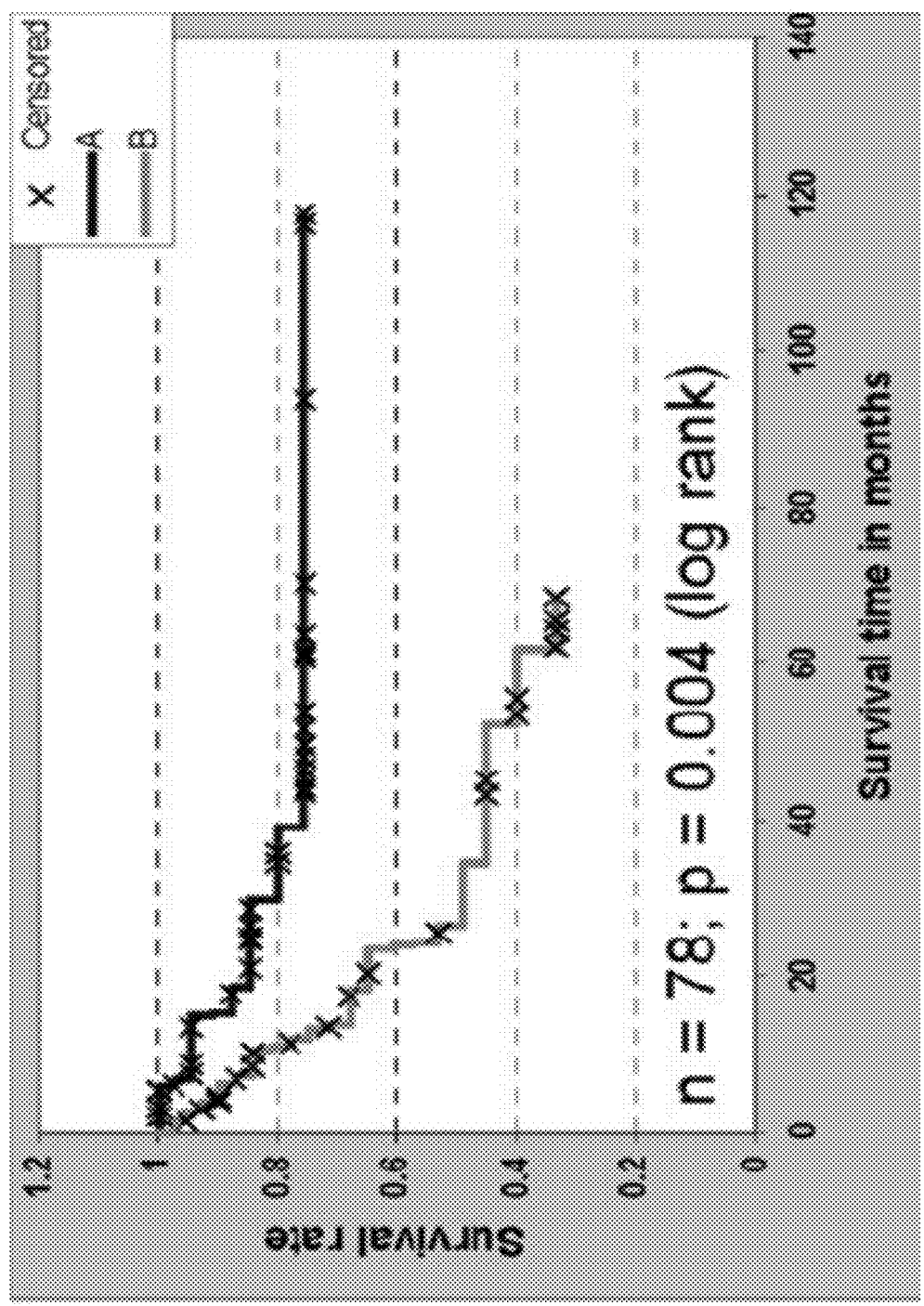

These groups had significantly different survival prognoses (FIG. 9b; p=0.004). Univariate (HR=3.2, p=0.008) and multivariate (HR=2.8; p=0.04) Cox regression analysis demonstrated that the miRNA signature was associated with poor survival prognosis independent of TNM staging (Table 10)

TABLE 10

Cox regression analysis of microRNA signature

| Variable | HR (95% CI) | p value |
|---|---|---|
| Univariate Analysis | | |
| 9 miR Cluster B/A | 3.2 (1.4-7.8) | 0.008 |
| Multivariate, adjusting for age, gender and race | | |
| 9 miR Cluster B/A | 2.8 (1.0-7.4) | 0.043 |
| age ≧ 50/age < 50 | 0.4 (0.08--1.8) | 0.23 |
| male/female | 1.9 (0.6-6.6) | 0.29 |
| AA/Caucasian | 0.9 (1.4-10.7) | 0.82 |
| Stage III-IV/Stage I-II | 3.9 (1.4-10.7) | 0.007 |

Univariate (above) and multivariate (adjusting for age, gender race and staging; below) Cox regression analyses were performed to show that individuals classified into group B using the 9 miRNA signature were at higher risk of dying of colon cancer. Neither age, gender nor race significantly contributed to survival risk. This risk associated with cluster assignment is independent of staging.

These results demonstrate that miRNA signatures may be used as a biomarker to predict the survival prognosis of colon cancer patients.

Discussion

Individual miRNAs are differentially expressed in colon tumors suggesting that altered expression of these miRNAs may be part of the cellular changes responsible for colon carcinogenesis. In addition to these findings, we show herein that miRNA expression profiles are associated with colon cancer staging and prognosis. Therefore miRNAs, either analyzed individually or as part of a miRNA signature, can be used as biomarkers that will enable physicians to predict patient survival risk with more accuracy.

The strong associations with miRNA TIN ratios with survival prognosis suggest that altered miRNA expression may be part of the causal pathway in colon carcinogenesis and progression. If altered expression of any of these mi RNAs is causal to carcinogenesis, it may be possible to design antago-mir-like pharmaceuticals that can be used to treat cancer. Using miRNA profiling and miRNA based therapeutics, it may be possible to design personalized drug treatment strategies based on which of these nine miRNAs are altered. Additionally, these strategies may be useful in preventing colon cancer in people that are at high risk due to genetically inherited risks or previous cancer history.

Example 3

Methods, Reagents and Kits for Diagnosing, Staging, Prognosing, Monitoring and Treating Colon Cancer-Related Diseases In one embodiment, there is provided a diagnostic method of assessing whether a patient has a colon cancer-related disease or has higher than normal risk for developing a colon cancer-related disease, comprising the steps of comparing the level of expression of a marker in a patient sample and the normal level of expression of the marker in a control, e.g., a sample from a patient without a colon cancer-related disease. A significantly higher level of expression of the marker in the patient sample as compared to the normal level is an indication that the patient is afflicted with a colon cancer-related disease or has higher than normal risk for developing a colon cancer-related disease.

The markers are selected such that the positive predictive value of the methods is at least about 10%, and in certain non-limiting embodiments, about 25%, about 50% or about 90%. Also preferred for use in the methods are markers that are differentially expressed, as compared to normal cells, by at least two-fold in at least about 20%, and in certain non-limiting embodiments, about 50% or about 75%.

In one diagnostic method of assessing whether a patient is afflicted with a colon cancer-related disease (e.g., new detection ("screening"), detection of recurrence, reflex testing), the method comprises comparing: a) the level of expression of a marker in a patient sample, and b) the normal level of expression of the marker in a control non-colon cancer-related disease sample. A significantly higher level of expression of the marker in the patient sample as compared to the normal level is an indication that the patient is afflicted with a colon cancer-related disease.

There is also provided diagnostic methods for assessing the efficacy of a therapy for inhibiting a colon cancer-related disease in a patient. Such methods comprise comparing: a) expression of a marker in a first sample obtained from the patient prior to providing at least a portion of the therapy to the patient, and b) expression of the marker in a second sample obtained from the patient following provision of the portion of the therapy. A significantly lower level of expression of the marker in the second sample relative to that in the first sample is an indication that the therapy is efficacious for inhibiting a colon cancer-related disease in the patient.

It will be appreciated that in these methods the "therapy" may be any therapy for treating a colon cancer-related disease including, but not limited to, pharmaceutical compositions, gene therapy and biologic therapy such as the administering of antibodies and chemokines. Thus, the methods described herein may be used to evaluate a patient before, during and after therapy, for example, to evaluate the reduction in disease state.

In certain aspects, the diagnostic methods are directed to therapy using a chemical or biologic agent. These methods comprise comparing: a) expression of a marker in a first sample obtained from the patient and maintained in the presence of the chemical or biologic agent, and b) expression of the marker in a second sample obtained from the patient and maintained in the absence of the agent. A significantly lower level of expression of the marker in the second sample relative to that in the first sample is an indication that the agent is efficacious for inhibiting a colon cancer-related disease in the patient. In one embodiment, the first and second samples can be portions of a single sample obtained from the patient or portions of pooled samples obtained from the patient.

There is also provided a monitoring method for assessing the progression of a colon cancer-related disease in a patient, the method comprising: a) detecting in a patient sample at a first time point, the expression of a marker; b) repeating step a) at a subsequent time point in time; and c) comparing the level of expression detected in steps a) and b), and therefrom monitoring the progression of a colon cancer-related disease in the patient. A significantly higher level of expression of the marker in the sample at the subsequent time point from that of the sample at the first time point is an indication that the colon cancer-related disease has progressed, whereas a significantly lower level of expression is an indication that the colon cancer-related disease has regressed.

There is further provided a diagnostic method for determining whether a colon cancer-related disease has worsened or is likely to worsen in the future, the method comprising comparing: a) the level of expression of a marker in a patient sample, and b) the normal level of expression of the marker in a control sample. A significantly higher level of expression in the patient sample as compared to the normal level is an indication that the colon cancer-related disease has worsened or is likely to worsen in the future.

There is also provided a test method for selecting a composition for inhibiting a colon cancer-related disease in a patient. This method comprises the steps of: a) obtaining a sample comprising cells from the patient; b) separately maintaining aliquots of the sample in the presence of a plurality of test compositions; c) comparing expression of a marker in each of the aliquots; and d) selecting one of the test compositions which significantly reduces the level of expression of the marker in the aliquot containing that test composition, relative to the levels of expression of the marker in the presence of the other test compositions.

There is additionally provided a test method of assessing the harmful potential of a compound in causing a colon cancer-related disease. This method comprises the steps of: a) maintaining separate aliquots of cells in the presence and absence of the compound; and b) comparing expression of a marker in each of the aliquots. A significantly higher level of expression of the marker in the aliquot maintained in the presence of the compound, relative to that of the aliquot maintained in the absence of the compound, is an indication that the compound possesses such harmful potential.

In addition, there is further provided a method of inhibiting a colon cancer-related disease in a patient. This method comprises the steps of: a) obtaining a sample comprising cells from the patient; b) separately maintaining aliquots of the sample in the presence of a plurality of compositions; c) comparing expression of a marker in each of the aliquots; and d) administering to the patient at least one of the compositions which significantly lowers the level of expression of the marker in the aliquot containing that composition, relative to the levels of expression of the marker in the presence of the other compositions.

The level of expression of a marker in a sample can be assessed, for example, by detecting the presence in the sample of: the corresponding marker protein or a fragment of the protein (e.g. by using a reagent, such as an antibody, an antibody derivative, an antibody fragment or single-chain antibody, which binds specifically with the protein or protein fragment) the corresponding marker nucleic acid (e.g. a nucleotide transcript, or a complement thereof), or a fragment of the nucleic acid (e.g. by contacting transcribed polynucleotides obtained from the sample with a substrate having affixed thereto one or more nucleic acids having the entire or a segment of the nucleic acid sequence or a complement thereof) a metabolite which is produced directly (i.e., catalyzed) or indirectly by the corresponding marker protein.

Any of the aforementioned methods may be performed using at least one or a plurality (e.g., 2, 3, 5, or 10 or more) of colon cancer-related disease markers, including colon cancer-related disease markers.

In such methods, the level of expression in the sample of each of a plurality of markers, at least one of which is a marker, is compared with the normal level of expression of each of the plurality of markers in samples of the same type obtained from control humans not afflicted with a colon cancer-related disease. A significantly altered (i.e., increased or decreased as specified in the above-described methods using a single marker) level of expression in the sample of one or more markers, or some combination thereof, relative to that marker's corresponding normal or control level, is an indication that the patient is afflicted with a colon cancer-related disease. For all of the aforementioned methods, the marker(s) are selected such that the positive predictive value of the method is at least about 10%.

In another aspect, there is provided various diagnostic and test kits. In one embodiment, a kit is useful for assessing whether a patient is afflicted with a colon cancer-related disease. The kit comprises a reagent for assessing expression of a marker. In another embodiment, a kit is useful for assessing the suitability of a chemical or biologic agent for inhibiting a colon cancer-related disease in a patient. Such a kit comprises a reagent for assessing expression of a marker, and may also comprise one or more of such agents.

In a further embodiment, the kits are useful for assessing the presence of colon cancer-related disease cells or treating colon cancer-related diseases. Such kits comprise an antibody, an antibody derivative or an antibody fragment, which binds specifically with a marker protein or a fragment of the protein. Such kits may also comprise a plurality of antibodies, antibody derivatives or antibody fragments wherein the plurality of such antibody agents binds specifically with a marker protein or a fragment of the protein.

In an additional embodiment, the kits are useful for assessing the presence of colon cancer-related disease cells, wherein the kit comprises a nucleic acid probe that binds specifically with a marker nucleic acid or a fragment of the nucleic acid. The kit may also comprise a plurality of probes, wherein each of the probes binds specifically with a marker nucleic acid, or a fragment of the nucleic acid.

In a further aspect, there is provided methods for treating a patient afflicted with a colon cancer-related disease or at risk of developing a colon cancer-related disease. Such methods may comprise reducing the expression and/or interfering with the biological function of a marker. In one embodiment, the method comprises providing to the patient an antisense oligonucleotide or polynucleotide complementary to a marker nucleic acid, or a segment thereof. For example, an antisense polynucleotide may be provided to the patient through the delivery of a vector that expresses an anti-sense polynucleotide of a marker nucleic acid or a fragment thereof. In another embodiment, the method comprises providing to the patient an antibody, an antibody derivative or antibody fragment, which binds specifically with a marker protein, or a fragment of the protein.

In a broad aspect, there is provided a method for producing a non-human animal model for assessment of at least one colon cancer-related disease. The method includes exposing the animal to repeated doses of at least one chemical believed to cause colon cancer. In certain aspects, the method further includes collecting one or more selected samples from the animal; and comparing the collected sample to one or more indicia of potential colon cancer initiation or development.

In broad aspect, there is provides a method of producing the animal model that includes: maintaining the animal in a specific chemical-free environment and sensitizing the animal with at least one chemical believed to cause colon cancer. In certain embodiments, at least a part of the animal's colon is sensitized by multiple sequential exposures.

In another broad aspect, there is provided a method of screening for an agent for effectiveness against at least one colon cancer-related disease. The method generally includes: administering at least one agent to the animal, determining whether the agent reduces or aggravates one or more symptoms of the colon cancer-related disease; correlating a reduction in one or more symptoms with effectiveness of the agent against the colon cancer-related disease; or correlating a lack of reduction in one or more symptoms with ineffectiveness of the agent.

The animal model is useful for assessing one or more metabolic pathways that contribute to at least one of initiation, progression, severity, pathology, aggressiveness, grade, activity, disability, mortality, morbidity, disease sub-classification or other underlying pathogenic or pathological feature of at least one colon cancer-related disease. The analysis can be by one or more of: hierarchical clustering, signature network construction, mass spectroscopy proteomic analysis, surface plasmon resonance, linear statistical modeling, partial least squares discriminant analysis, and multiple linear regression analysis.

In a particular aspect, the animal model is assessed for at least one colon cancer-related disease, by examining an expression level of one or more markers, or a functional equivalent thereto.

Unless otherwise defined, all technical and scientific terms used herein have the same meaning as commonly understood by one of ordinary skill in the art (e.g., in cell culture, molecular genetics, nucleic acid chemistry, hybridization techniques and biochemistry). Standard techniques are used for molecular, genetic and biochemical methods which are within the skill of the art. Such techniques are explained fully in the literature. See, for example, Molecular Cloning A Laboratory Manual, 2nd Ed., ed. by Sambrook, Fritsch and Maniatis (Cold Spring Harbor Laboratory Press: 1989); DNA Cloning, Volumes I and II (Glover ed., 1985); Oligonucleotide Synthesis (Gait ed., 1984); Mullis et al. U.S. Pat. No. 4,683,195; Nucleic Acid Hybridization (Hames & Higgins eds., 1984); Transcription And Translation (Hames & Higgins eds., 1984); Culture Of Animal Cells (R. I. Freshney, Alan R. Liss, Inc., 1987); Immobilized Cells And Enzymes (IRL Press, 1986); Perbal, A Practical Guide To Molecular Cloning (1984); the treatise, Methods In Enzymology (Academic Press, Inc., N.Y.); Gene Transfer Vectors For Mammalian Cells (Miller and Calos eds., 1987, Cold Spring Harbor Laboratory); Methods In Enzymology, Vols. 154 and 155 (Wu et al. eds.), Immunochemical Methods In Cell And Molecular Biology (Mayer and Walker, eds., Academic Press, London, 1987); Handbook Of Experimental Immunology, Volumes I-IV (Weir and Blackwell, eds., 1986); The Laboratory Rat, editor in chief: Mark A. Suckow; authors: Sharp and LaRegina. CRC Press, Boston, 1988, which are incorporated herein by reference) and chemical methods.

Described herein are newly discovered markers associated with a colon cancer-induced state of various cells. It has been discovered that the higher than normal level of expression of any of these markers or combination of these markers correlates with the presence of a colon cancer-related disease in a patient. Methods are provided for detecting the presence of a colon cancer-related disease in a sample; the absence of a in a sample; the stage of a colon cancer-related disease; and, other characteristics of a colon cancer-related disease that are relevant to the assessment, prevention, diagnosis, characterization and therapy of a colon cancer-related disease in a patient. Methods of treating a colon cancer-related disease are also provided.

DEFINITIONS

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

A "marker" is a gene or protein whose altered level of expression in a tissue or cell from its expression level in normal or healthy tissue or cell is associated with a disease state.

The "normal" level of expression of a marker is the level of expression of the marker in colon system cells of a human subject or patient not afflicted with a colon cancer-related disease.

An "over-expression" or "significantly higher level of expression" of a marker refers to an expression level in a test sample that is greater than the standard error of the assay employed to assess expression, and in certain embodiments, at least twice, and in other embodiments, three, four, five or ten times the expression level of the marker in a control sample (e.g., sample from a healthy subject not having the marker associated disease) and in certain embodiments, the average expression level of the marker in several control samples.

A "significantly lower level of expression" of a marker refers to an expression level in a test sample that is at least twice, and in certain embodiments, three, four, five or ten times lower than the expression level of the marker in a control sample (e.g., sample from a healthy subject not having the marker associated disease) and in certain embodiments, the average expression level of the marker in several control samples.

A kit is any manufacture (e.g. a package or container) comprising at least one reagent, e.g., a probe, for specifically detecting the expression of a marker. The kit may be promoted, distributed or sold as a unit for performing the methods of the present invention.

"Proteins" encompass marker proteins and their fragments; variant marker proteins and their fragments; peptides and polypeptides comprising an at least 15 amino acid segment of a marker or variant marker protein; and fusion proteins comprising a marker or variant marker protein, or an at least 15 amino acid segment of a marker or variant marker protein.

The compositions, kits and methods described herein have the following uses, among others: 1) assessing whether a patient is afflicted with a colon cancer-related disease; 2) assessing the stage of a colon cancer-related disease in a human patient; 3) assessing the grade of a colon cancer-related disease in a patient; 4) assessing the nature of a colon cancer-related disease in a patient; 5) assessing the potential to develop a colon cancer-related disease in a patient; 6) assessing the histological type of cells associated with a colon cancer-related disease in a patient; 7) making antibodies, antibody fragments or antibody derivatives that are useful for treating a colon cancer-related disease and/or assessing whether a patient is afflicted with a colon cancer-related disease; 8) assessing the presence of colon cancer-related disease cells; 9) assessing the efficacy of one or more test compounds for inhibiting a colon cancer-related disease in a patient; 10) assessing the efficacy of a therapy for inhibiting a colon cancer-related disease in a patient; 11) monitoring the progression of a colon cancer-related disease in a patient; 12) selecting a composition or therapy for inhibiting a colon cancer-related disease in a patient; 13) treating a patient afflicted with a colon cancer-related disease; 14) inhibiting a colon cancer-related disease in a patient; 15) assessing the harmful potential of a test compound; and 16) preventing the onset of a colon cancer-related disease in a patient at risk for developing a colon cancer-related disease.

Screening Methods

The animal models created by the methods described herein will enable screening of therapeutic agents useful for treating or preventing a colon cancer-related disease. Accordingly, the methods are useful for identifying therapeutic agents for treating or preventing a colon cancer-related disease. The methods comprise administering a candidate agent to an animal model made by the methods described herein, assessing at least one colon cancer-related disease response in the animal model as compared to a control animal model to which the candidate agent has not been administered. If at least one colon cancer-related disease response is reduced in symptoms or delayed in onset, the candidate agent is an agent for treating or preventing the colon cancer-related disease.

The candidate agents may be pharmacologic agents already known in the art or may be agents previously unknown to have any pharmacological activity. The agents may be naturally arising or designed in the laboratory. They may be isolated from microorganisms, animals or plants, or may be produced recombinantly, or synthesized by any suitable chemical method. They may be small molecules, nucleic acids, proteins, peptides or peptidomimetics. In certain embodiments, candidate agents are small organic compounds having a molecular weight of more than 50 and less than about 2,500 daltons. Candidate agents comprise functional groups necessary for structural interaction with proteins. Candidate agents are also found among biomolecules including, but not limited to: peptides, saccharides, fatty acids, steroids, purines, pyrimidines, derivatives, structural analogs or combinations thereof.

Candidate agents are obtained from a wide variety of sources including libraries of synthetic or natural compounds. There are, for example, numerous means available for random and directed synthesis of a wide variety of organic compounds and biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. In certain embodiments, the candidate agents can be obtained using any of the numerous approaches in combinatorial library methods art, including, by non-limiting example: biological libraries; spatially addressable parallel solid phase or solution phase libraries; synthetic library methods requiring deconvolution; the "one-bead one-compound" library method; and synthetic library methods using affinity chromatography selection.

In certain further embodiments, certain pharmacological agents may be subjected to directed or random chemical modifications, such as acylation, alkylation, esterification, amidification, etc. to produce structural analogs.

The same methods for identifying therapeutic agents for treating a colon cancer-related disease can also be used to validate lead compounds/agents generated from in vitro studies.

The candidate agent may be an agent that up- or down-regulates one or more colon cancer-related disease response pathways. In certain embodiments, the candidate agent may be an antagonist that affects such pathway.

Methods for Treating a Colon Cancer-Related Disease

There is provided herein methods for treating, inhibiting, relieving or reversing a colon cancer-related disease response. In the methods described herein, an agent that interferes with a signaling cascade is administered to an individual in need thereof, such as, but not limited to, colon cancer-related disease patients in whom such complications are not yet evident and those who already have at least one colon cancer-related disease response.

In the former instance, such treatment is useful to prevent the occurrence of such colon cancer-related disease response and/or reduce the extent to which they occur. In the latter instance, such treatment is useful to reduce the extent to which such colon cancer-related disease response occurs, prevent their further development or reverse the colon cancer-related disease response.

In certain embodiments, the agent that interferes with the colon cancer-related disease response cascade may be an antibody specific for such response.

Expression of a Marker

Expression of a marker can be inhibited in a number of ways, including, by way of a non-limiting example, an antisense oligonucleotide can be provided to the colon cancer-related disease cells in order to inhibit transcription, translation, or both, of the marker(s). Alternately, a polynucleotide encoding an antibody, an antibody derivative, or an antibody fragment which specifically binds a marker protein, and operably linked with an appropriate promoter/regulator region, can be provided to the cell in order to generate intracellular antibodies which will inhibit the function or activity of the protein. The expression and/or function of a marker may also be inhibited by treating the colon cancer-related disease cell with an antibody, antibody derivative or antibody fragment that specifically binds a marker protein. Using the methods described herein, a variety of molecules, particularly including molecules sufficiently small that they are able to cross the cell membrane, can be screened in order to identify molecules which inhibit expression of a marker or inhibit the function of a marker protein. The compound so identified can be provided to the patient in order to inhibit colon cancer-related disease cells of the patient.

Any marker or combination of markers, as well as any certain markers in combination with the markers, may be used in the compositions, kits and methods described herein. In general, it is desirable to use markers for which the difference between the level of expression of the marker in colon cancer-related disease cells and the level of expression of the same marker in normal colon system cells is as great as possible. Although this difference can be as small as the limit of detection of the method for assessing expression of the marker, it is desirable that the difference be at least greater than the standard error of the assessment method, and, in certain embodiments, a difference of at least 2-, 3-, 4-, 5-, 6-, 7-, 8-, 9-, 10-, 15-, 20-, 100-, 500-, 1000-fold or greater than the level of expression of the same marker in normal tissue.

It is recognized that certain marker proteins are secreted to the extracellular space surrounding the cells. These markers are used in certain embodiments of the compositions, kits and methods, owing to the fact that such marker proteins can be detected in a colon cancer-associated body fluid sample, which may be more easily collected from a human patient than a tissue biopsy sample. In addition, in vivo techniques for detection of a marker protein include introducing into a subject a labeled antibody directed against the protein. For example, the antibody can be labeled with a radioactive marker whose presence and location in a subject can be detected by standard imaging techniques.

In order to determine whether any particular marker protein is a secreted protein, the marker protein is expressed in, for example, a mammalian cell, such as a human colon line, extracellular fluid is collected, and the presence or absence of the protein in the extracellular fluid is assessed (e.g. using a labeled antibody which binds specifically with the protein).

It will be appreciated that patient samples containing colon cells may be used in the methods described herein. In these embodiments, the level of expression of the marker can be assessed by assessing the amount (e.g., absolute amount or concentration) of the marker in a sample. The cell sample can, of course, be subjected to a variety of post-collection preparative and storage techniques (e.g., nucleic acid and/or protein extraction, fixation, storage, freezing, ultrafiltration, concentration, evaporation, centrifugation, etc.) prior to assessing the amount of the marker in the sample.

It will also be appreciated that the markers may be shed from the cells into the digestive system, the blood stream and/or interstitial spaces. The shed markers can be tested, for example, by examining the serum or plasma.

The compositions, kits and methods can be used to detect expression of marker proteins having at least one portion which is displayed on the surface of cells which express it. For example, immunological methods may be used to detect such proteins on whole cells, or computer-based sequence analysis methods may be used to predict the presence of at least one extracellular domain (i.e., including both secreted proteins and proteins having at least one cell-surface domain). Expression of a marker protein having at least one portion which is displayed on the surface of a cell which expresses it may be detected without necessarily lysing the cell (e.g., using a labeled antibody which binds specifically with a cell-surface domain of the protein).

Expression of a marker may be assessed by any of a wide variety of methods for detecting expression of a transcribed nucleic acid or protein. Non-limiting examples of such methods include immunological methods for detection of secreted, cell-surface, cytoplasmic or nuclear proteins, protein purification methods, protein function or activity assays, nucleic acid hybridization methods, nucleic acid reverse transcription methods and nucleic acid amplification methods.

In a particular embodiment, expression of a marker is assessed using an antibody (e.g., a radio-labeled, chromophore-labeled, fluorophore-labeled or enzyme-labeled antibody), an antibody derivative (e.g., an antibody conjugated with a substrate or with the protein or ligand of a protein-ligand pair), or an antibody fragment (e.g., a single-chain antibody, an isolated antibody hypervariable domain, etc.) which binds specifically with a marker protein or fragment thereof, including a marker protein which has undergone all or a portion of its normal post-translational modification.

In another particular embodiment, expression of a marker is assessed by preparing mRNA/cDNA (i.e., a transcribed polynucleotide) from cells in a patient sample, and by hybridizing the mRNA/cDNA with a reference polynucleotide which is a complement of a marker nucleic acid, or a fragment thereof. cDNA can, optionally, be amplified using any of a variety of polymerase chain reaction methods prior to hybridization with the reference polynucleotide; preferably, it is not amplified. Expression of one or more markers can likewise be detected using quantitative PCR to assess the level of expression of the marker(s). Alternatively, any of the many methods of detecting mutations or variants (e.g., single nucleotide polymorphisms, deletions, etc.) of a marker may be used to detect occurrence of a marker in a patient.

In a related embodiment, a mixture of transcribed polynucleotides obtained from the sample is contacted with a substrate having fixed thereto a polynucleotide complementary to or homologous with at least a portion (e.g., at least 7, 10, 15, 20, 25, 30, 40, 50, 100, 500, or more nucleotide residues) of a marker nucleic acid. If polynucleotides complementary to or homologous with are differentially detectable on the substrate (e.g., detectable using different chromophores or fluorophores, or fixed to different selected positions), then the levels of expression of a plurality of markers can be assessed simultaneously using a single substrate (e.g., a "gene chip" microarray of polynucleotides fixed at selected positions). When a method of assessing marker expression is used which involves hybridization of one nucleic acid with another, it is desired that the hybridization be performed under stringent hybridization conditions.

In certain embodiments, the biomarker assays can be performed using mass spectrometry or surface plasmon resonance. In various embodiment, the method of identifying an agent active against a colon cancer-related disease can include a) providing a sample of cells containing one or more markers or derivative thereof; b) preparing an extract from said cells; c) mixing said extract with a labeled nucleic acid probe containing a marker binding site; and, d) determining the formation of a complex between the marker and the nucleic acid probe in the presence or absence of the test agent. The determining step can include subjecting said extract/nucleic acid probe mixture to an electrophoretic mobility shift assay.

In certain embodiments, the determining step comprises an assay selected from an enzyme linked immunoabsorption assay (ELISA), fluorescence based assays and ultra high throughput assays, for example surface plasmon resonance (SPR) or fluorescence correlation spectroscopy (FCS) assays. In such embodiments, the SPR sensor is useful for direct real-time observation of biomolecular interactions since SPR is sensitive to minute refractive index changes at a metal-dielectric surface. SPR is a surface technique that is sensitive to changes of $10^5$ to $10^{-6}$ refractive index (RI) units within approximately 200 nm of the SPR sensor/sample interface. Thus, SPR spectroscopy is useful for monitoring the growth of thin organic films deposited on the sensing layer.

Because the compositions, kits, and methods rely on detection of a difference in expression levels of one or more markers, it is desired that the level of expression of the marker is significantly greater than the minimum detection limit of the method used to assess expression in at least one of normal cells and colon cancer-affected cells.

It is understood that by routine screening of additional patient samples using one or more of the markers, it will be realized that certain of the markers are over-expressed in cells of various types, including specific colon cancer-related diseases.

In addition, as a greater number of patient samples are assessed for expression of the markers and the outcomes of the individual patients from whom the samples were obtained are correlated, it will also be confirmed that altered expression of certain of the markers are strongly correlated with a colon cancer-related disease and that altered expression of other markers are strongly correlated with other diseases. The compositions, kits, and methods are thus useful for characterizing one or more of the stage, grade, histological type, and nature of a colon cancer-related disease in patients.

When the compositions, kits, and methods are used for characterizing one or more of the stage, grade, histological type, and nature of a colon cancer-related disease in a patient, it is desired that the marker or panel of markers is selected such that a positive result is obtained in at least about 20%, and in certain embodiments, at least about 40%, 60%, or 80%, and in substantially all patients afflicted with a colon cancer-related disease of the corresponding stage, grade, histological type, or nature. The marker or panel of markers invention can be selected such that a positive predictive value of greater than about 10% is obtained for the general population (in a non-limiting example, coupled with an assay specificity greater than 80%).

When a plurality of markers are used in the compositions, kits, and methods, the level of expression of each marker in a patient sample can be compared with the normal level of expression of each of the plurality of markers in non-colon cancer samples of the same type, either in a single reaction mixture (i.e. using reagents, such as different fluorescent probes, for each marker) or in individual reaction mixtures corresponding to one or more of the markers. In one embodiment, a significantly increased level of expression of more than one of the plurality of markers in the sample, relative to the corresponding normal levels, is an indication that the patient is afflicted with a colon cancer-related disease. When a plurality of markers is used, 2, 3, 4, 5, 8, 10, 12, 15, 20, 30, or 50 or more individual markers can be used; in certain embodiments, the use of fewer markers may be desired.

In order to maximize the sensitivity of the compositions, kits, and methods (i.e. by interference attributable to cells of non-colon system origin in a patient sample), it is desirable that the marker used therein be a marker which has a restricted tissue distribution, e.g., normally not expressed in a non-colon system tissue.

It is recognized that the compositions, kits, and methods will be of particular utility to patients having an enhanced risk of developing a colon cancer-related disease and their medical advisors. Patients recognized as having an enhanced risk of developing a colon cancer-related disease include, for example, patients having a familial history of a colon cancer-related disease.

The level of expression of a marker in normal human colon system tissue can be assessed in a variety of ways. In one embodiment, this normal level of expression is assessed by assessing the level of expression of the marker in a portion of colon system cells which appear to be normal and by comparing this normal level of expression with the level of expression in a portion of the colon system cells which is suspected of being abnormal. Alternately, and particularly as further information becomes available as a result of routine performance of the methods described herein, population-average values for normal expression of the markers may be used. In other embodiments, the 'normal' level of expression of a marker may be determined by assessing expression of the marker in a patient sample obtained from a non-colon cancer-afflicted patient, from a patient sample obtained from a patient before the suspected onset of a colon cancer-related disease in the patient, from archived patient samples, and the like.

There is also provided herein compositions, kits, and methods for assessing the presence of colon cancer-related disease cells in a sample (e.g. an archived tissue sample or a sample obtained from a patient). These compositions, kits, and methods are substantially the same as those described above, except that, where necessary, the compositions, kits, and methods are adapted for use with samples other than patient samples. For example, when the sample to be used is a parafinized, archived human tissue sample, it can be necessary to adjust the ratio of compounds in the compositions, in the kits, or the methods used to assess levels of marker expression in the sample.

Kits and Reagents

The kits are useful for assessing the presence of colon cancer-related disease cells (e.g. in a sample such as a patient sample). The kit comprises a plurality of reagents, each of which is capable of binding specifically with a marker nucleic acid or protein. Suitable reagents for binding with a marker protein include antibodies, antibody derivatives, antibody fragments, and the like. Suitable reagents for binding with a marker nucleic acid (e.g. a genomic DNA, an mRNA, a spliced mRNA, a cDNA, or the like) include complementary nucleic acids. For example, the nucleic acid reagents may include oligonucleotides (labeled or non-labeled) fixed to a substrate, labeled oligonucleotides not bound with a substrate, pairs of PCR primers, molecular beacon probes, and the like.

The kits may optionally comprise additional components useful for performing the methods described herein. By way of example, the kit may comprise fluids (e.g. SSC buffer) suitable for annealing complementary nucleic acids or for binding an antibody with a protein with which it specifically binds, one or more sample compartments, an instructional material which describes performance of the method, a sample of normal colon system cells, a sample of colon cancer-related disease cells, and the like.

Method of Producing Antibodies

There is also provided herein a method of making an isolated hybridoma which produces an antibody useful for assessing whether a patient is afflicted with a colon cancer-related disease. In this method, a protein or peptide comprising the entirety or a segment of a marker protein is synthesized or isolated (e.g. by purification from a cell in which it is expressed or by transcription and translation of a nucleic acid encoding the protein or peptide in vivo or in vitro). A vertebrate, for example, a mammal such as a mouse, rat, rabbit, or sheep, is immunized using the protein or peptide. The vertebrate may optionally (and preferably) be immunized at least one additional time with the protein or peptide, so that the vertebrate exhibits a robust immune response to the protein or peptide. Splenocytes are isolated from the immunized vertebrate and fused with an immortalized cell line to form hybridomas, using any of a variety of methods. Hybridomas formed in this manner are then screened using standard methods to identify one or more hybridomas which produce an antibody which specifically binds with the marker protein or a fragment thereof. There is also provided herein hybridomas made by this method and antibodies made using such hybridomas.

Method of Assessing Efficacy

There is also provided herein a method of assessing the efficacy of a test compound for inhibiting colon cancer-related disease cells. As described above, differences in the level of expression of the markers correlate with the abnormal state of colon system cells. Although it is recognized that changes in the levels of expression of certain of the markers likely result from the abnormal state of colon system cells, it is likewise recognized that changes in the levels of expression of other of the markers induce, maintain, and promote the abnormal state of those cells. Thus, compounds which inhibit a colon cancer-related disease in a patient will cause the level of expression of one or more of the markers to change to a level nearer the normal level of expression for that marker (i.e. the level of expression for the marker in normal colon system cells).

This method thus comprises comparing expression of a marker in a first colon cell sample and maintained in the presence of the test compound and expression of the marker in a second colon cell sample and maintained in the absence of the test compound. A significantly reduced expression of a marker in the presence of the test compound is an indication that the test compound inhibits a colon cancer-related disease. The colon cell samples may, for example, be aliquots of a single sample of normal colon cells obtained from a patient, pooled samples of normal colon cells obtained from a patient, cells of a normal colon cell line, aliquots of a single sample of colon cancer-related disease cells obtained from a patient, pooled samples of colon cancer-related disease cells obtained from a patient, cells of a colon cancer-related disease cell line, or the like.

In one embodiment, the samples are colon cancer-related disease cells obtained from a patient and a plurality of compounds believed to be effective for inhibiting various colon cancer-related diseases are tested in order to identify the compound which is likely to best inhibit the colon cancer-related disease in the patient.

This method may likewise be used to assess the efficacy of a therapy for inhibiting a colon cancer-related disease in a patient. In this method, the level of expression of one or more markers in a pair of samples (one subjected to the therapy, the other not subjected to the therapy) is assessed. As with the method of assessing the efficacy of test compounds, if the therapy induces a significantly lower level of expression of a marker then the therapy is efficacious for inhibiting a colon cancer-related disease. As above, if samples from a selected patient are used in this method, then alternative therapies can be assessed in vitro in order to select a therapy most likely to be efficacious for inhibiting a colon cancer-related disease in the patient.

As described herein, the abnormal state of human colon cells is correlated with changes in the levels of expression of the markers. There is also provided a method for assessing the harmful potential of a test compound. This method comprises maintaining separate aliquots of human colon cells in the presence and absence of the test compound. Expression of a marker in each of the aliquots is compared. A significantly higher level of expression of a marker in the aliquot maintained in the presence of the test compound (relative to the aliquot maintained in the absence of the test compound) is an indication that the test compound possesses a harmful potential. The relative harmful potential of various test compounds can be assessed by comparing the degree of enhancement or inhibition of the level of expression of the relevant markers, by comparing the number of markers for which the level of expression is enhanced or inhibited, or by comparing both.

Various aspects are described in further detail in the following subsections.

Isolated Proteins and Antibodies

One aspect pertains to isolated marker proteins and biologically active portions thereof, as well as polypeptide fragments suitable for use as immunogens to raise antibodies directed against a marker protein or a fragment thereof. In one embodiment, the native marker protein can be isolated from cells or tissue sources by an appropriate purification scheme using standard protein purification techniques. In another embodiment, a protein or peptide comprising the whole or a segment of the marker protein is produced by recombinant DNA techniques. Alternative to recombinant expression, such protein or peptide can be synthesized chemically using standard peptide synthesis techniques.

An "isolated" or "purified" protein or biologically active portion thereof is substantially free of cellular material or other contaminating proteins from the cell or tissue source from which the protein is derived, or substantially free of chemical precursors or other chemicals when chemically synthesized. The language "substantially free of cellular material" includes preparations of protein in which the protein is separated from cellular components of the cells from which it is isolated or recombinantly produced. Thus, protein that is substantially free of cellular material includes preparations of protein having less than about 30%, 20%, 10%, or 5% (by dry weight) of heterologous protein (also referred to herein as a "contaminating protein").

When the protein or biologically active portion thereof is recombinantly produced, it is also preferably substantially free of culture medium, i.e., culture medium represents less than about 20%, 10%, or 5% of the volume of the protein preparation. When the protein is produced by chemical synthesis, it is preferably substantially free of chemical precursors or other chemicals, i.e., it is separated from chemical precursors or other chemicals which are involved in the synthesis of the protein. Accordingly such preparations of the protein have less than about 30%, 20%, 10%, 5% (by dry weight) of chemical precursors or compounds other than the polypeptide of interest.

Biologically active portions of a marker protein include polypeptides comprising amino acid sequences sufficiently identical to or derived from the amino acid sequence of the marker protein, which include fewer amino acids than the full length protein, and exhibit at least one activity of the corresponding full-length protein. Typically, biologically active portions comprise a domain or motif with at least one activity of the corresponding full-length protein. A biologically active portion of a marker protein can be a polypeptide which is, for example, 10, 25, 50, 100 or more amino acids in length. Moreover, other biologically active portions, in which other regions of the marker protein are deleted, can be prepared by recombinant techniques and evaluated for one or more of the functional activities of the native form of the marker protein. In certain embodiments, useful proteins are substantially identical (e.g., at least about 40%, and in certain embodiments, 50%, 60%, 70%, 80%, 90%, 95%, or 99%) to one of these sequences and retain the functional activity of the corresponding naturally-occurring marker protein yet differ in amino acid sequence due to natural allelic variation or mutagenesis.

In addition, libraries of segments of a marker protein can be used to generate a variegated population of polypeptides for screening and subsequent selection of variant marker proteins or segments thereof.

Predictive Medicine

There is also provided herein uses of the animal models and markers in the field of predictive medicine in which diagnostic assays, prognostic assays, pharmacogenomics, and monitoring clinical trials are used for prognostic (predictive) purposes to thereby treat an individual prophylactically. Accordingly, there is also provided herein diagnostic assays for determining the level of expression of one or more marker proteins or nucleic acids, in order to determine whether an individual is at risk of developing a colon cancer-related disease. Such assays can be used for prognostic or predictive purposes to thereby prophylactically treat an individual prior to the onset of the colon cancer-related disease.

In another aspect, the methods are useful for at least periodic screening of the same individual to see if that individual has been exposed to chemicals or toxins that change his/her expression patterns.

Yet another aspect pertains to monitoring the influence of agents (e.g., drugs or other compounds administered either to inhibit a colon cancer-related disease or to treat or prevent any other disorder (e.g., in order to understand any system effects that such treatment may have) on the expression or activity of a marker in clinical trials.

Pharmacogenomics

The markers are also useful as pharmacogenomic markers. As used herein, a "pharmacogenomic marker" is an objective biochemical marker whose expression level correlates with a specific clinical drug response or susceptibility in a patient. The presence or quantity of the pharmacogenomic marker expression is related to the predicted response of the patient and more particularly the patient's tumor to therapy with a specific drug or class of drugs. By assessing the presence or quantity of the expression of one or more pharmacogenomic markers in a patient, a drug therapy which is most appropriate for the patient, or which is predicted to have a greater degree of success, may be selected.

Monitoring Clinical Trials

Monitoring the influence of agents (e.g., drug compounds) on the level of expression of a marker can be applied not only in basic drug screening, but also in clinical trials. For example, the effectiveness of an agent to affect marker expression can be monitored in clinical trials of subjects receiving treatment for a colon cancer-related disease.

In one non-limiting embodiment, the present invention provides a method for monitoring the effectiveness of treatment of a subject with an agent (e.g., an agonist, antagonist, peptidomimetic, protein, peptide, nucleic acid, small molecule, or other drug candidate) comprising the steps of (i) obtaining a pre-administration sample from a subject prior to administration of the agent; (ii) detecting the level of expression of one or more selected markers in the pre-administration sample; (iii) obtaining one or more post-administration samples from the subject; (iv) detecting the level of expression of the marker(s) in the post-administration samples; (v) comparing the level of expression of the marker(s) in the pre-administration sample with the level of expression of the marker(s) in the post-administration sample or samples; and (vi) altering the administration of the agent to the subject accordingly.

For example, increased expression of the marker gene(s) during the course of treatment may indicate ineffective dosage and the desirability of increasing the dosage. Conversely, decreased expression of the marker gene(s) may indicate efficacious treatment and no need to change dosage.

Electronic Apparatus Readable Media, Systems, Arrays and Methods of Using Same

As used herein, "electronic apparatus readable media" refers to any suitable medium for storing, holding or containing data or information that can be read and accessed directly by an electronic apparatus. Such media can include, but are not limited to: magnetic storage media, such as floppy discs, hard disc storage medium, and magnetic tape; optical storage media such as compact disc; electronic storage media such as RAM, ROM, EPROM, EEPROM and the like; and general hard disks and hybrids of these categories such as magnetic/optical storage media. The medium is adapted or configured for having recorded thereon a marker as described herein.

As used herein, the term "electronic apparatus" is intended to include any suitable computing or processing apparatus or other device configured or adapted for storing data or information. Examples of electronic apparatus suitable for use with the present invention include stand-alone computing apparatus; networks, including a local area network (LAN), a wide area network (WAN) Internet, Intranet, and Extranet; electronic appliances such as personal digital assistants (PDAs), cellular phone, pager and the like; and local and distributed processing systems.

As used herein, "recorded" refers to a process for storing or encoding information on the electronic apparatus readable medium. Those skilled in the art can readily adopt any method for recording information on media to generate materials comprising the markers described herein.

A variety of software programs and formats can be used to store the marker information of the present invention on the electronic apparatus readable medium. Any number of data processor structuring formats (e.g., text file or database) may be employed in order to obtain or create a medium having recorded thereon the markers. By providing the markers in readable form, one can routinely access the marker sequence information for a variety of purposes. For example, one skilled in the art can use the nucleotide or amino acid sequences in readable form to compare a target sequence or target structural motif with the sequence information stored within the data storage means. Search means are used to identify fragments or regions of the sequences which match a particular target sequence or target motif.

Thus, there is also provided herein a medium for holding instructions for performing a method for determining whether a subject has a colon cancer-related disease or a pre-disposition to a colon cancer-related disease, wherein the method comprises the steps of determining the presence or absence of a marker and based on the presence or absence of the marker, determining whether the subject has a colon cancer-related disease or a pre-disposition to a colon cancer-related disease and/or recommending a particular treatment for a colon cancer-related disease or pre-colon cancer-related disease condition.

There is also provided herein an electronic system and/or in a network, a method for determining whether a subject has a colon cancer-related disease or a pre-disposition to a colon cancer-related disease associated with a marker wherein the method comprises the steps of determining the presence or absence of the marker, and based on the presence or absence of the marker, determining whether the subject has a colon cancer-related disease or a pre-disposition to a colon cancer-related disease, and/or recommending a particular treatment for the colon cancer-related disease or pre-colon cancer-related disease condition. The method may further comprise the step of receiving phenotypic information associated with the subject and/or acquiring from a network phenotypic information associated with the subject.

Also provided herein is a network, a method for determining whether a subject has a colon cancer-related disease or a pre-disposition to a colon cancer-related disease associated with a marker, the method comprising the steps of receiving information associated with the marker, receiving phenotypic information associated with the subject, acquiring information from the network corresponding to the marker and/or a colon cancer-related disease, and based on one or more of the phenotypic information, the marker, and the acquired information, determining whether the subject has a colon cancer-related disease or a pre-disposition to a colon cancer-related disease. The method may further comprise the step of recommending a particular treatment for the colon cancer-related disease or pre-colon cancer-related disease condition.

There is also provided herein a business method for determining whether a subject has a colon cancer-related disease or a pre-disposition to a colon cancer-related disease, the method comprising the steps of receiving information associated with the marker, receiving phenotypic information associated with the subject, acquiring information from the network corresponding to the marker and/or a colon cancer-related disease, and based on one or more of the phenotypic information, the marker, and the acquired information, determining whether the subject has a colon cancer-related disease or a pre-disposition to a colon cancer-related disease. The method may further comprise the step of recommending a particular treatment for the colon cancer-related disease or pre-colon cancer-related disease condition.

There is also provided herein an array that can be used to assay expression of one or more genes in the array. In one embodiment, the array can be used to assay gene expression in a tissue to ascertain tissue specificity of genes in the array. In this manner, up to about 7000 or more genes can be simultaneously assayed for expression. This allows a profile to be developed showing a battery of genes specifically expressed in one or more tissues.

In addition to such qualitative determination, there is provided herein the quantitation of gene expression. Thus, not only tissue specificity, but also the level of expression of a battery of genes in the tissue is ascertainable. Thus, genes can be grouped on the basis of their tissue expression per se and level of expression in that tissue. This is useful, for example, in ascertaining the relationship of gene expression between or among tissues. Thus, one tissue can be perturbed and the effect on gene expression in a second tissue can be determined. In this context, the effect of one cell type on another cell type in response to a biological stimulus can be determined.

Such a determination is useful, for example, to know the effect of cell-cell interaction at the level of gene expression. If an agent is administered therapeutically to treat one cell type but has an undesirable effect on another cell type, the method provides an assay to determine the molecular basis of the undesirable effect and thus provides the opportunity to co-administer a counteracting agent or otherwise treat the undesired effect. Similarly, even within a single cell type, undesirable biological effects can be determined at the molecular level. Thus, the effects of an agent on expression of other than the target gene can be ascertained and counteracted.

In another embodiment, the array can be used to monitor the time course of expression of one or more genes in the array. This can occur in various biological contexts, as disclosed herein, for example development of a colon cancer-related disease, progression of a colon cancer-related disease, and processes, such as cellular transformation associated with a colon cancer-related disease.

The array is also useful for ascertaining the effect of the expression of a gene or the expression of other genes in the same cell or in different cells. This provides, for example, for a selection of alternate molecular targets for therapeutic intervention if the ultimate or downstream target cannot be regulated.

The array is also useful for ascertaining differential expression patterns of one or more genes in normal and abnormal cells. This provides a battery of genes that could serve as a molecular target for diagnosis or therapeutic intervention.

Surrogate Markers

The markers may serve as surrogate markers for one or more disorders or disease states or for conditions leading up to a colon cancer-related disease state. As used herein, a "surrogate marker" is an objective biochemical marker which correlates with the absence or presence of a disease or disorder, or with the progression of a disease or disorder. The presence or quantity of such markers is independent of the disease. Therefore, these markers may serve to indicate whether a particular course of treatment is effective in lessening a disease state or disorder. Surrogate markers are of particular use when the presence or extent of a disease state or disorder is difficult to assess through standard methodologies, or when an assessment of disease progression is desired before a potentially dangerous clinical endpoint is reached.

The markers are also useful as pharmacodynamic markers. As used herein, a "pharmacodynamic marker" is an objective biochemical marker which correlates specifically with drug effects. The presence or quantity of a pharmacodynamic marker is not related to the disease state or disorder for which the drug is being administered; therefore, the presence or quantity of the marker is indicative of the presence or activity of the drug in a subject. For example, a pharmacodynamic marker may be indicative of the concentration of the drug in a biological tissue, in that the marker is either expressed or transcribed or not expressed or transcribed in that tissue in relationship to the level of the drug. In this fashion, the distribution or uptake of the drug may be monitored by the pharmacodynamic marker. Similarly, the presence or quantity of the pharmacodynamic marker may be related to the presence or quantity of the metabolic product of a drug, such that the presence or quantity of the marker is indicative of the relative breakdown rate of the drug in vivo.

Pharmacodynamic markers are of particular use in increasing the sensitivity of detection of drug effects, particularly when the drug is administered in low doses. Since even a small amount of a drug may be sufficient to activate multiple rounds of marker transcription or expression, the amplified marker may be in a quantity which is more readily detectable than the drug itself. Also, the marker may be more easily detected due to the nature of the marker itself; for example, using the methods described herein, antibodies may be employed in an immune-based detection system for a protein marker, or marker-specific radiolabeled probes may be used to detect a mRNA marker. Furthermore, the use of a pharmacodynamic marker may offer mechanism-based prediction of risk due to drug treatment beyond the range of possible direct observations.

Protocols for Testing

The method of testing for colon cancer-related diseases comprises, for example measuring the expression level of each marker gene in a biological sample from a subject over time and comparing the level with that of the marker gene in a control biological sample.

When the marker gene is one of the genes described herein and the expression level is differentially expressed (for examples, higher or lower than that in the control), the subject is judged to be affected with a colon cancer-related disease. When the expression level of the marker gene falls within the permissible range, the subject is unlikely to be affected with a colon cancer-related disease.

The standard value for the control may be pre-determined by measuring the expression level of the marker gene in the control, in order to compare the expression levels. For example, the standard value can be determined based on the expression level of the above-mentioned marker gene in the control. For example, in certain embodiments, the permissible range is taken as ±2S.D. based on the standard value. Once the standard value is determined, the testing method may be performed by measuring only the expression level in a biological sample from a subject and comparing the value with the determined standard value for the control.

Expression levels of marker genes include transcription of the marker genes to mRNA, and translation into proteins. Therefore, one method of testing for a colon cancer-related disease is performed based on a comparison of the intensity of expression of mRNA corresponding to the marker genes, or the expression level of proteins encoded by the marker genes.

The measurement of the expression levels of marker genes in the testing for a colon cancer-related disease can be carried out according to various gene analysis methods. Specifically, one can use, for example, a hybridization technique using nucleic acids that hybridize to these genes as probes, or a gene amplification technique using DNA that hybridize to the marker genes as primers.

The probes or primers used for the testing can be designed based on the nucleotide sequences of the marker genes. The identification numbers for the nucleotide sequences of the respective marker genes are describer herein.

Further, it is to be understood that genes of higher animals generally accompany polymorphism in a high frequency.

There are also many molecules that produce isoforms comprising mutually different amino acid sequences during the splicing process. Any gene associated with a colon cancer-related disease that has an activity similar to that of a marker gene is included in the marker genes, even if it has nucleotide sequence differences due to polymorphism or being an isoform.

It is also to be understood that the marker genes can include homologs of other species in addition to humans. Thus, unless otherwise specified, the expression "marker gene" refers to a homolog of the marker gene unique to the species or a foreign marker gene which has been introduced into an individual.

Also, it is to be understood that a "homolog of a marker gene" refers to a gene derived from a species other than a human, which can hybridize to the human marker gene as a probe under stringent conditions. Such stringent conditions are known to one skilled in the art who can select an appropriate condition to produce an equal stringency experimentally or empirically.

A polynucleotide comprising the nucleotide sequence of a marker gene or a nucleotide sequence that is complementary to the complementary strand of the nucleotide sequence of a marker gene and has at least 15 nucleotides, can be used as a primer or probe. Thus, a "complementary strand" means one strand of a double stranded DNA with respect to the other strand and which is composed of A:T (U for RNA) and G:C base pairs.

In addition, "complementary" means not only those that are completely complementary to a region of at least 15 continuous nucleotides, but also those that have a nucleotide sequence homology of at least 40% in certain instances, 50% in certain instances, 60% in certain instances, 70% in certain instances, at least 80%, 90%, and 95% or higher. The degree of homology between nucleotide sequences can be determined by an algorithm, BLAST, etc.

Such polynucleotides are useful as a probe to detect a marker gene, or as a primer to amplify a marker gene. When used as a primer, the polynucleotide comprises usually 15 bp to 100 bp, and in certain embodiments 15 bp to 35 bp of nucleotides. When used as a probe, a DNA comprises the whole nucleotide sequence of the marker gene (or the complementary strand thereof), or a partial sequence thereof that has at least 15 bp nucleotides. When used as a primer, the 3' region must be complementary to the marker gene, while the 5' region can be linked to a restriction enzyme-recognition sequence or a tag.

"Polynucleotides" may be either DNA or RNA. These polynucleotides may be either synthetic or naturally-occurring. Also, DNA used as a probe for hybridization is usually labeled. Those skilled in the art readily understand such labeling methods. Herein, the term "oligonucleotide" means a polynucleotide with a relatively low degree of polymerization. Oligonucleotides are included in polynucleotides.

Tests for a colon cancer-related disease using hybridization techniques can be performed using, for example, Northern hybridization, dot blot hybridization, or the DNA microarray technique. Furthermore, gene amplification techniques, such as the RT-PCR method may be used. By using the PCR amplification monitoring method during the gene amplification step in RT-PCR, one can achieve a more quantitative analysis of the expression of a marker gene.

In the PCR gene amplification monitoring method, the detection target (DNA or reverse transcript of RNA) is hybridized to probes that are labeled with a fluorescent dye and a quencher which absorbs the fluorescence. When the PCR proceeds and Taq polymerase degrades the probe with its 5'-3' exonuclease activity, the fluorescent dye and the quencher draw away from each other and the fluorescence is detected. The fluorescence is detected in real time. By simultaneously measuring a standard sample in which the copy number of a target is known, it is possible to determine the copy number of the target in the subject sample with the cycle number where PCR amplification is linear. Also, one skilled in the art recognizes that the PCR amplification monitoring method can be carried out using any suitable method.

The method of testing for a colon cancer-related disease can be also carried out by detecting a protein encoded by a marker gene. Hereinafter, a protein encoded by a marker gene is described as a "marker protein." For such test methods, for example, the Western blotting method, the immunoprecipitation method, and the ELISA method may be employed using an antibody that binds to each marker protein.

Antibodies used in the detection that bind to the marker protein may be produced by any suitable technique. Also, in order to detect a marker protein, such an antibody may be appropriately labeled. Alternatively, instead of labeling the antibody, a substance that specifically binds to the antibody, for example, protein A or protein G, may be labeled to detect the marker protein indirectly. More specifically, such a detection method can include the ELISA method.

A protein or a partial peptide thereof used as an antigen may be obtained, for example, by inserting a marker gene or a portion thereof into an expression vector, introducing the construct into an appropriate host cell to produce a transformant, culturing the transformant to express the recombinant protein, and purifying the expressed recombinant protein from the culture or the culture supernatant. Alternatively, the amino acid sequence encoded by a gene or an oligopeptide comprising a portion of the amino acid sequence encoded by a full-length cDNA are chemically synthesized to be used as an immunogen.

Furthermore, a test for a colon cancer-related disease can be performed using as an index not only the expression level of a marker gene but also the activity of a marker protein in a biological sample. Activity of a marker protein means the biological activity intrinsic to the protein. Various methods can be used for measuring the activity of each protein.

Even if a patient is not diagnosed as being affected with a colon cancer-related disease in a routine test in spite of symptoms suggesting these diseases, whether or not such a patient is suffering from a colon cancer-related disease can be easily determined by performing a test according to the methods described herein.

More specifically, in certain embodiments, when the marker gene is one of the genes described herein, an increase or decrease in the expression level of the marker gene in a patient whose symptoms suggest at least a susceptibility to a colon cancer-related disease indicates that the symptoms are primarily caused by a colon cancer-related disease.

In addition, the tests are useful to determine whether a colon cancer-related disease is improving in a patient. In other words, the methods described herein can be used to judge the therapeutic effect of a treatment for a colon cancer-related disease. Furthermore, when the marker gene is one of the genes described herein, an increase or decrease in the expression level of the marker gene in a patient, who has been diagnosed as being affected by a colon cancer-related disease, implies that the disease has progressed more.

The severity and/or susceptibility to a colon cancer-related disease may also be determined based on the difference in expression levels. For example, when the marker gene is one of the genes described herein, the degree of increase in the expression level of the marker gene is correlated with the presence and/or severity of a colon cancer-related disease.

Animal Models

In another aspect, there is provided herein animal models for a colon cancer-related disease where the expression level of one or more marker genes or a gene functionally equivalent to the marker gene has been elevated in the animal model. A "functionally equivalent gene" as used herein generally is a gene that encodes a protein having an activity similar to a known activity of a protein encoded by the marker gene. A representative example of a functionally equivalent gene includes a counterpart of a marker gene of a subject animal, which is intrinsic to the animal.

The animal model for a colon cancer-related disease is useful for detecting physiological changes due to a colon cancer-related disease. In certain embodiments, the animal model is useful to reveal additional functions of marker genes and to evaluate drugs whose targets are the marker genes.

In one embodiment, an animal model for a colon cancer-related disease can be created by controlling the expression level of a counterpart gene or administering a counterpart gene. The method can include creating an animal model for a colon cancer-related disease by controlling the expression level of a gene selected from the group of genes described herein. In another embodiment, the method can include creating an animal model for a colon cancer-related disease by administering the protein encoded by a gene described herein, or administering an antibody against the protein. It is to be also understood, that in certain other embodiments, the marker can be over-expressed such that the marker can then be measured using appropriate methods.

In another embodiment, an animal model for a colon cancer-related disease can be created by introducing a gene selected from such groups of genes, or by administering a protein encoded by such a gene.

In another embodiment, a colon cancer-related disease can be induced by suppressing the expression of a gene selected from such groups of genes or the activity of a protein encoded by such a gene. An antisense nucleic acid, a ribozyme, or an RNAi can be used to suppress the expression. The activity of a protein can be controlled effectively by administering a substance that inhibits the activity, such as an antibody.

The animal model is useful to elucidate the mechanism underlying a colon cancer-related disease and also to test the safety of compounds obtained by screening. For example, when an animal model develops the symptoms of colon cancer-related disease, or when a measured value involved in a certain a colon cancer-related disease alters in the animal, a screening system can be constructed to explore compounds having activity to alleviate the disease.

As used herein, the expression "an increase in the expression level" refers to any one of the following: where a marker gene introduced as a foreign gene is expressed artificially; where the transcription of a marker gene intrinsic to the subject animal and the translation thereof into the protein are enhanced; or where the hydrolysis of the protein, which is the translation product, is suppressed. As used herein, the expression "a decrease in the expression level" refers to either the state in which the transcription of a marker gene of the subject animal and the translation thereof into the protein are inhibited, or the state in which the hydrolysis of the protein, which is the translation product, is enhanced. The expression level of a gene can be determined, for example, by a difference in signal intensity on a DNA chip. Furthermore, the activity of the translation product—the protein—can be determined by comparing with that in the normal state.

It is also within the contemplated scope that the animal model can include transgenic animals, including, for example animals where a marker gene has been introduced and expressed artificially; marker gene knockout animals; and knock-in animals in which another gene has been substituted for a marker gene. A transgenic animal, into which an antisense nucleic acid of a marker gene, a ribozyme, a polynucleotide having an RNAi effect, or a DNA functioning as a decoy nucleic acid or such has been introduced, can be used as the transgenic animal. Such transgenic animals also include, for example, animals in which the activity of a marker protein has been enhanced or suppressed by introducing a mutation(s) into the coding region of the gene, or the amino acid sequence has been modified to become resistant or susceptible to hydrolysis. Mutations in an amino acid sequence include substitutions, deletions, insertions, and additions.

In addition, the expression itself of a marker gene can be controlled by introducing a mutation(s) into the transcriptional regulatory region of the gene. Those skilled in the art understand such amino acid substitutions. Also, the number of amino acids that are mutated is not particularly restricted, as long as the activity is maintained Normally, it is within 50 amino acids, in certain non-limiting embodiments, within 30 amino acids, within 10 amino acids, or within 3 amino acids. The site of mutation may be any site, as long as the activity is maintained.

In yet another aspect, there is provided herein screening methods for candidate compounds for therapeutic agents to treat a colon cancer-related disease. One or more marker genes are selected from the group of genes described herein. A therapeutic agent for a colon cancer-related disease can be obtained by selecting a compound capable of increasing or decreasing the expression level of the marker gene(s).

It is to be understood that the expression "a compound that increases the expression level of a gene" refers to a compound that promotes any one of the steps of gene transcription, gene translation, or expression of a protein activity. On the other hand, the expression "a compound that decreases the expression level of a gene", as used herein, refers to a compound that inhibits any one of these steps.

In particular aspects, the method of screening for a therapeutic agent for a colon cancer-related disease can be carried out either in vivo or in vitro. This screening method can be performed, for example, by (1) administering a candidate compound to an animal subject; (2) measuring the expression level of a marker gene(s) in a biological sample from the animal subject; or (3) selecting a compound that increases or decreases the expression level of a marker gene(s) as compared to that in a control with which the candidate compound has not been contacted.

In still another aspect, there is provided herein a method to assess the efficacy of a candidate compound for a pharmaceutical agent on the expression level of a marker gene(s) by contacting an animal subject with the candidate compound and monitoring the effect of the compound on the expression level of the marker gene(s) in a biological sample derived from the animal subject. The variation in the expression level of the marker gene(s) in a biological sample derived from the animal subject can be monitored using the same technique as used in the testing method described above. Furthermore, based on the evaluation, a candidate compound for a pharmaceutical agent can be selected by screening.

All patents, patent applications and references cited herein are incorporated in their entirety by reference. While the invention has been described and exemplified in sufficient detail for those skilled in this art to make and use it, various alternatives, modifications and improvements should be apparent without departing from the spirit and scope of the invention. One skilled in the art readily appreciates that the present invention is well adapted to carry out the objects and obtain the ends and advantages mentioned, as well as those inherent therein.

The methods and reagents described herein are representative of preferred embodiments, are exemplary, and are not intended as limitations on the scope of the invention. Modifications therein and other uses will occur to those skilled in the art. These modifications are encompassed within the spirit of the invention and are defined by the scope of the claims. It will also be readily apparent to a person skilled in the art that varying substitutions and modifications may be made to the invention disclosed herein without departing from the scope and spirit of the invention.

It should be understood that although the present invention has been specifically disclosed by preferred embodiments and optional features, modifications and variations of the concepts herein disclosed may be resorted to by those skilled in the art, and that such modifications and variations are considered to be within the scope of this invention as defined by the appended claims.

What is claimed is:

1. A method to identify a human who has poor survival prognosis colon adenocarcinoma, comprising:
    a.) obtaining a colon adenocarcinoma cell containing test sample from a human;
    b.) conducting at least one hybridization assay of the sample so as to obtain physical data regarding the expression level of miR-10a gene product in the sample; and
    c.) identifying the human as one who has increased risk of poor prognosis colon adenocarcinoma if the physical data indicate that the expression level of miR-10a gene product is higher in the test sample than the expression level of miR-10a gene product of a control.

2. A method to identify a human who has poor survival prognosis colon adenocarcinoma, comprising:
    a.) obtaining a colon adenocarcinoma cell containing test sample from a human;
    b.) conducting at least one hybridization assay of the sample so as to obtain physical data to determine whether the expression level of miR-10a gene product in the sample is higher than expression level of miR-10a gene product in control sample from a healthy subject;
    c.) comparing the expression level of miR-10a gene product in the sample with miR-10a expression in a control sample from a healthy subject; and
    c.) identifying the human as one who has increased risk of poor prognosis colon adenocarcinoma if the physical data indicate that the expression level of miR-10a gene product is higher in the test sample than the expression level of miR-10a gene product of control.

3. The method of claim 2, wherein the sample comprises one or more of tissue, blood, plasma, serum, urine, and feces.

4. The method of claim 2, which further comprises communicating the data or risk to at least one human.

5. A method of diagnosing whether a subject has poor survival prognosis colon adenocarcinoma, comprising:
    (1) reverse transcribing RNA from a test sample obtained from the subject to provide a set of target oligodeoxynucleotides wherein said subject has colon adenocarcinoma;
    (2) hybridizing the target oligodeoxynucleotides to a microarray comprising miRNA-10a specific probe oligonucleotides to provide a hybridization profile for the test sample; and
    (3) comparing the test sample hybridization profile to a hybridization profile generated from a control sample,
    (4) diagnosing the subject as having poor survival prognosis colon adenocarcinoma if the hybridization profile of the test sample displays an increase in signal compared to the signal of the hybridization profile of the control sample.

6. The method of claim 1, wherein the laboratory analysis is selected from the group consisting of: microarray; Northern blot analysis; RT-PCR; and in situ hybridization.

7. The method of claim 1, wherein the sample comprises one or more of tissue, blood, plasma, serum, urine, and feces.

8. The method of claim 1, which further comprises communicating the data or risk to at least one human.

9. The method of claim 1, wherein the at least one miR-10a gene product includes isolated variants or biologically-active fragments thereof.

10. A method of claim 1, which further comprises measuring the level of at least one additional miR gene product in the test sample, wherein the miR is selected from the group consisting of: miR-21; miR-181b; let-7g; miR-16b; miR-106a; miR-103-2; miR-203; and miR-29a.

11. A method of claim 1, which further comprises measuring the level of at least two or more additional miR gene products in the test sample, wherein the miRs are selected from the group consisting of: miR-21; miR-181b; let-7g; miR-16b; miR-106a; miR-103-2; miR-203 and miR-29a.

12. A method of claim 1, which further comprises measuring the level of at least three or more additional miR gene products in the test sample, wherein the miRs are selected from the group consisting of: miR-21; miR-181b; let-7g; miR-16b; miR-106a; miR-103-2; miR-203; and miR-29a.

13. A method of claim 2, which further comprises measuring the level of at least one additional miR gene product in the test sample, wherein the miR is selected from the group consisting of: miR-21; miR-181b; let-7g; miR-16b; miR-106a; miR-103-2; miR-203; and miR-29a.

14. A method of claim 2, which further comprises measuring the level of at least two or more additional miR gene products in the test sample, wherein the miRs are selected from the group consisting of: miR-21; miR-181b; let-7g; miR-16b; miR-106a; miR-103-2; miR-203; and miR-29a.

15. A method of claim 2, which further comprises measuring the level of at least three or more additional miR gene products in the test sample, wherein the miRs are selected from the group consisting of: miR-21; miR-181b; let-7g; miR-16b; miR-106a; miR-103-2; miR-203; and miR-29a.

16. A method of claim 5, which further comprises measuring the level of at least one additional miR gene product in the test sample, wherein the miR is selected from the group consisting of: miR-21; miR-181b; let-7g; miR-16b; miR-106a; miR-103-2; miR-203; and miR-29a.

17. A method of claim 5, which further comprises measuring the level of at least two or more additional miR gene products in the test sample, wherein the miRs are selected from the group consisting of: miR-21; miR-181b; let-7g; miR-16b; miR-106a; miR-103-2; miR-203; miR-29a; and miR-29a.

18. A method of claim 5, which further comprises measuring the level of at least three or more additional miR gene products in the test sample, wherein the miRs are selected from the group consisting of: miR-21; miR-181b; let-7g; miR-16b; miR-106a; miR-103-2; miR-203; and miR-29a.

* * * * *

UNITED STATES PATENT AND TRADEMARK OFFICE
CERTIFICATE OF CORRECTION

PATENT NO. : 8,343,725 B2
APPLICATION NO. : 13/296500
DATED : January 1, 2013
INVENTOR(S) : Carlo M. Croce, Curtis C. Harris and Aaron J. Schetter Page 1 of 1

It is certified that error appears in the above-identified patent and that said Letters Patent is hereby corrected as shown below:

Column 69, Claim 2, Line 47, change "c.)" to -- d.) --

Column 70, Claim 6, Line 10, italicize "in situ"

Column 70, Claim 17, Line 57, delete "miR-29a;"

Signed and Sealed this
Nineteenth Day of February, 2013

Teresa Stanek Rea
*Acting Director of the United States Patent and Trademark Office*